US010017807B2

(12) United States Patent
Srinivasan et al.

(10) Patent No.: US 10,017,807 B2
(45) Date of Patent: Jul. 10, 2018

(54) GENERATING CELL-FREE DNA LIBRARIES DIRECTLY FROM BLOOD

(71) Applicant: Verinata Health, Inc., Redwood City, CA (US)

(72) Inventors: Anupama Srinivasan, Redwood City, CA (US); Richard P. Rava, Redwood City, CA (US)

(73) Assignee: Verinata Health, Inc., San Diego, CA (US)

( * ) Notice: Subject to any disclaimer, the term of this patent is extended or adjusted under 35 U.S.C. 154(b) by 63 days.

(21) Appl. No.: 14/214,277

(22) Filed: Mar. 14, 2014

(65) Prior Publication Data
US 2014/0274740 A1    Sep. 18, 2014

Related U.S. Application Data

(60) Provisional application No. 61/801,126, filed on Mar. 15, 2013.

(51) Int. Cl.
*C12Q 1/68* (2018.01)
*C12Q 1/6809* (2018.01)
*C12Q 1/6806* (2018.01)

(52) U.S. Cl.
CPC ......... *C12Q 1/6809* (2013.01); *C12Q 1/6806* (2013.01)

(58) Field of Classification Search
CPC ............ C12Q 1/6806; C12Q 2521/501; C12Q 2527/101
See application file for complete search history.

(56) References Cited

U.S. PATENT DOCUMENTS

| | | | | |
|---|---|---|---|---|
| 2010/0015621 A1* | 1/2010 | Chang | ................. | C12Q 1/6806 435/6.18 |
| 2010/0120098 A1 | 5/2010 | Grunenwald et al. | | |
| 2010/0184069 A1 | 7/2010 | Fernando et al. | | |
| 2010/0209930 A1 | 8/2010 | Fernando | | |
| 2011/0201507 A1* | 8/2011 | Rava et al. | ...................... | 506/7 |
| 2012/0135874 A1* | 5/2012 | Wang et al. | ...................... | 506/9 |
| 2012/0270739 A1 | 10/2012 | Rava et al. | | |
| 2013/0029852 A1 | 1/2013 | Rava et al. | | |
| 2013/0034546 A1 | 2/2013 | Rava et al. | | |
| 2013/0203606 A1 | 8/2013 | Pollack et al. | | |

FOREIGN PATENT DOCUMENTS

| | | |
|---|---|---|
| WO | WO2013123030 A2 * | 8/2003 |
| WO | 2009/135205 | 11/2009 |
| WO | 2011/090559 | 7/2011 |
| WO | 2014/014497 | 1/2014 |
| WO | WO 2014145078 | 9/2014 |

OTHER PUBLICATIONS

Umetani et al. (Ann. N.Y. Acad. Sci. 1075: 299-307 (2006)).*
El Messaoudi et al.( Clinica Chimica Acta 424 (2013) 222-230).*
Sparks et al.( Prenatal diagnosis 32.1 (2012): 3-9.).*
Syed et al.( Nature Methods 6.11 (2009).).*
Library Preparation: NEBNext® DNA Library Prep Reagent Set for Illumina® Instruction Manual, Version 6.0, NEB #E6000S/L, New England BioLabs, Inc. Jun. 2016, pp. 1-23.*
Ligation Protocol with T4 DNA Ligase (M0202) NEB, printed from https://www.neb.com/protocols/1/01/01/dna-ligation-with-t4-dna-ligase-m02002 on Jun. 6, 2017 as p. 1/1.*
Yau et al. Thermal denaturation studies of acetylated nucleosomes and oligonucleosomes. European Journal of Biochemistry, vol. 129, No. 2, pp. 281-288, Dec. 1982. (Year: 1982).*
Bashkin et al. Structure of DNA in a nucleosome core at high salt concentration and at high temperature. Biochemistry, vol. 32, No. 8, pp. 1895-1898, Mar. 1993. (Year: 1993).*
Lohman et al. "DNA Ligases" in Current Protocols in Molecular Biology, Supplement 94, pp. 3.14.1-3.14.7, Apr. 2011. (Year: 2011).*
Adey et al. 2010. "Rapid, low-input, low-bias construction of shotgun fragment libraries by high-density in vitro transposition," *Genome Biology* 11: 1-17.
Bianchi et al. 2012. "Genome-Wide Fetal Aneuploidy Detection by Maternal Plasma DNA Sequencing," *Obstetrics & Gynecology* 119(5):1-13.
Boom et al. 1990. "Rapid and Simple Method for Purification of Nucleic Acids," *Journal of Clinical Microbiology* 28(3):495-503.
GE Healthcare 2010. "Albumin & IgG Depletion SpinTrap," *Product Booklet* pp. 1-12.
Hawkins et al. 1994. "DNA purification and isolation using a solid-phase," *Nucleic Acids Research* 22(21): 4543-4544.
Li et al. 2005. "Rapid spontaneous accessibility of nucleosomal DNA," *Nature Structural & Molecular Biology* 12(1):46-53.
Sehnert et al. 2011. "Optimal Detection of Fetal Chromosomal abnormalities by Massively Parallel DNA Sequencing of Cell-Free Fetal DNA from Maternal Blood," *Clinical Chemistry* 57(7):1-8.
PCT International Search Report and Written Opinion dated Jul. 11, 2014 issued in PCT/US2014/029739.

(Continued)

*Primary Examiner* — Jennifer Dunston
(74) *Attorney, Agent, or Firm* — Weaver Austin Villeneuve & Sampson LLP

(57) ABSTRACT

The disclosure provides methods and kits for preparing sequencing library to detect chromosomal abnormality using cell-free DNA (cfDNA) without the need of first isolating the cfDNA from a liquid fraction of a test sample. In some embodiments, the method involves reducing the binding between the cfDNA and nucleosomal proteins without unwinding the cfDNA from the nucleosomal proteins. In some embodiments, the reduction of binding may be achieved by treating with a detergent or heating. In some embodiments, the method further involves freezing and thawing the test sample before reducing the binding between the cfDNA and the nucleosomal proteins. In some embodiments, the test sample is a peripheral blood sample from a pregnant woman including cfDNA of both a mother and a fetus, wherein the methods may be used to detect fetal chromosomal abnormality such as copy number variation. In other embodiments, the test sample is a peripheral blood sample from a patient known or suspected to have cancer, wherein the methods can be used to detect chromosomal abnormalities in the cfDNA of the patient. Kits for detection of copy number variation of the fetus using the disclosed methods are also provided.

35 Claims, 36 Drawing Sheets

(56) References Cited

OTHER PUBLICATIONS

Srinivasan, et al. 2013. "Noninvasive Detection of Fetal Subchromosome Abnormalities via Deep Sequencing of Maternal Plasma," *The American Journal of Human Genetics* 92:167-176.

Ulvik, et al. 2001, "Single Nucleotide Polymorphism (SNP) Genotyping in Unprocessed Whole Blood and Serum by Real-Time PCR: Application to SNPs Affecting Homocysteine and Folate Metabolism," Clinical Chemistry 47(11):2050-2053.

Zmatlikova et al. (2010) "Non-enzymatic posttranslational modifications of bovine serum albumin by oxo-compounds investigated by high-performance liquid chromatography—mass spectrometry and capillary zone electrophoresis—mass spectrometry," Journal of Chromatography A, 1217: 8009-8015.

EP Office Action dated May 19, 2017 in EP Application No. 14717959.2.

\* cited by examiner

GENERATING CELL-FREE DNA LIBRARIES DIRECTLY FROM BLOOD

CROSS REFERENCE TO RELATED APPLICATIONS

This application claims the benefit under 35 U.S.C. § 119(e)(1) of U.S. Provisional Patent Application No. 61/801,126, filed Mar. 15, 2013, which is hereby incorporated by reference in its entirety.

BACKGROUND

One of the critical endeavors in human medical research is the discovery of genetic abnormalities that produce adverse health consequences. In many cases, specific genes and/or critical diagnostic markers have been identified for use in prenatal and cancer diagnosis, for example.

Conventional procedures for genetic screening and biological dosimetry have utilized invasive procedures, e.g. amniocentesis, to obtain cells for the analysis of karyotypes. The advent of technologies that allow for sequencing entire genomes in relatively short time, and the discovery of circulating cell-free DNA (cfDNA) have provided the opportunity to compare genetic material originating from one chromosome to be compared to that of another without the risks associated with invasive sampling methods. However, the limitations of the existing methods, which include insufficient sensitivity stemming from the limited levels of cfDNA and the special care required in extracting cfDNA, underlie the continuing need for improved methods that would provide inexpensive and reliable diagnosis protocols utilizing cfDNA in a variety of clinical settings.

Conventionally, when blood is collected in the commonly used blood collection tubes, such as EDTA tubes and ACD tubes, the plasma has to be separated from other blood fractions before purifying cfDNA. Plasma is generally separated from other blood components by centrifugation. The reason for the mandatory plasma isolation step is to avoid contaminating the cfDNA with cellular DNA from the white blood cells. In addition to separating the plasma, cfDNA must be purified by, e.g., releasing it from nucleosomes prior to sequencing. Unfortunately, the purification steps associated with conventional techniques for isolating cfDNA increase the cost and complexity of the cfDNA diagnostic procedures.

INCORPORATION BY REFERENCE

All patents, patent applications, and other publications, including all sequences disclosed within these references, referred to herein are expressly incorporated herein by reference, to the same extent as if each individual publication, patent or patent application was specifically and individually indicated to be incorporated by reference. All documents cited are, in relevant part, incorporated herein by reference in their entireties for the purposes indicated by the context of their citation herein. However, the citation of any document is not to be construed as an admission that it is prior art with respect to the present disclosure.

SUMMARY

The disclosure provides methods and kits for preparing sequencing library to detect chromosomal abnormality using cell-free DNA (cfDNA) without the need of first isolating the cfDNA from a liquid fraction of a test sample. In some embodiments, the method involves reducing the binding between the cfDNA and nucleosomal proteins without unwinding the cfDNA from the nucleosomal proteins. In a process by which a sequencing library is generated directly from a biological fluid without an intervening DNA isolation step, there is a minimum amount of the fluid required to successfully generate the library and still generate useable downstream data.

In some embodiments, the reduction of binding may be achieved by treating with a detergent or heating. In some embodiments, the method further involves freezing and thawing the test sample before reducing the binding between the cfDNA and the nucleosomal proteins. In some embodiments, the test sample is a peripheral blood sample from a pregnant woman including cfDNA of both a mother and a fetus, wherein the methods may be used to detect fetal chromosomal abnormality such as copy number variation. Kits for detection of copy number variation of the fetus using the disclosed methods are also provided.

In some embodiments, the disclosure provides a method for obtaining sequence information from a blood sample comprising cell-free DNA. The method involves the following: (a) obtaining the plasma fraction of a whole blood sample; (b) without first purifying the cell-free DNA from the plasma fraction, preparing a sequencing library from the cell-free DNA; and (c) sequencing said sequencing library to obtain sequence information. In some embodiments, the method further includes obtaining the whole blood sample containing cell-free DNA from a subject. In some embodiments, the whole blood sample is a peripheral blood sample.

In some embodiments, the operation of obtaining the plasma fraction involves centrifuging the whole blood sample and removing the resulting buffy coat and hematocrit fractions. In some embodiments, the operation of obtaining the plasma fraction further involves centrifuging to the plasma fraction to remove solids from the plasma fraction. In some embodiments, the process further involves stabilizing white blood cells prior to centrifugation.

In some embodiments, the process further involves only a single centrifugation step performed on the whole blood sample prior to preparing the sequencing library, wherein the single centrifugation step is performed at an acceleration of at least about 10,000 g.

In some embodiments, the operation of preparing a sequencing library from the cell-free DNA involves contacting the plasma fraction with sequencing adaptors and a ligase.

In some embodiments, the process further involves exposing the plasma fraction to conditions that reduce the binding of cell-free DNA to nucleosomal proteins without fully-detaching the cell-free DNA from the nucleosomal proteins. In some embodiments, the conditions that reduce the binding of cell-free DNA to nucleosomal proteins include exposing the plasma fraction to a detergent. In some embodiments, the detergent is a non-ionic detergent. In some embodiments, the conditions that reduce the binding of cell-free DNA to nucleosomal proteins include heating the plasma fraction to a temperature of between about 35° C. and 70° C. while contacting the plasma fraction with the sequencing adaptors and ligase.

In some embodiments, prior to preparing a sequencing library from the cell-free DNA, the cell-free DNA is not isolated from the whole blood sample or the plasma. In some embodiments, prior to preparing a sequencing library from the cell-free DNA, the cell-free DNA is not removed from the whole blood sample or the plasma by contact with a support matrix.

In some embodiments, prior to and during preparing a sequencing library from the cell-free DNA, no protease is added to the plasma fraction. In some embodiments, the process also involves removing serum proteins from the plasma fraction prior to preparing a sequencing library from the cell-free DNA. In some embodiments, removing serum proteins from the plasma fraction involves passing the plasma fraction over a support matrix which adsorbs the serum proteins.

In some embodiments, massively parallel sequencing is used to perform on the sequencing libraries. In some embodiments, the sequence information comprises sequence reads. In some embodiments, the process further includes mapping the sequence reads to a reference sequence.

In some embodiments, the subject providing the blood sample is a pregnant mother. The cell-free DNA includes fetal cell-free DNA of a fetus carried by the pregnant mother. In some embodiments, the process further involves using the cell-free DNA to determine copy number variation (CNV) in the fetus.

In other embodiments, the subject providing the blood sample is a cancer patient. The cell-free DNA includes cell-free DNA of a cancer genome. In some embodiments, the process further involves using the cell-free DNA to determine copy number variation (CNV) in the cancer genome. In some embodiments, the CNV results from loss of homozygosity (LOH).

In some aspects, the disclosure pertains to methods for obtaining sequence information from a whole blood sample containing cell-free DNA (e.g., peripheral blood from a subject such as a pregnant mother). Such methods may be characterized by the following operations: (a) freezing the whole blood sample; (b) thawing the frozen whole blood sample; (c) separating solids from the thawed whole blood sample to obtain a liquid fraction; (d) preparing a sequencing library from cell-free DNA in the liquid fraction; and (e) sequencing said sequencing library to obtain sequence information. In some implementations, preparing the sequencing library from cell-free DNA is performed without first purifying the cell-free DNA from the liquid fraction.

Such method may further include, prior to (a), fixing blood cells in the whole blood sample. The freezing may degrade the blood cells without releasing DNA from nuclei of the blood cells. Separating solids from the thawed whole blood sample may include centrifuging the thawed whole blood sample. As an example, only a single centrifugation step is performed on the thawed whole blood sample prior to preparing the sequencing library, and wherein the single centrifugation step is performed at an acceleration of at least about 10,000 g.

In certain embodiments, preparing a sequencing library from the cell-free DNA includes contacting the liquid fraction with sequencing adaptors and a ligase. This may be conducted in a process that includes exposing the liquid fraction to conditions that reduce the binding of cell-free DNA to nucleosomal proteins without fully-detaching the cell-free DNA from the nucleosomal proteins. The conditions that reduce the binding of cell-free DNA to nucleosomal proteins may include exposing the liquid fraction to a detergent (e.g., a non-ionic detergent) and/or heating the plasma fraction to a temperature of between about 35° C. and 70° C. while contacting the liquid fraction with the sequencing adaptors and ligase.

In certain embodiments, prior to preparing a sequencing library from the cell-free DNA, the cell-free DNA is not isolated from the whole blood sample or the liquid fraction (e.g., not contacting the liquid fraction with a support matrix). In certain embodiments, during preparing a sequencing library from the cell-free DNA, no protease is added to the liquid fraction.

In certain embodiments, the method additionally includes removing serum proteins from the liquid fraction prior to preparing a sequencing library from the cell-free DNA. The removing may include passing the liquid fraction over a support matrix which adsorbs the serum proteins.

In certain embodiments, sequencing the library includes conducting massively parallel sequencing. The sequence information may include sequence reads, which may be mapped to a reference sequence.

In embodiments where the subject is a pregnant individual, the cell-free DNA is fetal cell-free DNA of a fetus carried by the pregnant mother. The methods may also include using the cell-free DNA to determine copy number variation (CNV) in the fetus. In some embodiments, the subject is a cancer patient. As an example, the cell-free DNA may be cell-free DNA of a cancer genome, which may be used to determine copy number variation (CNV) in such genome. As an example, the CNV results from loss of homozygosity (LOH).

Another aspect of the disclosure concerns kits for classifying a copy number variation in a fetal genome, which kits may be characterized by the following elements: (a) a sample collection device for holding a maternal test sample comprising fetal and maternal nucleic acids; (b) an in-process positive control (IPC) containing one or more nucleic acids comprising one or more chromosomal aneuploidies of interest, where the IPC provides a qualitative positive sequence dose value for said one or more chromosomal aneuploidies of interest; and (c) one or more fixatives for white blood cell nuclei, one or more nuclease inhibitors, one or more albumin depletion columns, one or more Ig depletion columns, one or more nonionic detergents or salts, or combinations thereof. As an example, the one or more nonionic detergents may include TWEEN®-20, at a concentration of between about 0.1% to about 5%.

In some implementations, the IPC includes markers to track sample(s) through the sequencing process. In certain embodiments, the one or more nucleic acids comprising one or more chromosomal aneuploidies of interest in the IPC comprise i) nucleic acids comprising one or more internal positive controls for calculating a first fetal fraction and detecting copy number variations at a first location on a reference genome; and ii) nucleic acids comprising one or more internal positive controls for calculating a second fetal fraction at a second location on the reference genome other than the first location on the reference genome for detecting the copy number variation in i). In certain embodiments, the IPC is configured to relate the sequence information obtained for the maternal test sample to the sequence information obtained from a set of qualified samples that were sequenced at a different time.

The kit may include one or more marker molecules such as nucleic acids and/or nucleic acid mimics that provide antigenomic marker sequence(s) suitable for tracking and verifying sample integrity. The marker molecules may include one or more mimetics selected from the group consisting of a morpholino derivative, a peptide nucleic acid (PNA), and a phosphorothioate DNA.

In certain embodiments, the sample collection device comprises a device for collecting blood and, optionally a receptacle for containing blood. Such device or receptacle may include an anticoagulant and/or cell fixative, and/or said antigenomic marker sequence(s) and/or said internal positive controls.

The kit may also include a reagent for sequencing library preparation such as a solution for end-repairing DNA, and/or a solution for dA-tailing DNA, and/or a solution for adaptor ligating DNA. In some embodiments, the kit additionally includes instructional materials teaching the use of said reagents to determine copy number variation in a biological sample. As an example, the instructional materials teach the use of said materials to detect a monosomy and/or a trisomy. As another example, the instructional materials teach the use of said materials to detect a cancer or a predisposition to a cancer. In some implementations, the kit does not include reagents for detecting any polymorphism used as a marker for the fetal fraction.

In certain embodiments, the kit includes a sequencer for sequencing the fetal and maternal nucleic acids. In certain embodiments, the kit includes consumable portion of a sequencer. The consumable portion is configured to sequence fetal and maternal nucleic acids from one or more maternal test samples. Examples of consumable portions include a flow cell and a chip configured to detect ions.

In certain embodiments, the IPC contains a trisomy selected from the group consisting of trisomy 21, trisomy 18, trisomy 21, trisomy 13, trisomy 16, trisomy 13, trisomy 9, trisomy 8, trisomy 22, XXX, XXY, and XYY (e.g., trisomy 21 (T21), trisomy 18 (T18), and trisomy 13 (T13)). In certain embodiments, the IPC contains an amplification or a deletion of a p arm or a q arm of any one or more of chromosomes 1-22, X and Y. In certain embodiments, the IPC contains a partial deletion of one or more arms selected from the group of 1p, 1q, 3q, 4p, 5p, 5q, 7q, 9q, 10p, 11q, 13q, 18, 15q, 17p, 22p and 22q. In certain embodiments, the IPC contains a partial duplication of one or more arms selected from the group of 5q, 7q, 8p, 13q, 12p, 15q, and 17p. In certain embodiments, the IPC is configured to provide data for calculating a sequence dose value for said one or more chromosomal aneuploidies of interest.

Another aspect of the disclosure concerns kits for classifying a copy number variation in a cancer genome, which kits contain (a) a sample collection device for holding a cancer patient test sample comprising cancer and non-cancer nucleic acids; (b) an in-process positive control (IPC) comprising one or more nucleic acids comprising one or more chromosomal aneuploidies of interest, wherein the IPC provides a qualitative positive sequence dose value for said one or more chromosomal aneuploidies of interest; and (c) one or more fixatives for white blood cell nuclei, one or more nuclease inhibitors, one or more albumin depletion columns, one or more Ig depletion columns, one or more nonionic detergents or salts, or combinations thereof.

BRIEF DESCRIPTION OF THE DRAWINGS

FIG. 11A shows all 31 samples, and FIG. 11B shows the same data without the 6 samples that had high DNA concentration.

DETAILED DESCRIPTION

Definitions

Figure 1A:
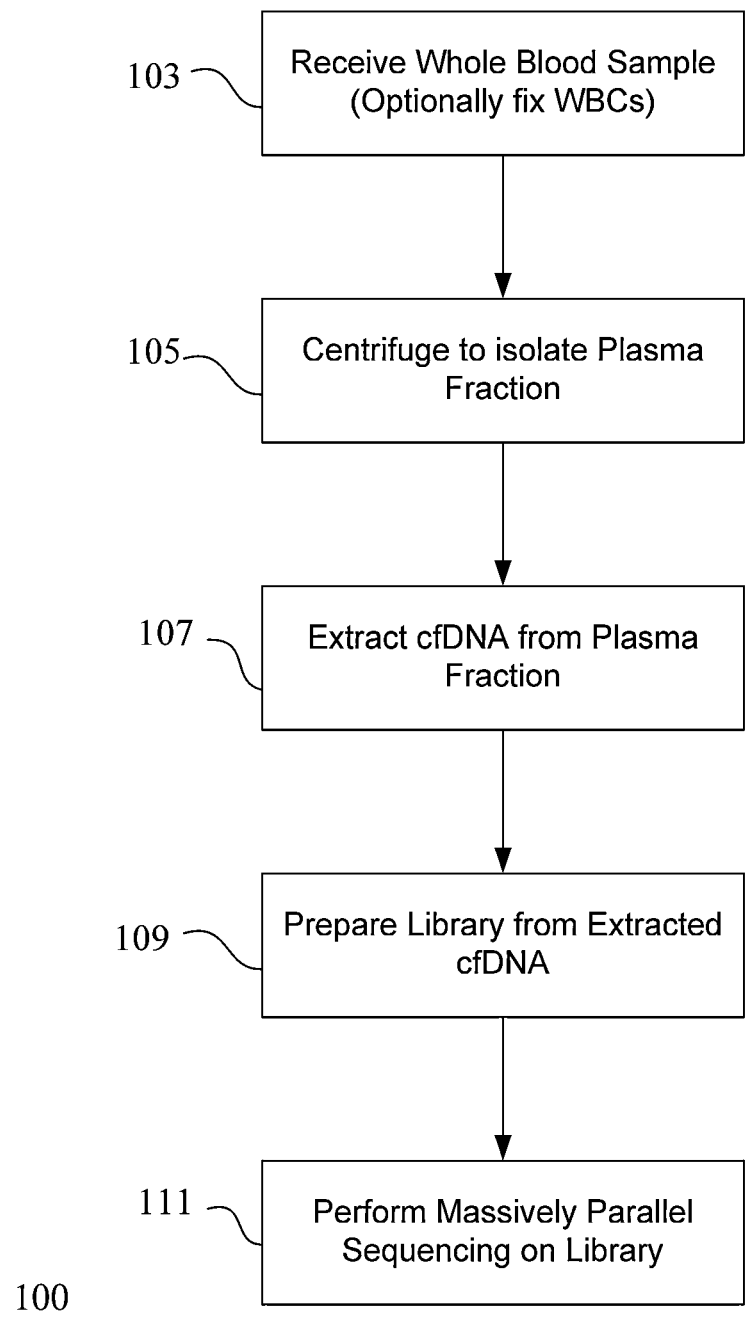
FIG. 1A shows a conventional process for processing cfDNA using next generation sequencing.

"Whole Blood sample" herein refers to a whole blood sample that has not been fractionated or separated into its component parts. Whole blood is often combined with an anticoagulant such as EDTA or ACD during the collection process, but is generally otherwise unprocessed. In the US, the capitalized "Whole Blood" means a specific standardized product for transfusion or further processing, where "whole blood" is any unmodified collected blood.

"Blood fractionation" is the process of fractionating whole blood or separating it into its component parts. This is typically done by centrifuging the blood. The resulting components are:
- a clear solution of blood plasma in the upper phase (which can be separated into its own fractions),
- a buffy coat, which is a thin layer of leukocytes (white blood cells) mixed with platelets in the middle, and
- erythrocytes (red blood cells) at the bottom of the centrifuge tube in the hematocrit faction.

Serum separation tubes (SSTs) are tubes used in phlebotomy containing a silicone gel; when centrifuged the silicone gel forms a layer on top of the buffy coat, allowing the blood plasma to be removed more effectively for testing and related purposes.

"Blood plasma" or "plasma" is the straw-colored/pale-yellow liquid component of blood that normally holds the blood cells in whole blood in suspension. It makes up about 55% of total blood by volume. It is the intravascular fluid part of [extracellular fluid] (all body fluid outside of cells). It is mostly water (93% by volume), and contains dissolved proteins including albumins, immunoglobulins, and fibrinogen, glucose, clotting factors, electrolytes ($Na^+$, $Ca^{2+}$, $Mg^{2+}$, $HCO_3^-$ $Cl^-$ etc.), hormones and carbon dioxide.

Blood plasma is prepared by spinning a tube of whole blood and containing an anticoagulant in a centrifuge until the blood cells fall to the bottom of the tube. The blood plasma is then poured or drawn off. Blood plasma has a density of approximately 1025 $kg/m^3$, or 1.025 kg/l.

"Peripheral blood" is blood that obtained from acral areas, or from the circulation remote from the heart; the blood in the systemic circulation.

"Fixing" refers to a technique that maintains the structure of cells and/or sub-cellular components such as cell organelles (e.g., nucleus). Fixing modifies the chemical or biological structure cellular components by, e.g., cross-linking them. Fixing may cause whole cells and cellular organelles to resist lysis. Of interest, fixing may also cause cellular nucleic acids to resist release into a surrounding medium. For example, fixing may prevent nuclear DNA from white blood cells to resist release into a plasma fraction during centrifugation of whole blood.

"Fixative" refers to an agent such as a chemical or biological reagent that fixes cellular nucleic acids and thereby causes cells to resist release of such nucleic acids into a surrounding medium. A fixative may disable cellular proteolytic enzymes and nucleases. Examples of fixatives include aldehydes (e.g., formaldehyde), alcohols, and oxidizing agents. Examples of suitable fixatives are presented in US Patent Application Publication 2010/0184069, filed Jan. 19, 2010, and in US Patent Application Publication No. 2010/209930, filed Feb. 11, 2010, each incorporated herein by reference in its entirety. A vendor of commercially available fixative compositions for fixing nuclei of white blood cells is Streck, Inc. of Omaha Nebr. Streck blood collection tubes such the Streck Cell-free DNA BCT contain a mild preservative, which fixes cellular nuclei and large cellular components, thereby inhibiting white blood cell lysis that can contaminate plasma DNA with cellular DNA.

"Freeze" means to turn a liquid sample into a solid sample by lowering the temperature and optionally increasing the pressure of the sample. In a sample containing biological materials such as cells, freezing typically forms ice crystals, which will break or otherwise disrupt the biological materials. This disruption may involve breaking apart cell membranes such cellular components are no longer confined to their original cells.

"Thaw" means to convert a frozen sample back into liquid sample by increasing the temperature and optionally decrasing the pressure of the sample. A thawed sample containing biological materials may contain various cellular constituents unconfined by the cell membranes. In the case of thawed blood, such cellular constituents include, for example, cell nuclei, other cell organelles, hemoglobin, denatured proteins, etc.

The term "copy number variation" herein refers to variation in the number of copies of a nucleic acid sequence present in a test sample in comparison with the copy number of the nucleic acid sequence present in a qualified sample. In certain embodiments, the nucleic acid sequence is 1 kb or larger. In some cases, the nucleic acid sequence is a whole chromosome or significant portion thereof. A "copy number variant" refers to the sequence of nucleic acid in which copy-number differences are found by comparison of a sequence of interest in test sample with an expected level of the sequence of interest. For example, the level of the sequence of interest in the test sample is compared to that present in a qualified sample. Copy number variants/variations include deletions, including microdeletions, insertions, including microinsertions, duplications, multiplications, inversions, translocations and complex multi-site variants. CNVs encompass chromosomal aneuploidies and partial aneuploidies.

The term "aneuploidy" herein refers to an imbalance of genetic material caused by a loss or gain of a whole chromosome, or part of a chromosome.

The terms "chromosomal aneuploidy" and "complete chromosomal aneuploidy" herein refer to an imbalance of genetic material caused by a loss or gain of a whole chromosome, and includes germline aneuploidy and mosaic aneuploidy.

The terms "partial aneuploidy" and "partial chromosomal aneuploidy" herein refer to an imbalance of genetic material caused by a loss or gain of part of a chromosome e.g. partial monosomy and partial trisomy, and encompasses imbalances resulting from translocations, deletions and insertions.

The term "aneuploid sample" herein refers to a sample indicative of a subject whose chromosomal content is not euploid, i.e. the sample is indicative of a subject with an abnormal copy number of chromosomes or portions or chromosomes.

The term "aneuploid chromosome" herein refers to a chromosome that is known or determined to be present in a sample in an abnormal copy number.

The term "plurality" refers to more than one element. For example, the term is used herein in reference to a number of nucleic acid molecules or sequence tags that is sufficient to identify significant differences in copy number variations (e.g. chromosome doses) in test samples and qualified samples using the methods disclosed herein. In some embodiments, at least about $3 \times 10^6$ sequence tags, at least about $5 \times 10^6$ sequence tags, at least about $8 \times 10^6$ sequence tags, at least about $10 \times 10^6$ sequence tags, at least about $15 \times 10^6$ sequence tags, at least about $20 \times 10^6$ sequence tags, at least about $30 \times 10^6$ sequence tags, at least about $40 \times 10^6$ sequence tags, or at least about $50 \times 10^6$ sequence tags comprising between about 20 and 40 bp reads are obtained for each test sample.

The terms "polynucleotide", "nucleic acid" and "nucleic acid molecules" are used interchangeably and refer to a covalently linked sequence of nucleotides (i.e., ribonucleotides for RNA and deoxyribonucleotides for DNA) in which the 3' position of the pentose of one nucleotide is joined by a phosphodiester group to the 5' position of the pentose of the next, include sequences of any form of nucleic acid, including, but not limited to RNA and DNA molecules such as cfDNA molecules. The term "polynucleotide" includes, without limitation, single- and double-stranded polynucleotide.

The term "portion" is used herein in reference to the amount of sequence information of fetal and maternal nucleic acid molecules in a biological sample that in sum amount to less than the sequence information of 1 human genome.

The term "test sample" herein refers to a sample, typically derived from a biological fluid, cell, tissue, organ, or organism, comprising a nucleic acid or a mixture of nucleic acids comprising at least one nucleic acid sequence that is to be screened for copy number variation. In certain embodiments the sample comprises at least one nucleic acid sequence whose copy number is suspected of having undergone variation. Such samples include, but are not limited to sputum/oral fluid, amniotic fluid, blood, a blood fraction, or fine needle biopsy samples (e.g., surgical biopsy, fine needle biopsy, etc.) urine, peritoneal fluid, pleural fluid, and the like. Although the sample is often taken from a human subject (e.g., patient), the assays can be used to copy number variations (CNVs) in samples from any mammal, including, but not limited to dogs, cats, horses, goats, sheep, cattle, pigs, etc. The sample may be used directly as obtained from the biological source or following a pretreatment to modify the character of the sample. For example, such pretreatment may include preparing plasma from blood, diluting viscous fluids and so forth. Methods of pretreatment may also involve, but are not limited to, filtration, precipitation, dilution, distillation, mixing, centrifugation, freezing, lyophilization, concentration, amplification, nucleic acid fragmentation, inactivation of interfering components, the addition of reagents, lysing, etc. If such methods of pretreatment are employed with respect to the sample, such pretreatment methods are typically such that the nucleic acid(s) of interest remain in the test sample, preferably at a concentration proportional to that in an untreated test sample (e.g., namely, a sample that is not subjected to any such pretreatment method(s)). Such "treated" or "processed" samples are still considered to be biological "test" samples with respect to the methods described herein.

The term "normalizing sequence" herein refers to a sequence that is used to normalize the number of sequence tags mapped to a sequence of interest associated with the normalizing sequence. In some embodiments, the normalizing sequence displays a variability in the number of sequence tags that are mapped to it among samples and sequencing runs that approximates the variability of the sequence of interest for which it is used as a normalizing parameter, and that can differentiate an affected sample from one or more unaffected samples. In some implementations, the normalizing sequence best or effectively differentiates, when compared to other potential normalizing sequences such as other chromosomes, an affected sample from one or more unaffected samples. A "normalizing chromosome" or "normalizing chromosome sequence" is an example of a "normalizing sequence". A "normalizing chromosome sequence" or "normalizing chromosome" can be composed of a single chromosome or of a group of chromosomes. A "normalizing segment" is another example of a "normalizing sequence". A "normalizing segment sequence" can be composed of a single segment of a chromosome or it can be composed of two or more segments of the same or of different chromosomes. In certain embodiments, a normalizing sequence is intended to normalize for variability such as process-related variability, which stems from interchromosomal (intra-run), inter-sequencing (inter-run) and/or platform-dependent variability.

The term "sequence dose" herein refers to a parameter that relates the number of sequence tags identified for a sequence of interest and the number of sequence tags identified for the normalizing sequence. In some cases, the sequence dose is the ratio of the number of sequence tags identified for a sequence of interest to the number of sequence tags identified for the normalizing sequence. In some cases, the sequence dose refers to a parameter that relates the sequence tag density of a sequence of interest to the tag density of a normalizing sequence. A "test sequence dose" is a parameter that relates the sequence tag density of a sequence of interest, e.g. chromosome 21, to that of a normalizing sequence e.g. chromosome 9, determined in a test sample. Similarly, a "qualified sequence dose" is a parameter that relates the sequence tag density of a sequence of interest to that of a normalizing sequence determined in a qualified sample.

The term "sequence tag density" herein refers to the number of sequence reads that are mapped to a reference genome sequence; e.g. the sequence tag density for chromosome 21 is the number of sequence reads generated by the sequencing method that are mapped to chromosome 21 of the reference genome. The term "sequence tag density ratio" herein refers to the ratio of the number of sequence tags that are mapped to a chromosome of the reference genome e.g. chromosome 21, to the length of the reference genome chromosome.

The term "Next Generation Sequencing (NGS)" herein refers to sequencing methods that allow for massively parallel sequencing of clonally amplified molecules and of single nucleic acid molecules. NGS is synonymous with "massively parallel sequencing" for most purposes. Non-limiting examples of NGS include sequencing-by-synthesis using reversible dye terminators, and sequencing-by-ligation.

The terms "threshold value" and "qualified threshold value" herein refer to any number that is used as a cutoff to characterize a sample such as a test sample containing a nucleic acid from an organism suspected of having a medical condition. The threshold may be compared to a parameter value to determine whether a sample giving rise to such parameter value suggests that the organism has the medical condition. In certain embodiments, a qualified threshold value is calculated using a qualifying data set and serves as a limit of diagnosis of a copy number variation e.g. an aneuploidy, in an organism. If a threshold is exceeded by results obtained from methods disclosed herein, a subject can be diagnosed with a copy number variation e.g. trisomy 21. Appropriate threshold values for the methods described herein can be identified by analyzing normalizing values (e.g. chromosome doses, NCVs or NSVs) calculated for a training set of samples. Threshold values can be identified using qualified (i.e. unaffected) samples in a training set which comprises both qualified (i.e. unaffected) samples and affected samples. The samples in the training set known to have chromosomal aneuploidies (i.e. the affected samples) can be used to confirm that the chosen thresholds are useful in differentiating affected from unaffected samples in a test set (see the Examples herein). The choice of a threshold is dependent on the level of confidence that the user wishes to have to make the classification. In some embodiments, the training set used to identify appropriate threshold values comprises at least 10, at least 20, at least 30, at least 40, at least 50, at least 60, at least 70, at least 80, at least 90, at least 100, at least 200, at least 300, at least 400, at least 500, at least 600, at least 700, at least 800, at least 900, at least 1000, at least 2000, at least 3000, at least 4000, or more qualified samples. It may advantageous to use larger sets of qualified samples to improve the diagnostic utility of the threshold values.

The term "normalizing value" herein refers to a numerical value that relates the number of sequence tags identified for the sequence (e.g. chromosome or chromosome segment) of interest to the number of sequence tags identified for the normalizing sequence (e.g. normalizing chromosome or normalizing chromosome segment). For example, a "normalizing value" can be a chromosome dose as described elsewhere herein, or it can be an NCV (Normalized Chromosome Value) as described elsewhere herein, or it can be an NSV (Normalized Segment Value) as described elsewhere herein.

The term "read" refers to a sequence read from a portion of a nucleic acid sample. Typically, though not necessarily, a read represents a short sequence of contiguous base pairs in the sample. The read may be represented symbolically by the base pair sequence (in ATCG) of the sample portion. It may be stored in a memory device and processed as appropriate to determine whether it matches a reference sequence or meets other criteria. A read may be obtained directly from a sequencing apparatus or indirectly from stored sequence information concerning the sample. In some cases, a read is a DNA sequence of sufficient length (e.g., at least about 30 bp) that can be used to identify a larger sequence or region, e.g. that can be aligned and specifically assigned to a chromosome or genomic region or gene.

The term "sequence tag" is herein used interchangeably with the term "mapped sequence tag" to refer to a sequence read that has been specifically assigned i.e. mapped, to a larger sequence e.g. a reference genome, by alignment. Mapped sequence tags are uniquely mapped to a reference genome i.e. they are assigned to a single location to the reference genome. Tags may be provided as data structures or other assemblages of data. In certain embodiments, a tag contains a read sequence and associated information for that read such as the location of the sequence in the genome, e.g., the position on a chromosome. In certain embodiments, the location is specified for a positive strand orientation. A tag may be defined to provide a limit amount of mismatch in aligning to a reference genome. Tags that can be mapped to more than one location on a reference genome i.e. tags that do not map uniquely, may not be included in the analysis.

As used herein, the terms "aligned", "alignment", or "aligning" refer to the process of comparing a read or tag to a reference sequence and thereby determining whether the reference sequence contains the read sequence. If the reference sequence contains the read, the read may be mapped to the reference sequence or, in certain embodiments, to a particular location in the reference sequence. In some cases, alignment simply tells whether or not a read is a member of a particular reference sequence (i.e., whether the read is present or absent in the reference sequence). For example, the alignment of a read to the reference sequence for human chromosome 13 will tell whether the read is present in the reference sequence for chromosome 13. A tool that provides this information may be called a set membership tester. In some cases, an alignment additionally indicates a location in the reference sequence where the read or tag maps to. For example, if the reference sequence is the whole human genome sequence, an alignment may indicate that a read is present on chromosome 13, and may further indicate that the read is on a particular strand and/or site of chromosome 13.

Aligned reads or tags are one or more sequences that are identified as a match in terms of the order of their nucleic acid molecules to a known sequence from a reference genome. Alignment can be done manually, although it is typically implemented by a computer algorithm, as it would be impossible to align reads in a reasonable time period for implementing the methods disclosed herein. One example of an algorithm from aligning sequences is the Efficient Local Alignment of Nucleotide Data (ELAND) computer program distributed as part of the Illumina Genomics Analysis pipeline. Alternatively, a Bloom filter or similar set membership tester may be employed to align reads to reference genomes. See U.S. Patent Application No. 61/552,374 filed Oct. 27, 2011 which is incorporated herein by reference in its entirety. The matching of a sequence read in aligning can be a 100% sequence match or less than 100% (non-perfect match).

As used herein, the term "reference genome" or "reference sequence" refers to any particular known genome sequence, whether partial or complete, of any organism or virus which may be used to reference identified sequences from a subject. For example, a reference genome used for human subjects as well as many other organisms is found at the National Center for Biotechnology Information at www.ncbi.nlm.nih.gov. A "genome" refers to the complete genetic information of an organism or virus, expressed in nucleic acid sequences.

In various embodiments, the reference sequence is significantly larger than the reads that are aligned to it. For example, it may be at least about 100 times larger, or at least about 1000 times larger, or at least about 10,000 times larger, or at least about $10^5$ times larger, or at least about $10^6$ times larger, or at least about $10^7$ times larger.

In one example, the reference sequence is that of a full length human genome. Such sequences may be referred to as genomic reference sequences. In another example, the reference sequence is limited to a specific human chromosome such as chromosome 13. Such sequences may be referred to as chromosome reference sequences. Other examples of reference sequences include genomes of other species, as well as chromosomes, sub-chromosomal regions (such as strands), etc. of any species.

In various embodiments, the reference sequence is a consensus sequence or other combination derived from multiple individuals. However, in certain applications, the reference sequence may be taken from a particular individual.

The term "maternal sample" herein refers to a biological sample obtained from a pregnant subject e.g. a woman.

The term "biological fluid" herein refers to a liquid taken from a biological source and includes, for example, blood, serum, plasma, sputum, lavage fluid, cerebrospinal fluid, urine, semen, sweat, tears, saliva, and the like. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

The terms "maternal nucleic acids" and "fetal nucleic acids" herein refer to the nucleic acids of a pregnant female subject and the nucleic acids of the fetus being carried by the pregnant female, respectively.

As used herein, the term "fetal fraction" refers to the fraction of fetal nucleic acids present in a sample comprising fetal and maternal nucleic acid. Fetal fraction is often used to characterize the cfDNA in a mother's blood.

As used herein the term "chromosome" refers to the heredity-bearing gene carrier of a living cell which is derived from chromatin and which comprises DNA and protein components (especially histones). The conventional internationally recognized individual human genome chromosome numbering system is employed herein.

The term "subject" herein refers to a human subject as well as a non-human subject such as a mammal, an invertebrate, a vertebrate, a fungus, a yeast, a bacteria, and a virus. Although the examples herein concern humans and the language is primarily directed to human concerns, the concepts disclosed herein are applicable to genomes from any plant or animal, and are useful in the fields of veterinary medicine, animal sciences, research laboratories and such.

The term "condition" herein refers to "medical condition" as a broad term that includes all diseases and disorders, but can include [injuries] and normal health situations, such as pregnancy, that might affect a person's health, benefit from medical assistance, or have implications for medical treatments.

The term "complete" is used herein in reference to a chromosomal aneuploidy to refer to a gain or loss of an entire chromosome.

The term "partial" when used in reference to a chromosomal aneuploidy herein refers to a gain or loss of a portion i.e. segment, of a chromosome.

The term "enrich" herein refers to the process of amplifying polymorphic target nucleic acids contained in a portion of a maternal sample, and combining the amplified product with the remainder of the maternal sample from which the portion was removed. For example, the remainder of the maternal sample can be the original maternal sample.

The term "original maternal sample" herein refers to a non-enriched biological sample obtained from a pregnant subject e.g. a woman, who serves as the source from which a portion is removed to amplify polymorphic target nucleic acids. The "original sample" can be any sample obtained from a pregnant subject, and the processed fractions thereof e.g. a purified cfDNA sample extracted from a maternal plasma sample.

The term "primer," as used herein refers to an isolated oligonucleotide which is capable of acting as a point of initiation of synthesis when placed under conditions in which synthesis of a primer extension product, which is complementary to a nucleic acid strand, is induced (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer, use of the method, and the parameters used for primer design.

Cell Free DNA

Cell-free fetal DNA and RNA circulating in maternal blood can be used for the early non-invasive prenatal diagnosis (NIPD) of an increasing number of genetic conditions, both for pregnancy management and to aid reproductive decision-making. The presence of cell-free DNA circulating in the bloodstream has been known for over 50 years. More recently, presence of small amounts of circulating fetal DNA was discovered in the maternal bloodstream during pregnancy (Lo et al., Lancet 350:485-487 [1997]). Thought to originate from dying placental cells, cell-free fetal DNA (cfDNA) has been shown to consists of short fragments typically fewer than 200 bp in length Chan et al., Clin Chem 50:88-92 [2004]), which can be discerned as early as 4 weeks gestation (Illanes et al., Early Human Dev 83:563-566 [2007]), and known to be cleared from the maternal circulation within hours of delivery (Lo et al., Am J Hum Genet 64:218-224 [1999]). In addition to cfDNA, fragments of cell-free fetal RNA (cfRNA) can also be discerned in the maternal bloodstream, originating from genes that are transcribed in the fetus or placenta. The extraction and subsequent analysis of these fetal genetic elements from a maternal blood sample offers novel opportunities for NIPD.

In addition to its application in NIPD, numerous reports in the literature have pointed out that cell-free DNA in plasma or serum can be applied as a more specific tumor marker, than conventional biological samples, for the diagnosis and prognosis, as well as the early detection, of cancer. For instance, one study indicates that the elevation of serum cell-free DNA was usually detected in specimens containing elevated tumor markers and is most likely associated with tumor metastases. The electrophoretic pattern of cell-free DNA showed that cell-free DNA from cancer patient is fragmented, containing smaller DNA (100 bp) not found in normal cell-free DNA. Wu, et al. Cell-free DNA: measurement in various carcinomas and establishment of normal reference range. Clin Chim Acta. 2002, 321(1-2):77-87.

Baseline Process for Obtaining and Using cfDNA in Sequencing

Figure 1B:
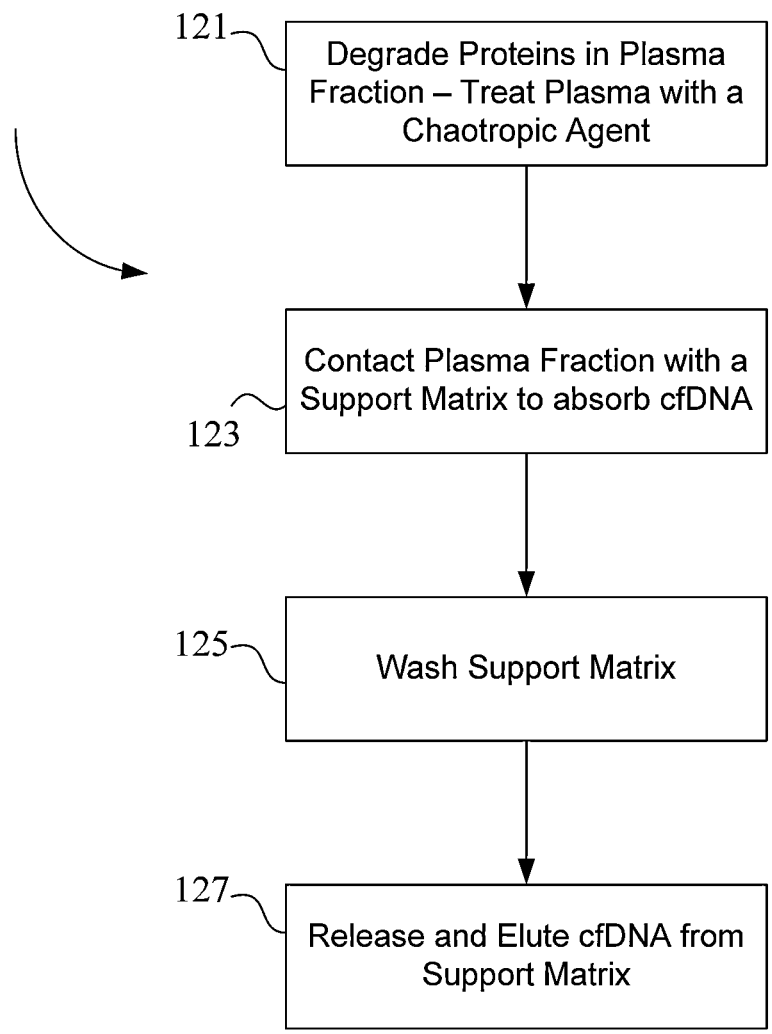
FIG. 1B shows a process of isolating cfDNA using a support matrix.

A conventional process for sequencing cfDNA is described here. It is represented in FIGS. 1A and 1B and in the bullet outline below. While the process is described for sequencing cfDNA from blood samples, many of the process steps apply in sequencing cfDNA found in other types of sample such as urine, sweat, saliva etc.

The baseline process may have the following operations:
1. collect blood with EDTA, ACD, or Streck blood collection tubes
2. centrifugations to isolate plasma fraction
    a. Low g (soft) spin to fractionate blood into plasma and other fractions (separate plasma from buffy coat and hematocrit to reduce contamination from DNA in the white blood cells)
    b. high g (hard) spin to separate additional particulates from plasma fraction
3. isolate/purify cfDNA from plasma (this is a low yield process)
    Denature and/or degrade proteins in plasma (contact with proteases) and make solution negative with guanidine hydrochloride or other chaotropic reagent (to facilitate driving cfDNA out of solution)
    Contact treated plasma with a support matrix such as beads in a column. cfDNA comes out of solution and binds to matrix.
    Wash the support matrix
    Release cfDNA from matrix and recover.
4. make a library from purified cfDNA
5. perform next generation sequencing FIG. 1A shows a conventional process for processing cfDNA using next generation sequencing. Process 100 begins with collecting a sample containing cfDNA. See operation 103 in the flow chart of FIG. 1A. Collection can be performed by any one of many available techniques. Such techniques should collect a sufficient volume of sample to supply enough cfDNA to satisfy the requirements of the sequencing technology, and account for losses during the processing leading up to sequencing.

In certain embodiments, blood is collected in specially designed blood collection tubes or other container. Such tubes may include an anti-coagulant such as ethylenediamine tetracetic acid (EDTA) or acid citrate dextrose (ACD). In some cases, the tube includes a fixative. In some embodiments, blood is collected in a tube that gently fixes cells and deactivates nucleases (e.g., Streck Cell-free DNA BCT tubes). See US Patent Application Publication No. 2010/0209930, filed Feb. 11, 2010, and US Patent Application Publication No. 2010/0184069, filed Jan. 19, 2010 each previously incorporated herein by reference.

Generally, it is desirable to collect and process cfDNA that is uncontaminated with DNA from other sources such as white blood cells. Therefore, white blood cells should be removed from the sample and/or treated in a manner that reduces the likelihood that they will release their DNA.

In the conventional process, the blood sample is centrifuged, sometimes twice. See operation 105 in FIG. 1A. The first centrifugation step produces three fractions: a plasma fraction on top, a buffy coat containing leukocytes, and hematocrit fraction on the bottom. This first centrifugation process is performed at relatively low g-force in order to avoid disrupting the leukocytes to a point where their nuclei break apart and release DNA into the plasma fraction. Density gradient centrifugation is typically used. If this first centrifugation step is performed at too high of an acceleration, some DNA from the leukocytes would likely contaminate the plasma fraction. After this centrifugation step is completed, the plasma fraction is separated from the other fractions and further processed.

After the first centrifugation is performed at relatively low g-force, a second, optional, centrifugation of the plasma fraction is performed at a higher g-force. In this step, additional particulate matter from the plasma is spun out as a solid phase and removed. This additional solid material may include some additional cells that also contain DNA that could contaminate the cell free DNA that is to be analyzed. In some embodiments, the first centrifugation is performed at an acceleration of about 1600 G and the second centrifugation is performed at an acceleration of about 16,000 G.

While a single centrifugation process from normal blood is possible, such process has been found to sometimes produce plasma contaminated with white blood cells. Any DNA isolated from this plasma will include some cellular DNA. Therefore, for cfDNA isolation from normal blood, the plasma may be subjected to a second centrifugation at high-speed to pellet out any contaminating cells as explained.

Figure 1C:
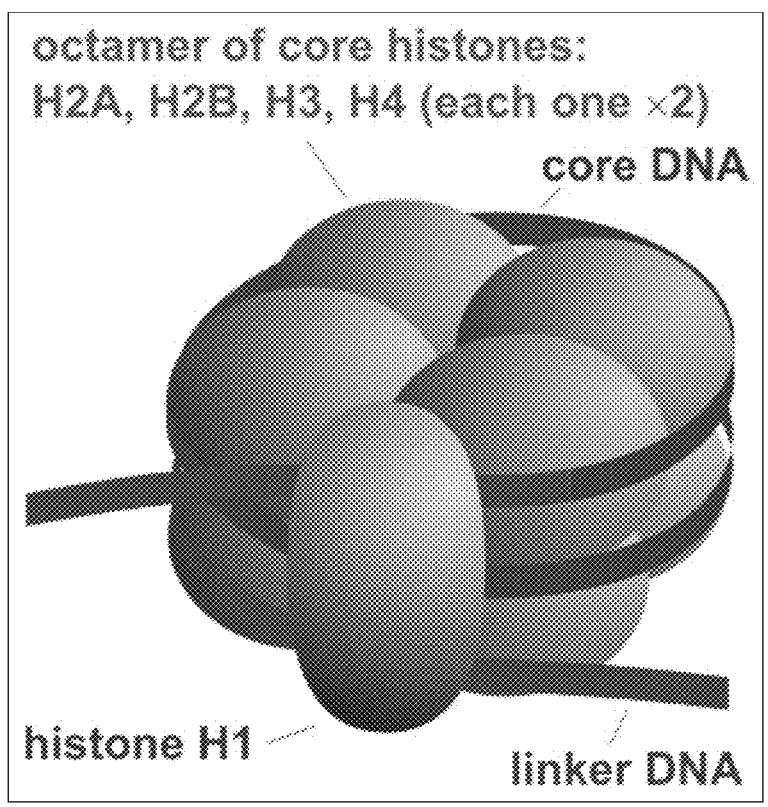
FIG. 1C illustrates the structure a nucleosome complex including a stretch of DNA wrapped around an octamer of histones.

Cell free DNA, as it exists in the plasma of an organism, is typically DNA wrapped or coiled around histone proteins. See FIG. 1C for an illustration of the structure a nucleosome complex including a stretch of DNA wrapped around an octamer of histones. Cell-free DNA in blood is apoptotic DNA that is still wrapped around nucleosomes. Nucleosomal proteins are mostly made up of positively charged histones around which the negatively charged DNA is wound. It takes approximately 147 nucleotides to wrap around a single nucleosomal protein complex, with additional bases as "linker" sequences between nucleosomal units. This explains why, upon purification, mono-nucleosomal cfDNA has a peak around 165-170 bp.

After a plasma fraction is collected as described, the cfDNA is extracted. See operation 107 of FIG. 1A and the entire flow chart of FIG. 1B. Extraction is actually a multistep process that involves separating DNA from the plasma in a column or other solid phase binding matrix.

The first part of this cfDNA isolation procedure involves denaturing or degrading the nucleosome proteins and otherwise taking steps to free the DNA from the nucleosome. See operation 121 in the flow chart of FIG. 1B. A typical reagent mixture used to accomplish this isolation includes a detergent, protease, and a chaotropic agent such as guanine hydrochloride. The protease serves to degrade the nucleosome proteins, as well as background proteins in the plasma such as albumin and immunoglobulins. The chaotropic agent disrupts the structure of macromolecules by interfering with intramolecular interactions mediated by non-covalent forces such as hydrogen bonds. The chaotropic agent also renders components of the plasma such as proteins negative in charge. The negative charge makes the medium somewhat energetically incompatible with the negatively charged DNA. The use a chaotropic agent to facilitate DNA purification is described in Boom et al., "Rapid and Simple Method for Purification of Nucleic Acids", J. Clin. Microbiology, v. 28, No. 3, 1990.

After this protein degradation treatment, which frees, at least partially, the DNA coils from the nucleosome proteins, the resulting solution is passed through a column or otherwise exposed to support matrix. See operation 123 of FIG. 1B. The cfDNA in the treated plasma selectively adheres the support matrix. The remaining constituents of the plasma pass through the binding matrix and removed. The negative charge imparted to medium components facilitates adsorption of DNA in the pores of a support matrix.

After passing the treated plasma through the support matrix, the support matrix with bound cfDNA is washed to remove additional proteins and other unwanted components of the sample. See operation 125 of FIG. 1B. After washing, the cfDNA is freed from the matrix and recovered. See operation 127 of FIG. 1B. Unfortunately, this process loses a significant fraction of the available DNA from the plasma. Generally, support matrixes have a high capacity for cfDNA, which limits the amount of cfDNA that can be easily separated from the matrix. As a consequence, the yield of cfDNA extraction step is quite low.

Typically, the efficiency is well below 50% (e.g., it has been found that the typical yield of cfDNA is 4-12 ng/ml of plasma from the available ~30 ng/ml plasma).

The purified cfDNA is used to prepare a library for sequencing. See operation 109 of FIG. 1A. To sequence a population of double-stranded DNA fragments using massively parallel sequencing systems, the DNA fragments must be flanked by known adapter sequences. A collection of such DNA fragments with adapters at either end is called a sequencing library. Two examples of suitable methods for generating sequencing libraries from purified DNA are (1) ligation-based attachment of known adapters to either end of fragmented DNA, and (2) transposase-mediated insertion of adapter sequences. There are many suitable massively parallel sequencing techniques. Some of these are described below. The sequencing operation is depicted in block 111 of FIG. 1A.

Efficiently Producing cfDNA Libraries

Unless indicated otherwise, details of the operations described above for a conventional process can be applied for comparable operations employed in the following embodiments.

Generating Library Directly, without Purifying cfDNA (Direct Generation of Library from Plasma FT Supernatant)

The embodiments described in this section involve making cfDNA sequencing libraries from biological fluids without first purifying the DNA from such fluids. A typical cfDNA concentration in biological fluids is approximately 30 ng/ml of plasma. Between this low starting DNA concentrations and the small size of cfDNA (~170 bp), the efficiency of DNA isolation is poor (significantly less than 50% yield). It has been found, for example, that the typical yield of cfDNA is 4-12 ng/ml of plasma from the available ~30 ng/ml plasma. The direct method described here can greatly increase the yield.

Examples of processes for generating a library directly from plasma, without first purifying DNA, are presented in the outline immediately below and in the flow charts of FIGS. 2A and 2B.

1. collect blood—optionally with a fixative (Any fixative that prevents release of cellular DNA would be useful; e.g., Streck.)
2. centrifugations to isolate plasma (in some implementations, only the hard centrifugation is needed if a fixative is used—the fixative binds white blood cell DNA to the nucleii, preventing it from contaminating the plasma fraction used for its cfDNA.)
    separate plasma from other components (e.g., buffy coat and hematocrit in a soft spin) to reduce contamination from maternal DNA
    option—use a "freeze-thaw" supernatant produced as described below.
3. make a library directly from cfDNA existing in plasma or freeze-thaw supernatant without first purifying the cfDNA from these sources.
    Condition 1—loosen cfDNA wrapped around histones to allow end of cfDNA strand to become available for ligating an adaptor. (mild detergent and/or mild heat)
    Condition 2—Do so under conditions that do not harm ligase or transposase (no aggressive proteases and no guanidine hydrochloride)—ligation requires four components: cfDNA, adaptor sequences, ligase, ATP.
    Condition 3—reduce concentration of background serum proteins (immunoglobulins and albumin)—one embodiment: pass plasma over a column or other container of a support matrix. Simple conditions—possibly remove only a fraction of the protein (50% or 75% or 80% or 90%).
4. perform next generation sequencing One benefit of directly generating a library is a significantly higher cfDNA recovery rate than is attainable with a conventional process. A second benefit is a simplification of the process by replacing the multi-step DNA isolation procedure with a simple one or two-step process that provides a library of DNA for sequencing. In the conventional technique, the relevant steps are: degrading serum and nucleosome proteins, contacting the solution with a DNA-absorbing support matrix, washing the support matrix, eluting the DNA from the support matrix, and attaching adapters to the isolated DNA. In contrast, the direct library generation method includes the following steps: removing some fraction of the serum proteins, and attaching adapters to the ends of the cfDNA in the resulting solution.

Figure 2A:
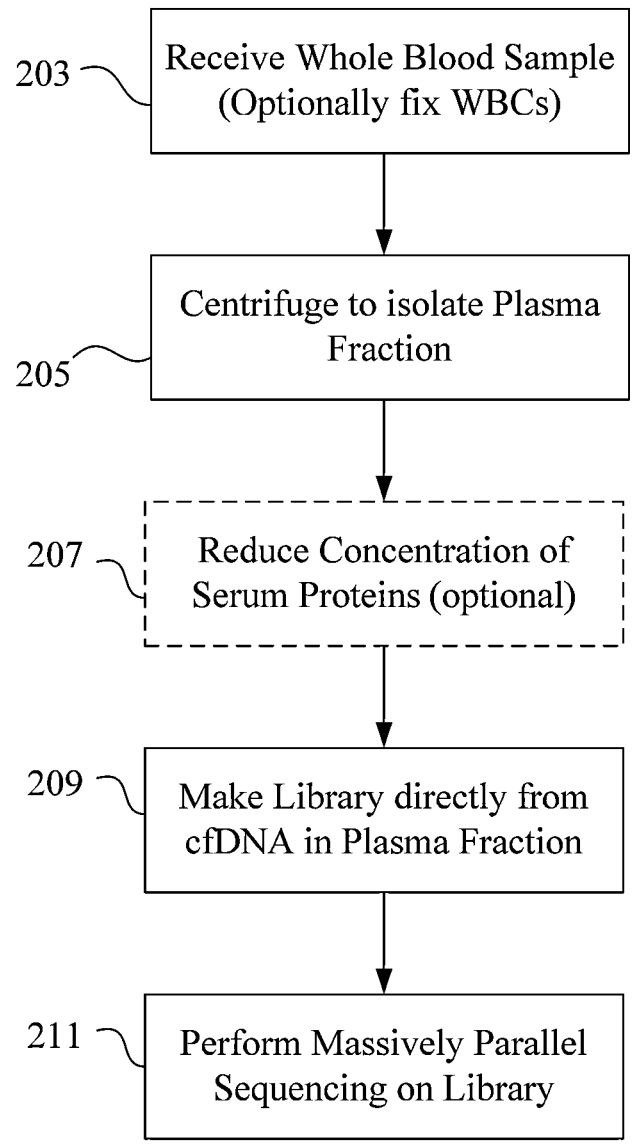
FIG. 2A shows a process for sample preparations for massively parallel sequencing using sequencing library prepared directly from cfDNA in plasma.
Figure 2B:
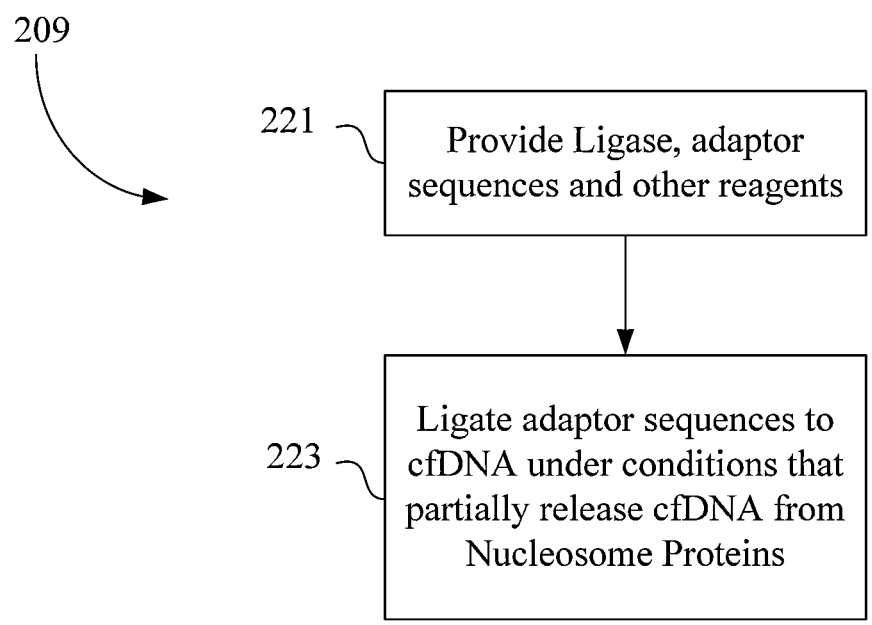
FIG. 2B shows the operations involved in making the sequence library.

Turning to FIG. 2A, the depicted process begins with receipt of a whole blood sample. This is indicated by block 203 of the Figure. This operation may be performed as described above for the conventional process. In some cases, the whole blood is treated with a fixing agent to stabilize the cells in the sample, and thereby reduce the likelihood that their DNA will contaminate the cfDNA used to make a library.

Additionally, the blood sample may be treated to deactivate nucleases. Most nucleases can be deactivated by heating the plasma (e.g., to about 65° C. for about 15-30 minutes) or by contacting the sample with a nuclease inhibitor. In one example, the sample is provided in a blood collection tube such as a tube sold for this purpose by Streck, Inc., which includes an additive that deactivates nucleases. Examples of compositions having nuclease inhibiting activity are disclosed in US Patent Application Publication 2010/0184069, filed Jan. 19, 2010, and in US Patent Application Publication No. 2010/209930, filed Feb. 11, 2010, both previously incorporated herein by reference.

The sample collected in operation 203 is centrifuged to generate a plasma fraction containing the cfDNA that is carried forward in the process. See operation 205. In certain embodiments, only a single centrifugation step is performed, as compared to the conventional process where two centrifugation steps are performed. The second centrifugation step may be eliminated when the white blood cells in the sample are stabilized by fixative or other reagent, so that they do not release their nuclear DNA when exposed to high g-forces. When this is done, a single, high g-force centrifugation step may be employed to remove all cells from the whole blood. The leukocytes that have been stabilized are better able to withstand the forces experienced during this step. A greater fraction of the cfDNA in the sample is recovered in the plasma fraction when a single centrifugation step is performed.

In the direct method described here, the native cfDNA coiled around nucleosome proteins may be used as such, without first isolating it as required in the conventional processes described above. As mentioned, cfDNA used in a library must have adapters attached to both ends of the DNA strands. In some cases, these adaptor sequences are about 30-100 bp in length, e.g., about 60 bp. In the conventional process, adaptor ligation is accomplished only after the cfDNA has been uncoiled and removed from the nucleosome proteins. In the direct process, in contrast, the adapters are attached while the cfDNA is still coiled around nucleosome proteins.

Two suitable methods for generating sequencing libraries from purified DNA are (1) ligation-based attachment of known adapters to either end of fragmented DNA and (2) transposase-mediated insertion of adapter sequences. Both of these processes may be performed directly on cfDNA that is wound around nucleosomes in biological fluids.

To attach adaptor sequences to cfDNA still bound to nucleosome proteins, it may be necessary to first reduce the concentration of serum proteins. Further, it may be necessary to conduct an attachment reaction under conditions that loosen the cfDNA from the nucleosome proteins.

The adaptor ligation reaction requires four interacting components: adapter sequences, cfDNA, a ligase, and ATP, the energy source required to drive the ligation reaction. The transposase reaction requires similar components. Plasma has a large amount of ambient protein, predominantly 35-50 mg/ml albumin and 10-15 mg/ml immunoglobulins (Igs). These proteins create steric hindrance for the library-making components to act on nucleosomal cfDNA. In other words, plasma from the sample will have perhaps too much background proteins such as albumin and immunoglobulins to allow adaptor attachment to proceed efficiently. Therefore, methods for removing serum proteins or at least reducing their concentration may be employed. See optional step 207 of FIG. 2A. Such methods may involve passing the plasma over a support matrix that selectively binds proteins but has little or no affinity for the DNA. In some embodiments, serum protein can be depleted using a combination of albumin and immunoglobulin depletion columns.

A separation procedure for removing proteins can be relatively simple compared to the DNA isolation procedure which requires contact of the serum to a DNA absorbing support matrix followed by washing and eluting of the DNA. To remove proteins, the current procedure merely involves passing the plasma over a support matrix which absorbs for serum proteins. No washing or elution is required.

An alternative method to reducing serum proteins employs a protease that can be removed, degraded and/or deactivated before performing the adaptor attachment reaction. For example, a heat labile protease may be used. This is one that will deactivate at a temperature well below the temperature that degrades the cfDNA. For example, a protease that deactivates at a temperature of about 95° C. or lower, or about 70° C. or lower, is used in some embodiments. After treating the plasma or freeze-thaw supernatant with such protease, the sample temperature is raised to a level that deactivates the protease. Thereafter, the sample is optionally centrifuged or otherwise processed to remove the degraded serum protein. Certain other embodiments employ a metalloprotease or other protease requiring a metal ion or cofactor to activate its proteolytic function. In such cases, the sample is contacted with the protease in its active form for a period sufficient to degrade some or all of the serum proteins. Then, the protease is deactivated by removing the metal ion or other cofactor. In the cases of a metalloprotein, this may be accomplished by contacting the sample with a chelating agent such as EDTA. Thereafter, the degraded serum protein is optionally removed and the adaptor attachment reaction is performed.

As mentioned, the cfDNA from the sample is converted to a library without first separating the DNA from the sample. See operation 209 of FIG. 2A and both operations of FIG. 2B. In other words, the cfDNA is used in the sample or a portion of the sample in which the cfDNA naturally exists (e.g., the plasma or other liquid fraction of whole blood). In the process of attaching adaptors, the necessary reactants are contacted with the sample portion containing the cfDNA. In the case of ligation, these are a ligase, ATP, and adaptors. See operation 221 of FIG. 2B. Additionally, during the reaction, the cfDNA, specifically the "ends" of cfDNA, may be made more accessible to library preparation enzymes by certain techniques. See operation 223 of FIG. 2B.

Helically wrapped nucleosomal DNA spontaneously becomes accessible to cellular proteins such as RNA polymerase. See, Li et al., *Rapid spontaneous accessibility of nucleosomal DNA*, Nature Structural and Molecular Biology, 12, 1, Jan. 2005. However, to make the cfDNA sufficiently accessible for adaptor ligation while still attached to nucleosome proteins, the process may expose the protein bound cfDNA to conditions that increase the entropy of the nucleosome-cfDNA complex and allow the ends of the coiled DNA to become free of the histones more frequently and/or for longer durations and therefore become available for ligation during a greater fraction of the time. This loosening of the cfDNA should be accomplished in a way that does not interfere with the litigation process. As such, the process should generally avoid using proteases or chaotropic agents such as are used in the conventional isolation process. Proteases which denature or otherwise degrade proteins in plasma would interfere with the action of ligase and could only be destroyed at high temperatures which would also destroy the cfDNA.

To promote loosening of the cfDNA, the process may employ a slightly elevated temperature and or the use of mild detergents. For example, the process may be conducted at a temperature of between about 30 and 75° C., or between about 35 and 45° C., or between about 45 and 55° C., or between about 55 and 65° C., or between about 65 and 75° C.

In some embodiments, adaptor attachment is performed using mild detergents and salts (or combinations thereof). When chosen correctly, these will cause the cfDNA to unwrap from the histone complex, at least slightly, allowing access to the ends of the cfDNA for ligation of the sequencing adapters. If a detergent is used, it should be sufficiently mild that it does not interfere with the ligation process. Sodium dodecyl sulfate is likely too aggressive for most applications. In other words, it should not disrupt or denature the ligase. Examples of suitable types of detergents include various non-ionic detergents. One example of detergent that has been found suitable is TWEEN®-20 (polysorbate-20).

After, the library is prepared, it sequenced by, e.g., a massively parallel sequencing technique. Additional proteins remaining in the sample after library generation (including histones) are degraded by the heating step in the first cycle of amplification (e.g., PCR), which is performed as an initial part of the sequencing process.

In some embodiments, adaptors are introduced into target DNA using transposase-mediated methods. See, Adey et al., *Rapid, low-input, low-bias construction* of shotgun fragment libraries by high *-density in vitro transposition*, Genome Biology 2010, 11:R119. As an example, a Tn5 transposase derivative may be used integrate adaptor sequences into cfDNA. The derivative comprises wild-type Tn5 transposon DNA is flanked by two inverted IS50 elements, each containing two 19 bp sequences required for function (outside end and inside end). A 19 bp derivative allows transposition provided that the intervening DNA is long enough to allow the two ends to come in close proximity in order to form a complex with a Tn5 transposase homodimer.

In summary, the direct processing of cell free DNA in plasma, the method eliminates the need to pass the plasma through a column or other vessel containing a support matrix. DNA is therefore not isolated on a support matrix. This greatly increases the amount of DNA that is recovered from the original blood sample. It also reduces the complexity of the process. In some embodiments, another significant difference from the conventional process is the lack of a step of degrading nucleosomal proteins with a protease or other agent. Typically, the adaptor attachment reaction is performed in a medium containing a significant fraction of the original sample (e.g., whole blood, urine, sweat, etc.). Examples of such fractions include plasma and freeze-thaw supernatant.

To realize these benefits, the direct process addresses the challenges introduced by salts, proteases, nucleases, albumin, and immunoglobulins, all present in plasma, which can interfere with the library biochemistry. Therefore, in working with plasma cfDNA directly, the process may (1) reduce the concentration of background albumins and Igs, (2) inhibit or remove proteases and nucleases, and/or (3) render the cfDNA ends more accessible.

Freeze Thaw Method (cfDNA Purification from Thawed Supernatant)

Figure 3A:
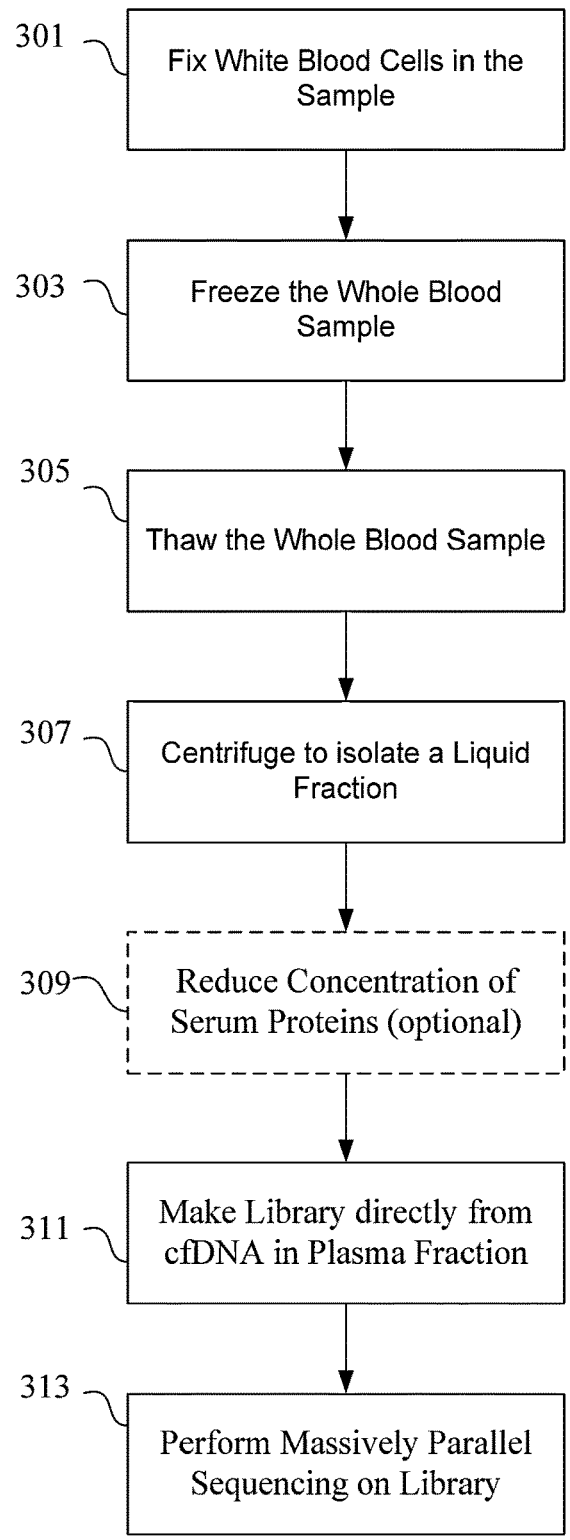
FIGS. 3A and 3B show processes for massively parallel sequencing using sequencing library prepared directly from cfDNA in plasma, the process involving freezing and thawing. The process of FIG. 3A does not require isolation of cfDNA from plasma, while the process of FIG. 3B does.
Figure 3B:
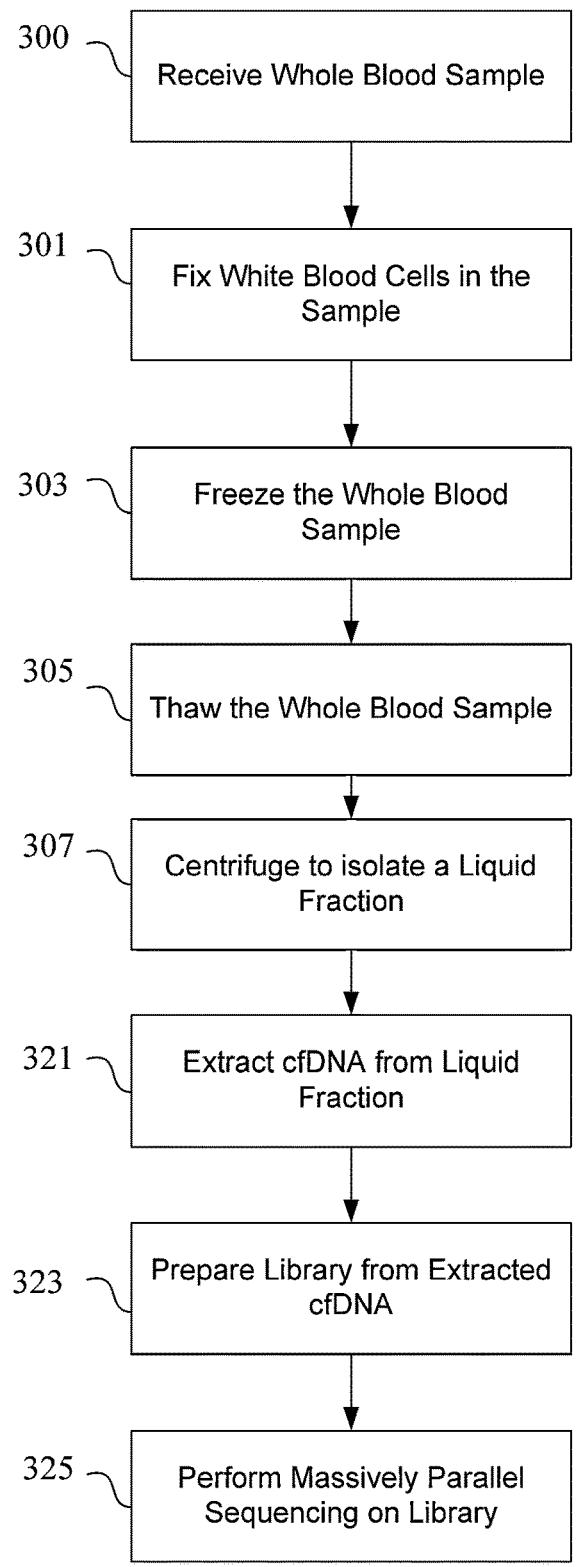

An alternative process for preparing sequencing libraries is depicted in FIGS. 3A and 3B and the outline that immediately follows.

1. Collect whole blood with a fixative (Any fixative that prevents release of cellular DNA from the nucleus may be used)
2. Freeze and later thaw the whole blood (the whole blood may be frozen in a tube lying on its side to prevent breakage during freezing)—The freezing destroys the cell membranes and possibly modifies serum proteins so that they come out of blood more easily.
3. Centrifuge to remove solids
    a single high g (hard) spin is all that is needed so long as the WBC DNA is fixed to the nuclei.
    The supernatant is red (has hemoglobin) and of quite low viscosity compared to whole blood. The freeze thaw may reduce the concentration of serum proteins and thereby reduce viscosity.
4. Optional A—isolate cfDNA from supernatant (conventional technique—see papers)
    Optional—Size selection to remove putative cell-bound DNA originating, e.g., white blood cells. (As an example, select DNA of size 800 bps and smaller)
    make a library from cfDNA (conventional technique described above)
4. Option B—directly make library from the supernatant using the procedure in the direct method.
    Optional—Size selection to remove putative maternal DNA originating in cells.

5. Perform next generation sequencing

This method can be used with either conventional cfDNA isolation procedure or with a procedure that produces a DNA library directly from blood or plasma. The second procedure is as described above for the direct method.

Typically, the process begins by receiving a whole blood sample (operation 300) followed by fixing the white blood cells in the sample (operation 301). Suitable fixing agents include those described above. Additionally, the whole blood sample may be treated with nuclease inhibitors. These are also described above. The fixing process should bind white blood cell DNA to the cells' nuclei, or at least inhibit DNA release from the nuclei during centrifugation.

As illustrated in FIGS. 3A and 3B, the whole blood sample is frozen. See operation 303. Freezing is believed to destroy the constituent cells by breaking their cell membranes and otherwise disrupting their cell structure. Certain of the cellular organelles may remain intact. These include the nuclei of the cells, particularly if an appropriate fixing agent is used. The freezing may also modify the structure of the serum proteins so that they more readily come out of the plasma.

Freezing may be performed directly on whole blood. No other processing is required aside from the previously mentioned fixing and nuclease inhibition. Freezing may be conducted in sample collection tubes or other collection vehicle. Preferably, the process is conducted in a manner that resists breaking of the collection vehicle as the sample expands. A large expansion surface area to volume is desired. In some embodiments, sample tubes are positioned on their sides during freezing. This provides significantly greater expansion surface area than is available when tubes sit upright.

Freezing may be accomplished by any suitable procedure, so long as it effectively disrupts the cells in the sample. Freezing in conventional freezing apparatus is suitable. As examples, the freezing temperature may be about −20° C. or lower, or about −70° C. or lower, or about −70° C. to −120° C.

After the sample has been frozen, it is thawed. See operation 305 of FIGS. 3A and 3B. The sample may remain frozen for any period of time before thawing. In some embodiments, the sample is thawed by immersing in a liquid bath such as a water bath at room temperature. In certain embodiments, the bath temperature is between about 10° C. and 37° C.

The thawed blood includes the remnants of the original blood which have been disrupted by the freezing. It is believed that the thawed blood contains liquid containing much of the cfDNA from the original whole blood sample, but without contamination from cellular DNA. In the processes of FIGS. 3A and 3B, the thawed blood is subjected to a single hard spin centrifugation to separate the sample into a solid phase and a supernatant. See operations 307. The supernatant may be a low viscosity red colored material. It is believed that it contains cfDNA, hemoglobin and some fraction of the original serum proteins. The solid fraction includes organelles and other materials from the freeze-disrupted red blood cells white blood cells, and including relatively intact nuclei of the white blood cells. The solids are removed. Therefore, the supernatant includes much of the cfDNA from the sample, typically without contaminating DNA from white blood cells. The DNA from the white blood cells is included in the solid fraction of has been removed.

It has been found that a rather high fraction of the whole blood is available in the supernatant. As mentioned, the supernatant contains cfDNA that is typically free of DNA from the nuclei of the white blood cells. CfDNA resides not only in the plasma fraction of a conventionally centrifuged blood sample but also in the hematocrit and buffy coat fractions. However, in the conventional process, the hematocrit and buffy coat are discarded because they are likely contaminated with DNA from other sources within the blood. As an example, for 8 mL of whole blood sample, roughly 7 mL of thawed supernatant is recovered. In a conventional, non-freeze-thaw process, only about 3 mL of plasma is recovered from 8 mL of whole blood sample. Therefore the current process employs a single operation, performed on the thawed blood, to produce a blood fraction having a relatively high retained fraction of the cfDNA from the original sample. The freeze-thaw method may greatly increase the recovery of cfDNA and a whole blood sample.

It is been observed that the viscosity of the supernatant is significantly lower than that of whole blood. It is believed that the freezing disrupts the proteins in the serum so that they are more easily removed from the serum fraction, possibly by simple centrifugation.

The supernatant can be processed to isolate cell free DNA according to the conventional protocol. This is depicted in FIG. 3B. Alternatively, the supernatant can be processed to directly to ligate adapters onto cell free DNA in the manner described above. This is depicted in FIG. 3A.

In certain embodiments, the DNA in the supernatant is subjected to size selection to remove high molecular weight DNA that possibly originates from white blood cells. Size selection is performed after centrifugation but before adaptor attachment. In some embodiments, it is performed in conjunction with a serum protein removing step. In certain embodiments, DNA having a size of about 1000 bp or greater is excluded, or a size of about 800 bp or greater is excluded, or a size of about 500 bp or greater is excluded. Various size selection procedures may be employed. Some of these employ a volume excluding agent such as polyethylene glycol (PEG6000 or PEG8000) and a salt (e.g., NaCl). The concentrations of the agent and salt dictate the size of DNA that is selected. In some cases, the size selection process takes advantage of the fact that nucleosomes are relatively small compact structures, often nominally spherical, that pass through size selection media more easily than long strands of DNA and other biomolecules. An example of suitable size selection procedure is described in Hawkins et al, "DNA purification and isolation using a solid-phase", *Nucleic Acid Research*, Vol. 22, No. 21, pp. 4543-44 (1994). A commercially available product for size selection is the SPRIselect Reagent Kit (Beckman Coulter).

Among the advantages of the freeze-thaw process that may be realized are the following:
 (1) decreased handling of the blood
 (2) larger numbers of aliquots of the FT (freeze-thaw) Blood will be available for downstream work
 (3) the concentrations of cfDNA isolated from FT Blood are typically higher.

Samples Sources

While whole blood has been discussed as the sample source in most of the disclosed embodiments, the methods herein may be used with many different sample sources. In certain embodiments, the sample comprises a tissue sample, a biological fluid sample, a cell sample, and the like. Suitable biological fluid samples include, but are not limited to whole blood, a blood fraction, plasma, serum, sweat, tears, sputum, urine, sputum, ear flow, lymph, saliva, cerebrospinal fluid, ravages, bone marrow suspension, vaginal flow, transcervical lavage, brain fluid, ascites, milk, secretions of the respiratory, intestinal and genitourinary tracts, amniotic fluid, milk, pleural fluid, pericardial fluid, peritoneal fluid, and leukophoresis samples. In some embodiments, the sample is a sample that is easily obtainable by non-invasive procedures e.g. blood, plasma, serum, sweat, tears, sputum, urine, sputum, ear flow, saliva or feces. In certain embodiments the sample is a peripheral blood sample, or the plasma and/or serum fractions of a peripheral blood sample. In other embodiments, the biological sample is a swab or smear, a biopsy specimen, or a cell culture. In other embodiments, the biological sample is a stool (fecal) sample.

In some embodiments, the sample is a mixture of two or more biological samples e.g. a biological sample can comprise two or more of a biological fluid sample, a tissue sample, and a cell culture sample. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

The sample comprising the nucleic acid(s) to which the methods described herein are applied typically comprises a biological sample ("test sample"), e.g., as described above. In conventional methods, the nucleic acid(s) to be screened for one or more CNVs is purified or isolated by any of a number of well-known methods. In some embodiments of the current disclosure, the processes can omit one or more steps involved in the purification or isolation of the nucleic acid(s).

In some embodiments it is advantageous to obtain cell-free nucleic acids e.g. cell-free DNA (cfDNA). Cell-free nucleic acids, including cell-free DNA, can be obtained by various methods known in the art from biological samples including but not limited to plasma, serum, and urine (see, e.g., Fan et al., *Proc Natl Acad Sci* 105:16266-16271 [2008]; Koide et al., *Prenatal Diagnosis* 25:604-607 [2005]; Chen et al., *Nature Med.* 2: 1033-1035 [1996]; Lo et al., Lancet 350: 485-487 [1997]; Botezatu et al., Clin Chem. 46: 1078-1084, 2000; and Su et al., J. Mol. Diagn. 6: 101-107 [2004]). To separate cell-free DNA from cells in a sample, various methods including, but not limited to fractionation, centrifugation (e.g., density gradient centrifugation), DNA-specific precipitation, or high-throughput cell sorting and/or other separation methods can be used. Commercially available kits for manual and automated separation of cfDNA are available (Roche Diagnostics, Indianapolis, Ind., Qiagen, Valencia, Calif., Macherey-Nagel, Duren, Del.). Biological samples comprising cfDNA have been used in assays to determine the presence or absence of chromosomal abnormalities e.g. trisomy 21, by sequencing assays that can detect chromosomal aneuploidies and/or various polymorphisms.

In certain embodiments, samples can be obtained from sources, including, but not limited to, samples from different individuals, samples from different developmental stages of the same or different individuals, samples from different diseased individuals (e.g., individuals with cancer or suspected of having a genetic disorder), normal individuals, samples obtained at different stages of a disease in an individual, samples obtained from an individual subjected to different treatments for a disease, samples from individuals subjected to different environmental factors, samples from individuals with predisposition to a pathology, samples individuals with exposure to an infectious disease agent (e.g., HIV), and the like.

In one illustrative, but non-limiting embodiment, the sample is a maternal sample that is obtained from a pregnant female, for example a pregnant woman. The maternal sample comprises a mixture of fetal and maternal DNA e.g. cfDNA. In this instance, the sample can be analyzed using the methods described herein to provide a prenatal diagnosis of potential chromosomal abnormalities in the fetus. The maternal sample can be a tissue sample, a biological fluid sample, or a cell sample. In some embodiments, the maternal sample is a biological fluid sample e.g. a blood sample, a plasma sample, a serum sample, a urine sample, a saliva sample. Other maternal samples include any of the biological fluid samples disclosed elsewhere herein.

In another illustrative, but non-limiting embodiment, the maternal sample is a mixture of two or more biological samples e.g. the biological sample can comprise two or more of a biological fluid sample, a tissue sample, and a cell culture sample.

Collection of Samples for cfDNA Sequencing

Samples can be collected using any of a number of various different techniques. Techniques suitable for individual sample types will be readily apparent to those of skill in the art. For example, whole blood may be collected in tubes such as standard color-coded blood collection tubes containing anticoagulants (lithium heparin, etc.), chelating agents (EDTA, etc.), nuclease and/or protease inhibitors, etc. As mentioned above Cell-Free DNA BCT™ tubes available from Streck, Inc. are suitable for some applications described herein.

Figure 4:
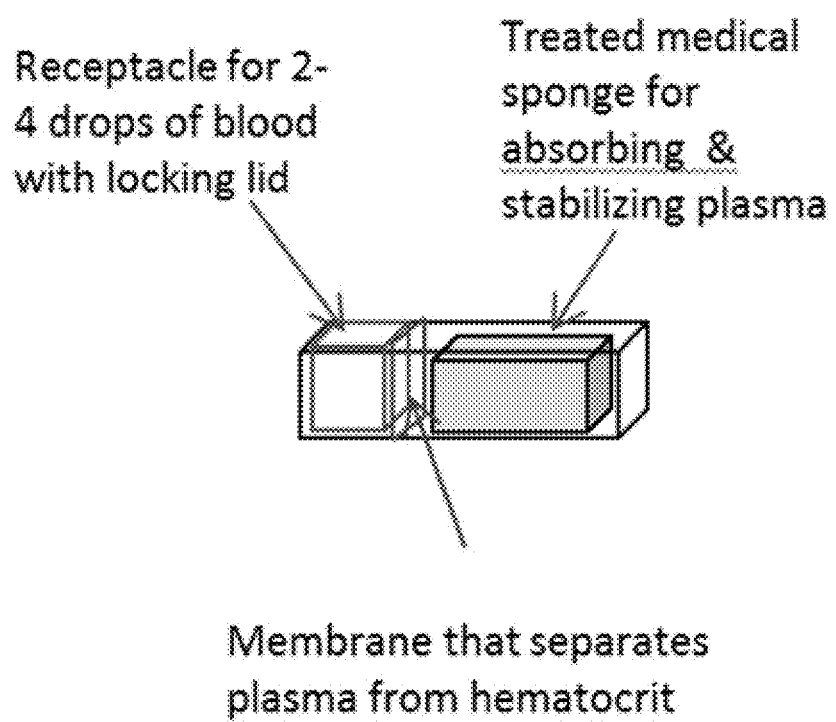
FIG. 4 below presents an example of another suitable device for collecting whole blood.

FIG. 4 below presents an example of another suitable device for collecting whole blood. As explained above, plasma constitutes roughly 50% v/v of whole blood. A version of a small depicted device that collects 2-4 drops of patient/donor blood (100-200 ul) and then separates the plasma from the hematocrit using a specialized membrane. The device can be used to generate the required 50-100 ul of plasma for NGS library preparation. Once the plasma has been separated by the membrane, it can be absorbed into a pretreated medical sponge. In certain embodiments, the sponge is pretreated with a combination of preservatives, proteases and salts to (a) inhibit nucleases and/or (b) stabilize the plasma DNA until downstream processing. Products such as Vivid Plasma Separation Membrane (Pall Life Sciences, Ann Arbor, Mich.) and Medisponge 50PW (Filtrona technologies, St. Charles, Mo.) can be used.

The plasma DNA in the medical sponge can be accessed for NGS library generation in a variety of ways:

(a) Reconstitute and extract that plasma from the sponge and isolate DNA for downstream processing. Of course, this approach may have limited DNA recovery, efficiency.

(b) Utilize the DNA-binding properties of the medical sponge polymer to isolate the DNA (c) Conduct direct PCR-based library preparation using the DNA that is bound to the sponge. This may be conducted using any of the cfDNA library preparation techniques described above.

Sequencing Library Preparation

In one embodiment, the methods described herein can utilize next generation sequencing technologies that allow multiple samples to be sequenced individually as genomic molecules (i.e. singleplex sequencing) or as pooled samples comprising indexed genomic molecules (e.g., multiplex sequencing) on a single sequencing run. These methods can generate up to several hundred million reads of DNA sequences. In various embodiments the sequences of genomic nucleic acids, and/or of indexed genomic nucleic acids can be determined using, for example, the Next Generation Sequencing Technologies (NGS) described herein. In various embodiments analysis of the massive amount of sequence data obtained using NGS can be performed using one or more processors as described herein.

As explained, a whole blood sample may be processed to provide a plasma fraction containing cfDNA that has reduced binding with, but not fully uncoiled from, nucleosomal proteins. In some embodiments, a plasma fraction containing such cfDNA may then be provided to a droplet actuator as described below. The droplet applicator causes a droplet to coagulate. The coagulated portion including cfDNA may then be provided as an input to assays of next generation sequencing. In some embodiments, the assays use ligation or transposon-mediated insertion to attach adaptors or tags to the cfDNA, to prepare sequencing libraries.

In some embodiments, samples containing cfDNA may be processed as droplets using a droplet actuator, which allows processing of very small amount of samples using microfluidic devices. PCT Patent Application Publication No. WO 2009/135205 describes examples of such droplet actuators, which is incorporated by reference in its entirety. In some embodiments, a droplet actuator has two substrates separated by a droplet operation gap, each substrate associated with operation electrodes. The droplet operation gap is occupied by a filler fluid typically comprising an organic oil. In some embodiments, a blood sample, either whole blood or a blood component such as plasma, can be provided in small quantity to form a source droplet in a filler fluid. Then the droplet actuator causes the source droplet to coagulate to form a coagulated portion and a supernatant. The coagulation may be effected by applying a procoagulant, heating, cooling, or electric field, etc. Then the coagulated portion may be used as an input into assays for further downstream processing to obtain sequencing libraries.

An example of sequencing library preparation is described in U.S. Patent Application Publication No. US 2013/0203606, which is incorporated by reference in its entirety. In some embodiments, this preparation may take the coagulated portion of the sample from the droplet actuator as an assay input. The library preparation process is a ligation-based process, which includes four main operations: (a) blunt-ending, (b) phosphorylating, (c) A-tailing, and (d) ligating adaptors. DNA fragments in a droplet are provided to process the sequencing library. In the blunt-ending operation (a), nucleic acid fragments with 5'- and/or 3'-overhangs are blunt-ended using T4 DNA polymerase that has both a 3'-5' exonuclease activity and a 5'-3' polymerase activity, removing overhangs and yielding complementary bases at both ends on DNA fragments. In some embodiments, the T4 DNA polymerase may be provided as a droplet. In the phosphorylation operation (b), T4 polynucleotide kinase may be used to attach a phosphate to the 5'-hydroxyl terminus of the blunt-ended nucleic acid. In some embodiments, the T4 polynucleotide kinase may be provided as a droplet. In the A-tailing operation (c), the 3' hydroxyl end of a dATP is attached to the phosphate on the 5'-hydroxyl terminus of a blunt-ended fragment catalyzed by exo-Klenow polymerase. In the ligating operation (d), sequencing adaptors are ligated to the A-tail. T4 DNA ligase is used to catalyze the formation of a phosphate bond between the A-tail and the adaptor sequence. In some embodiments involving cfDNA, end-repairing (including blunt-ending and phosphorylation) may be skipped because the cfDNA are naturally fragmented, but the overall process upstream and downstream of end repair is otherwise comparable to processes involving longer strands of DNA.

In some embodiments, instead of using ligation to introduce tags for a sequencing library prepared from cfDNA, extension or insertion may be used instead of or in addition to ligation. U.S. Patent Application Publication No. 2010/0120098, incorporated by reference in its entirety, provides exemplary processes that may use transposon-mediated insertion to introduce tags to cfDNA. In some embodiments, the cfDNA are unpurified cfDNA obtained by processes described above. In the context of the publication, a transposon is a genetic element that changes location in a genome through a transposition reaction catalyzed by a transposase. A transposon end is a double-stranded DNA consisting of the minimum number of nucleotides required to couple with a transposase to form a transposome, which drives transposition. A transposon end containing composition is a double-stranded DNA containing a transposon end at the 3' end and other sequence elements or tags at the 5' end (e.g., sequencing adaptors or unique identifiers for assays). The transposon end and transposon end containing composition each have a transferred strand and a non-transferred strand complementary to the transferred strand, wherein the transferred strand is inserted into the target sequence by linking the 3' end of the transposon end sequence to the 5' end of the target sequence. The non-transferred strand is not directly transferred to the target sequence. The publication provides methods suitable for preparing a sequence library from nucleic acids, including cfDNA. One embodiment involves tagging both ends of a fragment of a target DNA (e.g. a cfDNA fragment), which constitutes a fragment in a sequencing library. The method involves incubating a fragment of a target DNA, a transposase (e.g. Tn5 transposase or Mu transposase), and a transposon end containing composition, thereby allowing a transposition reaction catalyzed by the transposase. The transposition reaction inserts a transferred strand into the target DNA fragment by ligating the transposon end of the transferred strand to the 5' end of the target sequence, thereby providing a 5' tagged target DNA fragment. The method further involves incubating the 5' tagged target DNA fragment with a nucleic acid modifying enzyme (e.g., a polymerase or a ligase), thereby joining a 3' tag to a 3' end of the 5' tagged target DNA fragment. The process yields a di-tagged target DNA, which may be further processed to produce sequencing libraries as described further below.

In various embodiments the use of such sequencing technologies does not involve the preparation of sequencing libraries.

However, in certain embodiments the sequencing methods contemplated herein involve the preparation of sequencing libraries. In one illustrative approach, sequencing library preparation involves the production of a random collection of adapter-modified DNA fragments (e.g., polynucleotides) that are ready to be sequenced. Sequencing libraries of polynucleotides can be prepared from DNA or RNA, including equivalents, analogs of either DNA or cDNA, for example, DNA or cDNA that is complementary or copy DNA produced from an RNA template, by the action of reverse transcriptase. The polynucleotides may originate in double-stranded form (e.g., dsDNA such as genomic DNA fragments, cDNA, PCR amplification products, and the like) or, in certain embodiments, the polynucleotides may originated in single-stranded form (e.g., ssDNA, RNA, etc.) and have been converted to dsDNA form. By way of illustration, in certain embodiments, single stranded mRNA molecules may be copied into double-stranded cDNAs suitable for use in preparing a sequencing library. The precise sequence of the primary polynucleotide molecules is generally not material to the method of library preparation, and may be known or unknown. In one embodiment, the polynucleotide molecules are DNA molecules. More particularly, in certain embodiments, the polynucleotide molecules represent the entire genetic complement of an organism or substantially the entire genetic complement of an organism, and are genomic DNA molecules (e.g., cellular DNA, cell free DNA (cfDNA), etc.), that typically include both intron sequence and exon sequence (coding sequence), as well as non-coding regulatory sequences such as promoter and enhancer sequences. In certain embodiments, the primary polynucleotide molecules comprise human genomic DNA molecules, e.g. cfDNA molecules present in peripheral blood of a pregnant subject.

Preparation of sequencing libraries for some NGS sequencing platforms is facilitated by the use of polynucleotides comprising a specific range of fragment sizes. Preparation of such libraries typically involves the fragmentation of large polynucleotides (e.g. cellular genomic DNA) to obtain polynucleotides in the desired size range.

Fragmentation can be achieved by any of a number of methods known to those of skill in the art. For example, fragmentation can be achieved by mechanical means including, but not limited to nebulization, sonication and hydroshear. However mechanical fragmentation typically cleaves the DNA backbone at C—O, P—O and C—C bonds resulting in a heterogeneous mix of blunt and 3'- and 5'-overhanging ends with broken C—O, P—O and/C—C bonds (see, e.g., Alnemri and Liwack, J. Biol. Chem 265:17323-17333 [1990]; Richards and Boyer, J Mol Biol 11:327-240 [1965]) which may need to be repaired as they may lack the requisite 5'-phosphate for the subsequent enzymatic reactions e.g. ligation of sequencing adaptors, that are required for preparing DNA for sequencing.

In contrast, cfDNA, typically exists as fragments of less than about 300 base pairs and consequently, fragmentation is not typically necessary for generating a sequencing library using cfDNA samples.

Typically, whether polynucleotides are forcibly fragmented (e.g., fragmented in vitro), or naturally exist as fragments, they are converted to blunt-ended DNA having 5'-phosphates and 3'-hydroxyl. Standard protocols e.g. protocols for sequencing using, for example, the Illumina platform as described elsewhere herein, instruct users to end-repair sample DNA, to purify the end-repaired products prior to dA-tailing, and to purify the dA-tailing products prior to the adaptor-ligating steps of the library preparation.

Various embodiments, of methods of sequence library preparation described herein obviate the need to perform one or more of the steps typically mandated by standard protocols to obtain a modified DNA product that can be sequenced by NGS. An abbreviated method (ABB method), a 1-step method, and a 2-step method are described below. Consecutive dA-tailing and adaptor ligation is herein referred to as the 2-step process. Consecutive dA-tailing, adaptor ligating, and amplifying is herein referred to as the 1-step method. In various embodiments the ABB and 2-step methods can be performed in solution or on a solid surface. In certain embodiments the 1-step method is performed on a solid surface. Further details on ABB, 2-step and 1-step preparation are disclosed in U.S. Patent Application No. US20130029852 A1, which is incorporated by reference for its description of sequencing library preparation.

Marker Nucleic Acids for Tracking and Verifying Sample Integrity

In various embodiments verification of the integrity of the samples and sample tracking can be accomplished by sequencing mixtures of sample genomic nucleic acids e.g. cfDNA, and accompanying marker nucleic acids that have been introduced into the samples, e.g., prior to processing.

Marker nucleic acids can be combined with the test sample (e.g., biological source sample) and subjected to processes that include, for example, one or more of the steps of fractionating the biological source sample e.g. obtaining an essentially cell-free plasma fraction from a whole blood sample, and sequencing. In some embodiments, sequencing comprises preparing a sequencing library. The sequence or combination of sequences of the marker molecules that are combined with a source sample is chosen to be unique to the source sample. In some embodiments, the unique marker molecules in a sample all have the same sequence. In other embodiments, the unique marker molecules in a sample are a plurality of sequences, e.g., a combination of two, three, four, five, six, seven, eight, nine, ten, fifteen, twenty, or more different sequences.

In one embodiment, the integrity of a sample can be verified using a plurality of marker nucleic acid molecules having identical sequences. Alternatively, the identity of a sample can be verified using a plurality of marker nucleic acid molecules that have at least two, at least three, at least four, at least five, at least six, at least seven, at least eight, at least nine, at least ten, at least 11, at least 12, at least 13, at least 14, at least 15, at least 16, at least 17, at least 18, at least 19, at least 20, at least 25, at least 30, at least 35, at least 40, at least 50, or more different sequences. Verification of the integrity of the plurality of biological samples i.e. two or more biological samples, requires that each of the two or more samples be marked with marker nucleic acids that have sequences that are unique to each of the plurality of test sample that is being marked. For example, a first sample can be marked with a marker nucleic acid having sequence A, and a second sample can be marked with a marker nucleic acid having sequence B. Alternatively, a first sample can be marked with marker nucleic acid molecules all having sequence A, and a second sample can be marked with a mixture of sequences B and C, wherein sequences A, B and C are marker molecules having different sequences.

The marker nucleic acid(s) can be added to the sample at any stage of sample preparation that occurs prior to library preparation (if libraries are to be prepared) and sequencing. In one embodiment, marker molecules can be combined with an unprocessed source sample. For example, the marker nucleic acid can be provided in a collection tube that is used to collect a blood sample. Alternatively, the marker nucleic acids can be added to the blood sample following the blood draw. In one embodiment, the marker nucleic acid is added to the vessel that is used to collect a biological fluid sample e.g. the marker nucleic acid(s) are added to a blood collection tube that is used to collect a blood sample. In another embodiment, the marker nucleic acid(s) are added to a fraction of the biological fluid sample. For example, the marker nucleic acid is added to the plasma and/or serum fraction of a blood sample e.g. a maternal plasma sample. Similarly, the marker nucleic acids can be added to a biopsy specimen prior to processing the specimen. In some embodiments, the marker nucleic acids can be combined with a carrier that delivers the marker molecules into the cells of the biological sample. Cell-delivery carriers include pH-sensitive and cationic liposomes.

In various embodiments, the marker molecules have antigenomic sequences, that are sequences that are absent from the genome of the biological source sample. In an exemplary embodiment, the marker molecules that are used to verify the integrity of a human biological source sample have sequences that are absent from the human genome. In an alternative embodiment, the marker molecules have sequences that are absent from the source sample and from any one or more other known genomes. For example, the marker molecules that are used to verify the integrity of a human biological source sample have sequences that are absent from the human genome and from the mouse genome. The alternative allows for verifying the integrity of a test sample that comprises two or more genomes. For example, the integrity of a human cell-free DNA sample obtained from a subject affected by a pathogen e.g. a bacterium, can be verified using marker molecules having sequences that are absent from both the human genome and the genome of the affecting bacterium. Sequences of genomes of numerous pathogens e.g. bacteria, viruses, yeasts, fungi, protozoa etc., are publicly available on the world wide web at ncbi.nlm.nih.gov/genomes. In another embodiment, marker molecules are nucleic acids that have sequences that are absent from any known genome. The sequences of marker molecules can be randomly generated algorithmically.

In various embodiments the marker molecules can be naturally-occurring deoxyribonucleic acids (DNA), ribonucleic acids or artificial nucleic acid analogs (nucleic acid mimics) including peptide nucleic acids (PMA), morpholino nucleic acid, locked nucleic acids, glycol nucleic acids, and threose nucleic acids, which are distinguished from naturally-occurring DNA or RNA by changes to the backbone of the molecule or DNA mimics that do not have a phosphodiester backbone. The deoxyribonucleic acids can be from naturally-occurring genomes or can be generated in a laboratory through the use of enzymes or by solid phase chemical synthesis. Chemical methods can also be used to generate the DNA mimics that are not found in nature. Derivatives of DNA are that are available in which the phosphodiester linkage has been replaced but in which the deoxyribose is retained include but are not limited to DNA mimics having backbones formed by thioformacetal or a carboxamide linkage, which have been shown to be good structural DNA mimics. Other DNA mimics include morpholino derivatives and the peptide nucleic acids (PNA), which contain an N-(2-aminoethyl)glycine-based pseudo-peptide backbone (Ann Rev Biophys Biomol Struct 24:167-183 [1995]). PNA is an extremely good structural mimic of DNA (or of ribonucleic acid [RNA]), and PNA oligomers are able to form very stable duplex structures with Watson-Crick complementary DNA and RNA (or PNA) oligomers, and they can also bind to targets in duplex DNA by helix invasion (Mol Biotechnol 26:233-248 [2004]. Another good structural mimic/analog of DNA analog that can be used as a marker molecule is phosphorothioate DNA in which one of the non-bridging oxygens is replaced by a sulfur. This modification reduces the action of endo- and exonucleases2 including 5' to 3' and 3' to 5' DNA POL 1 exonuclease, nucleases S1 and P1, RNases, serum nucleases and snake venom phosphodiesterase.

The length of the marker molecules can be distinct or indistinct from that of the sample nucleic acids i.e. the length of the marker molecules can be similar to that of the sample genomic molecules, or it can be greater or smaller than that of the sample genomic molecules. The length of the marker molecules is measured by the number of nucleotide or nucleotide analog bases that constitute the marker molecule. Marker molecules having lengths that differ from those of the sample genomic molecules can be distinguished from source nucleic acids using separation methods known in the art. For example, differences in the length of the marker and sample nucleic acid molecules can be determined by electrophoretic separation e.g. capillary electrophoresis. Size differentiation can be advantageous for quantifying and assessing the quality of the marker and sample nucleic acids. Preferably, the marker nucleic acids are shorter than the genomic nucleic acids, and of sufficient length to exclude them from being mapped to the genome of the sample. For example, as a 30 base human sequence is needed to uniquely map it to a human genome. Accordingly in certain embodiments, marker molecules used in sequencing bioassays of human samples should be at least 30 bp in length.

The choice of length of the marker molecule is determined primarily by the sequencing technology that is used to verify the integrity of a source sample. The length of the sample genomic nucleic acids being sequenced can also be considered. For example, some sequencing technologies employ clonal amplification of polynucleotides, which can require that the genomic polynucleotides that are to be clonally amplified be of a minimum length. For example, sequencing using the Illumina GAII sequence analyzer includes an in vitro clonal amplification by bridge PCR (also known as cluster amplification) of polynucleotides that have a minimum length of 110 bp, to which adaptors are ligated to provide a nucleic acid of at least 200 bp and less than 600 bp that can be clonally amplified and sequenced. In some embodiments, the length of the adaptor-ligated marker molecule is between about 200 bp and about 600 bp, between about 250 bp and 550 bp, between about 300 bp and 500 bp, or between about 350 and 450. In other embodiments, the length of the adaptor-ligated marker molecule is about 200 bp. For example, when sequencing fetal cfDNA that is present in a maternal sample, the length of the marker molecule can be chosen to be similar to that of fetal cfDNA molecules. Thus, in one embodiment, the length of the marker molecule used in an assay that comprises massively parallel sequencing of cfDNA in a maternal sample to determine the presence or absence of a fetal chromosomal aneuploidy, can be about 150 bp, about 160 bp, 170 bp, about 180 bp, about 190 bp or about 200 bp; preferably, the marker molecule is about 170 bp. Other sequencing approaches e.g. SOLiD sequencing, Polony Sequencing and 454 sequencing use emulsion PCR to clonally amplify DNA molecules for sequencing, and each technology dictates the minimum and the maximum length of the molecules that are to be amplified. The length of marker molecules to be sequenced as clonally amplified nucleic acids can be up to about 600 bp. In some embodiments, the length of marker molecules to be sequenced can be greater than 600 bp.

Single molecule sequencing technologies, that do not employ clonal amplification of molecules, and are capable of sequencing nucleic acids over a very broad range of template lengths, in most situations do not require that the molecules to be sequenced be of any specific length. However, the yield of sequences per unit mass is dependent on the number of 3' end hydroxyl groups, and thus having relatively short templates for sequencing is more efficient than having long templates. If starting with nucleic acids longer than 1000 nt, it is generally advisable to shear the nucleic acids to an average length of 100 to 200 nt so that more sequence information can be generated from the same mass of nucleic acids. Thus, the length of the marker molecule can range from tens of bases to thousands of bases. The length of marker molecules used for single molecule sequencing can be up to about 25 bp, up to about 50 bp, up to about 75 bp, up to about 100 bp, up to about 200 bp, up to about 300 bp, up to about 400 bp, up to about 500 bp, up to about 600 bp, up to about 700 bp, up to about 800 bp, up to about 900 bp, up to about 1000 bp, or more in length.

The length chosen for a marker molecule is also determined by the length of the genomic nucleic acid that is being sequenced. For example, cfDNA circulates in the human bloodstream as genomic fragments of cellular genomic DNA. Fetal cfDNA molecules found in the plasma of pregnant women are generally shorter than maternal cfDNA molecules (Chan et al., Clin Chem 50:8892 [2004]). Size fractionation of circulating fetal DNA has confirmed that the average length of circulating fetal DNA fragments is <300 bp, while maternal DNA has been estimated to be between about 0.5 and 1 Kb (Li et al., Clin Chem, 50: 1002-1011 [2004]). These findings are consistent with those of Fan et al., who determined using NGS that fetal cfDNA is rarely >340 bp (Fan et al., Clin Chem 56:1279-1286 [2010]). DNA isolated from urine with a standard silica-based method consists of two fractions, high molecular weight DNA, which originates from shed cells and low molecular weight (150-250 base pair) fraction of transrenal DNA (Tr-DNA) (Botezatu et al., Clin Chem. 46: 1078-1084, 2000; and Su et al., J. Mol. Diagn. 6: 101-107, 2004). The application of newly developed technique for isolation of cell-free nucleic acids from body fluids to the isolation of transrenal nucleic acids has revealed the presence in urine of DNA and RNA fragments much shorter than 150 base pairs (U.S. Patent Application Publication No. 20080139801). In embodiments, wherein cfDNA is the genomic nucleic acid that is sequenced, marker molecules that are chosen can be up to about the length of the cfDNA. For example, the length of marker molecules used in maternal cfDNA samples to be sequenced as single nucleic acid molecules or as clonally amplified nucleic acids can be between about 100 bp and 600. In other embodiments, the sample genomic nucleic acids are fragments of larger molecules. For example, a sample genomic nucleic acid that is sequenced is fragmented cellular DNA. In embodiments, when fragmented cellular DNA is sequenced, the length of the marker molecules can be up to the length of the DNA fragments. In some embodiments, the length of the marker molecules is at least the minimum length required for mapping the sequence read uniquely to the appropriate reference genome. In other embodiments, the length of the marker molecule is the minimum length that is required to exclude the marker molecule from being mapped to the sample reference genome.

In addition, marker molecules can be used to verify samples that are not assayed by nucleic acid sequencing, and that can be verified by common biotechniques other than sequencing e.g. real-time PCR.

Sample Controls (e.g., in Process Positive Controls for Sequencing and/or Analysis).

In various embodiments marker sequences introduced into the samples, e.g., as described above, can function as positive controls to verify the accuracy and efficacy of sequencing and subsequent processing and analysis.

Accordingly, compositions and method for providing an in-process positive control (IPC) for sequencing DNA in a sample are provided. In certain embodiments, positive controls are provided for sequencing cfDNA in a sample comprising a mixture of genomes are provided. An IPC can be used to relate baseline shifts in sequence information obtained from different sets of samples e.g. samples that are sequenced at different times on different sequencing runs. Thus, for example, an IPC can relate the sequence information obtained for a maternal test sample to the sequence information obtained from a set of qualified samples that were sequenced at a different time.

Similarly, in the case of segment analysis, an IPC can relate the sequence information obtained from a subject for particular segment(s) to the sequence obtained from a set of qualified samples (of similar sequences) that were sequenced at a different time. In certain embodiments an IPC can relate the sequence information obtained from a subject for particular cancer-related loci to the sequence information obtained from a set of qualified samples (e.g., from a known amplification/deletion, and the like).

In addition, IPCs can be used as markers to track sample(s) through the sequencing process. IPCs can also provide a qualitative positive sequence dose value e.g. NCV, for one or more aneuploidies of chromosomes of interest e.g. trisomy 21, trisomy 13, trisomy 18 to provide proper interpretation, and to ensure the dependability and accuracy of the data. In certain embodiments IPCs can be created to comprise nucleic acids from male and female genomes to provide doses for chromosomes X and Y in a maternal sample to determine whether the fetus is male.

The type and the number of in-process controls depends on the type or nature of the test needed. For example, for a test requiring the sequencing of DNA from a sample comprising a mixture of genomes to determine whether a chromosomal aneuploidy exists, the in-process control can comprise DNA obtained from a sample known to comprise the same chromosomal aneuploidy that is being tested. For example, the IPC for a test to determine the presence or absence of a fetal trisomy e.g. trisomy 21, in a maternal sample comprises DNA obtained from an individual with trisomy 21. In some embodiments, the IPC comprises a mixture of DNA obtained from two or more individuals with different aneuploidies. For example, for a test to determine the presence or absence of trisomy 13, trisomy 18, trisomy 21, and monosomy X, the IPC comprises a combination of DNA samples obtained from pregnant women each carrying a fetus with one of the trisomies being tested. In addition to complete chromosomal aneuploidies, IPCs can be created to provide positive controls for tests to determine the presence or absence of partial aneuploidies.

An IPC that serves as the control for detecting a single aneuploidy can be created using a mixture of cellular genomic DNA obtained from two subjects, one being the contributor of the aneuploid genome. For example, an IPC that is created as a control for a test to determine a fetal trisomy e.g. trisomy 21, can be created by combining genomic DNA from a male or female subject carrying the trisomic chromosome with genomic DNA with a female subject known not to carry the trisomic chromosome. Genomic DNA can be extracted from cells of both subjects, and sheared to provide fragments of between about 100-400 bp, between about 150-350 bp, or between about 200-300 bp to simulate the circulating cfDNA fragments in maternal samples. The proportion of fragmented DNA from the subject carrying the aneuploidy e.g. trisomy 21, is chosen to simulate the proportion of circulating fetal cfDNA found in maternal samples to provide an IPC comprising a mixture of fragmented DNA comprising about 5%, about 10%, about 15%, about 20%, about 25%, about 30%, of DNA from the subject carrying the aneuploidy. The IPC can comprise DNA from different subjects each carrying a different aneuploidy. For example, the IPC can comprise about 80% of the unaffected female DNA, and the remaining 20% can be DNA from three different subjects each carrying a trisomic chromosome 21, a trisomic chromosome 13, and a trisomic chromosome 18. The mixture of fragmented DNA is prepared for sequencing. Processing of the mixture of fragmented DNA can comprise preparing a sequencing library, which can be sequenced using any massively parallel methods in singleplex or multiplex fashion. Stock solutions of the genomic IPC can be stored and used in multiple diagnostic tests.

Alternatively the IPC can be created using cfDNA obtained from a mother known to carry a fetus with a known chromosomal aneuploidy. For example, cfDNA can be obtained from a pregnant woman carrying a fetus with trisomy 21. The cfDNA is extracted from the maternal sample, and cloned into a bacterial vector and grown in bacteria to provide an ongoing source of the IPC. The DNA can be extracted from the bacterial vector using restriction enzymes. Alternatively, the cloned cfDNA can be amplified by e.g. PCR. The IPC DNA can be processed for sequencing in the same runs as the cfDNA from the test samples that are to be analyzed for the presence or absence of chromosomal aneuploidies.

While the creation of IPCs is described above with respect to trisomys, it will be appreciated that IPCs can be created to reflect other partial aneuploidies including for example, various segment amplification and/or deletions. Thus, for example, where various cancers are known to be associated with particular amplifications (e.g., breast cancer associated with 20Q13) IPCs can be created that incorporate those known amplifications.

Sequencing Methods

The prepared samples (e.g., Sequencing Libraries) may be sequenced for various purposes. For example, sequencing may be used for identifying copy number variation(s). Any of a number of sequencing technologies can be utilized. The above-described techniques for preparing or working with cfDNA-containing samples can be used to provide a source of cfDNA for any of the methods described herein. The above-described methods for applying adaptor sequences to the ends of cfDNA apply only to those sequencing methods that employ adaptors.

Some sequencing technologies are available commercially, such as the sequencing-by-hybridization platform from AFFYMETRIX® Inc. (Sunnyvale, Calif.) and the sequencing-by-synthesis platforms from 454 Life Sciences (Bradford, Conn.), Illumina (Hayward, Calif.) and Helicos Biosciences (Cambridge, Mass.), and the sequencing-by-ligation platform from Applied Biosystems (Foster City, Calif.), as described below. In addition to the single molecule sequencing performed using sequencing-by-synthesis of Helicos Biosciences, other single molecule sequencing technologies include, but are not limited to, the SMRT™ technology of Pacific Biosciences, the ION TORREN™ technology, and nanopore sequencing developed for example, by Oxford Nanopore Technologies.

While the automated Sanger method is considered as a 'first generation' technology, Sanger sequencing including the automated Sanger sequencing, can also be employed in the methods described herein. Additional suitable sequencing methods include, but are not limited to nucleic acid imaging technologies e.g. atomic force microscopy (AFM) or transmission electron microscopy (TEM). Such techniques may be appropriate for sequencing cfDNA obtained using the freeze-thaw method described above, for example. Illustrative sequencing technologies are described in greater detail below.

In one illustrative, but non-limiting, embodiment, the methods described herein comprise obtaining sequence information for the nucleic acids in a test sample e.g. cfDNA in a maternal sample, cfDNA or cellular DNA in a subject being screened for a cancer, and the like, using single molecule sequencing technology of the Helicos True Single Molecule Sequencing (tSMS) technology (e.g. as described in Harris T. D. et al., Science 320:106-109 [2008]). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. In certain embodiments the templates can be at a density of about 100 million templates/cm$^2$. The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are discerned by imaging the flow cell surface. After imaging, a cleavage step removes the fluorescent label, and the process is repeated with other fluorescently labeled nucleotides until the desired read length is achieved. Sequence information is collected with each nucleotide addition step. Whole genome sequencing by single molecule sequencing technologies excludes or typically obviates PCR-based amplification in the preparation of the sequencing libraries, and the methods allow for direct measurement of the sample, rather than measurement of copies of that sample.

In another illustrative, but non-limiting, embodiment, the methods described herein comprise obtaining sequence information for the nucleic acids in the test sample e.g. cfDNA in a maternal test sample, cfDNA or cellular DNA in a subject being screened for a cancer, and the like, using the 454 sequencing (Roche) (e.g. as described in Margulies, M. et al. Nature 437:376-380 [2005]). 454 sequencing typically involves two steps. In the first step, DNA is sheared into fragments of approximately 300-800 base pairs, and the fragments are blunt-ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (e.g., picoliter-sized wells). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is measured and analyzed.

In another illustrative, but non-limiting, embodiment, the methods described herein comprises obtaining sequence information for the nucleic acids in the test sample e.g. cfDNA in a maternal test sample, cfDNA or cellular DNA in a subject being screened for a cancer, and the like, using the SOLiD™ technology (Applied Biosystems). In SOLiD™ sequencing-by-ligation, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

In another illustrative, but non-limiting, embodiment, the methods described herein comprise obtaining sequence information for the nucleic acids in the test sample e.g. cfDNA in a maternal test sample, cfDNA or cellular DNA in a subject being screened for a cancer, and the like, using the single molecule, real-time (SMRT™) sequencing technology of Pacific Biosciences. In SMRT sequencing, the continuous incorporation of dye-labeled nucleotides is imaged during DNA synthesis. Single DNA polymerase molecules are attached to the bottom surface of individual zero-mode wavelength detectors (ZMW detectors) that obtain sequence information while phospholinked nucleotides are being incorporated into the growing primer strand. A ZMW detector comprises a confinement structure that enables observation of incorporation of a single nucleotide by DNA polymerase against a background of fluorescent nucleotides that rapidly diffuse in an out of the ZMW (e.g., in microseconds). It typically takes several milliseconds to incorporate a nucleotide into a growing strand. During this time, the fluorescent label is excited and produces a fluorescent signal, and the fluorescent tag is cleaved off. Measurement of the corresponding fluorescence of the dye indicates which base was incorporated. The process is repeated to provide a sequence.

In another illustrative, but non-limiting, embodiment, the methods described herein comprise obtaining sequence information for the nucleic acids in the test sample e.g. cfDNA in a maternal test sample, cfDNA or cellular DNA in a subject being screened for a cancer, and the like, using nanopore sequencing (e.g. as described in Soni G V and Meller A. Clin Chem 53: 1996-2001 [2007]). Nanopore sequencing DNA analysis techniques are developed by a number of companies, including, for example, Oxford Nanopore Technologies (Oxford, United Kingdom), Sequenom, NABsys, and the like. Nanopore sequencing is a single-molecule sequencing technology whereby a single molecule of DNA is sequenced directly as it passes through a nanopore. A nanopore is a small hole, typically of the order of 1 nanometer in diameter. Immersion of a nanopore in a conducting fluid and application of a potential (voltage) across it results in a slight electrical current due to conduction of ions through the nanopore. The amount of current that flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore provides a read of the DNA sequence.

In another illustrative, but non-limiting, embodiment, the methods described herein comprises obtaining sequence information for the nucleic acids in the test sample e.g. cfDNA in a maternal test sample, cfDNA or cellular DNA in a subject being screened for a cancer, and the like, using the chemical-sensitive field effect transistor (chemFET) array (e.g., as described in U.S. Patent Application Publication No. 2009/0026082). In one example of this technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be discerned as a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

In another embodiment, the present method comprises obtaining sequence information for the nucleic acids in the test sample e.g. cfDNA in a maternal test sample, using the Halcyon Molecular's technology, which uses transmission electron microscopy (TEM). The method, termed Individual Molecule Placement Rapid Nano Transfer (IMPRNT), comprises utilizing single atom resolution transmission electron microscope imaging of high-molecular weight (150 kb or greater) DNA selectively labeled with heavy atom markers and arranging these molecules on ultra-thin films in ultra-dense (3 nm strand-to-strand) parallel arrays with consistent base-to-base spacing. The electron microscope is used to image the molecules on the films to determine the position of the heavy atom markers and to extract base sequence information from the DNA. The method is further described in PCT patent publication WO 2009/046445. The method allows for sequencing complete human genomes in less than ten minutes.

In another embodiment, the DNA sequencing technology is the Ion Torrent single molecule sequencing, which pairs semiconductor technology with a simple sequencing chemistry to directly translate chemically encoded information (A, C, G, T) into digital information (0, 1) on a semiconductor chip. In nature, when a nucleotide is incorporated into a strand of DNA by a polymerase, a hydrogen ion is released as a byproduct. Ion Torrent uses a high-density array of micro-machined wells to perform this biochemical process in a massively parallel way. Each well holds a different DNA molecule. Beneath the wells is an ion-sensitive layer and beneath that an ion sensor. When a nucleotide, for example a C, is added to a DNA template and is then incorporated into a strand of DNA, a hydrogen ion will be released. The charge from that ion will change the pH of the solution, which can be detected by Ion Torrent's ion sensor. The sequencer—essentially the world's smallest solid-state pH meter—calls the base, going directly from chemical information to digital information. The Ion personal Genome Machine (PGM™) sequencer then sequentially floods the chip with one nucleotide after another. If the next nucleotide that floods the chip is not a match. No voltage change will be recorded and no base will be called. If there are two identical bases on the DNA strand, the voltage will be double, and the chip will record two identical bases called. Direct detection allows recordation of nucleotide incorporation in seconds.

In another embodiment, the present method comprises obtaining sequence information for the nucleic acids in the test sample e.g. cfDNA in a maternal test sample, using sequencing by hybridization. Sequencing-by-hybridization comprises contacting the plurality of polynucleotide sequences with a plurality of polynucleotide probes, wherein each of the plurality of polynucleotide probes can be optionally tethered to a substrate. The substrate might be flat surface comprising an array of known nucleotide sequences. The pattern of hybridization to the array can be used to determine the polynucleotide sequences present in the sample. In other embodiments, each probe is tethered to a bead, e.g., a magnetic bead or the like. Hybridization to the beads can be determined and used to identify the plurality of polynucleotide sequences within the sample.

In another embodiment, the present method comprises obtaining sequence information for the nucleic acids in the test sample e.g. cfDNA in a maternal test sample, by massively parallel sequencing of millions of DNA fragments using Illumina's sequencing-by-synthesis and reversible terminator-based sequencing chemistry (e.g. as described in Bentley et al., Nature 6:53-59 [2009]). Template DNA can be genomic DNA e.g. cfDNA. In some embodiments, genomic DNA from isolated cells is used as the template, and it is fragmented into lengths of several hundred base pairs. In other embodiments, cfDNA is used as the template, and fragmentation is not required as cfDNA exists as short fragments. For example fetal cfDNA circulates in the bloodstream as fragments approximately 170 base pairs (bp) in length (Fan et al., Clin Chem 56:1279-1286 [2010]), and no fragmentation of the DNA is required prior to sequencing. Illumina's sequencing technology relies on the attachment of fragmented genomic DNA to a planar, optically transparent surface on which oligonucleotide anchors are bound. Template DNA is end-repaired to generate 5'-phosphorylated blunt ends, and the polymerase activity of Klenow fragment is used to add a single A base to the 3' end of the blunt phosphorylated DNA fragments. This addition prepares the DNA fragments for ligation to oligonucleotide adapters, which have an overhang of a single T base at their 3' end to increase ligation efficiency. The adapter oligonucleotides are complementary to the flow-cell anchors. Under limiting-dilution conditions, adapter-modified, single-stranded template DNA is added to the flow cell and immobilized by hybridization to the anchors. Attached DNA fragments are extended and bridge amplified to create an ultra-high density sequencing flow cell with hundreds of millions of clusters, each containing ~1,000 copies of the same template. In one embodiment, the randomly fragmented genomic DNA e.g. cfDNA, is amplified using PCR before it is subjected to cluster amplification. Alternatively, an amplification-free genomic library preparation is used, and the randomly fragmented genomic DNA e.g. cfDNA is enriched using the cluster amplification alone (Kozarewa et al., Nature Methods 6:291-295 [2009]). The templates are sequenced using a robust four-color DNA sequencing-by-synthesis technology that employs reversible terminators with removable fluorescent dyes. High-sensitivity fluorescence detection is achieved using laser excitation and total internal reflection optics. Short sequence reads of about 20-40 bp e.g. 36 bp, are aligned against a repeat-masked reference genome and unique mapping of the short sequence reads to the reference genome are identified using specially developed data analysis pipeline software. Non-repeatmasked reference genomes can also be used. Whether repeat-masked or non-repeat-masked reference genomes are used, only reads that map uniquely to the reference genome are counted. After completion of the first read, the templates can be regenerated in situ to enable a second read from the opposite end of the fragments. Thus, either single-end or paired end sequencing of the DNA fragments can be used. Partial sequencing of DNA fragments present in the sample is performed, and sequence tags comprising reads of predetermined length e.g. 36 bp, are mapped to a known reference genome are counted. In one embodiment, the reference genome sequence is the NCBI36/hg18 sequence, which is available on the world wide web at genome.ucsc.edu/cgi-bin/hgGateway?org=Human&db=hg18&hgsid=166260105). Alternatively, the reference genome sequence is the GRCh37/hg19, which is available on the world wide web at genome.ucsc.edu/cgi-bin/hgGateway. Other sources of public sequence information include GenBank, dbEST, dbSTS, EMBL (the European Molecular Biology Laboratory), and the DDBJ (the DNA Databank of Japan). A number of computer algorithms are available for aligning sequences, including without limitation BLAST (Altschul et al., 1990), BLITZ (MPsrch) (Sturrock & Collins, 1993), FASTA (Person & Lipman, 1988), BOWTIE (Langmead et al., Genome Biology 10:R25.1-R25.10 [2009]), or ELAND (Illumina, Inc., San Diego, Calif., USA). In one embodiment, one end of the clonally expanded copies of the plasma cfDNA molecules is sequenced and processed by bioinformatic alignment analysis for the Illumina Genome Analyzer, which uses the Efficient Large-Scale Alignment of Nucleotide Databases (ELAND) software.

In some embodiments of the methods described herein, the mapped sequence tags comprise sequence reads of about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. It is expected that technological advances will enable single-end reads of greater than 500 bp enabling for reads of greater than about 1000 bp when paired end reads are generated. In one embodiment, the mapped sequence tags comprise sequence reads that are 36 bp. Mapping of the sequence tags is achieved by comparing the sequence of the tag with the sequence of the reference to determine the chromosomal origin of the sequenced nucleic acid (e.g. cfDNA) molecule, and specific genetic sequence information is not needed. A small degree of mismatch (0-2 mismatches per sequence tag) may be allowed to account for minor polymorphisms that may exist between the reference genome and the genomes in the mixed sample.

A plurality of sequence tags are typically obtained per sample. In some embodiments, at least about $3 \times 10^6$ sequence tags, at least about $5 \times 10^6$ sequence tags, at least about $8 \times 10^6$ sequence tags, at least about $10 \times 10^6$ sequence tags, at least about $15 \times 10^6$ sequence tags, at least about $20 \times 10^6$ sequence tags, at least about $30 \times 10^6$ sequence tags, at least about $40 \times 10^6$ sequence tags, or at least about $50 \times 10^6$ sequence tags comprising between 20 and 40 bp reads e.g. 36 bp, are obtained from mapping the reads to the reference genome per sample. In one embodiment, all the sequence reads are mapped to all regions of the reference genome. In one embodiment, the tags that have been mapped to all regions e.g. all chromosomes, of the reference genome are counted, and the CNV i.e. the over- or under-representation of a sequence of interest e.g. a chromosome or portion thereof, in the mixed DNA sample is determined. The method does not require differentiation between the two genomes.

The accuracy required for correctly determining whether a CNV e.g. aneuploidy, is present or absent in a sample, is predicated on the variation of the number of sequence tags that map to the reference genome among samples within a sequencing run (inter-chromosomal variability), and the variation of the number of sequence tags that map to the reference genome in different sequencing runs (inter-sequencing variability). For example, the variations can be particularly pronounced for tags that map to GC-rich or GC-poor reference sequences. Other variations can result from using different protocols for the extraction and purification of the nucleic acids, the preparation of the sequencing libraries, and the use of different sequencing platforms. The present method may use sequence doses (chromosome doses, or segment doses as described below) based on the knowledge of normalizing sequences (normalizing chromosome sequences or normalizing segment sequences), to intrinsically account for the accrued variability stemming from interchromosomal (intra-run), and inter-sequencing (inter-run) and platform-dependent variability. Chromosome doses are based on the knowledge of a normalizing chromosome sequence, which can be composed of a single chromosome, or of two or more chromosomes selected from chromosomes 1-22, X, and Y. Alternatively, normalizing chromosome sequences can be composed of a single chromosome segment, or of two or more segments of one chromosome or of two or more chromosomes. Segment doses are based on the knowledge of a normalizing segment sequence, which can be composed of a single segment of any one chromosome, or of two or more segments of any two or more of chromosomes 1-22, X, and Y.

Singleplex Sequencing

Figure 5:
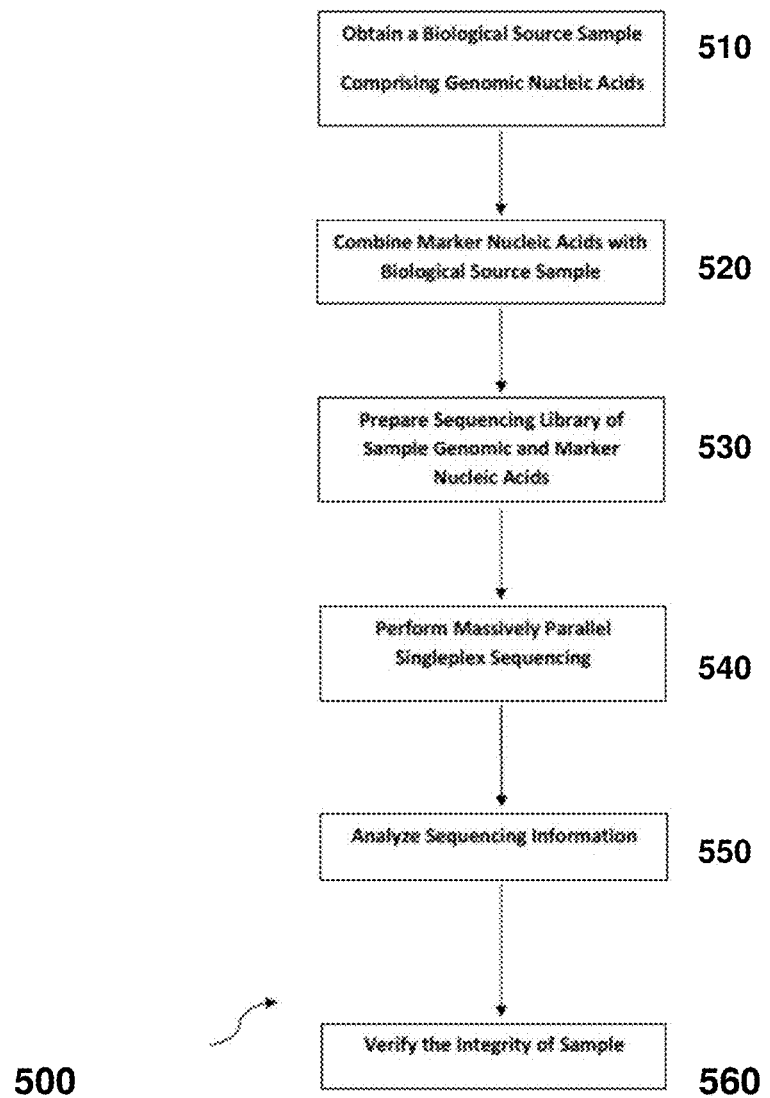
FIG. 5 shows a flow chart of a method whereby marker nucleic acids are combined with source sample nucleic acids of a single sample to assay for a genetic abnormality while determining the integrity of the biological source sample.

FIG. 5 illustrates a flow chart of an embodiment of the method whereby marker nucleic acids are combined with source sample nucleic acids of a single sample to assay for a genetic abnormality while determining the integrity of the biological source sample. In step 510, a biological source sample comprising genomic nucleic acids is obtained. In step 520, marker nucleic acids are combined with the biological source sample to provide a marked sample. A sequencing library of a mixture of clonally amplified source sample genomic and marker nucleic acids is prepared in step 530, and the library is sequenced in a massively parallel fashion in step 540 to provide sequencing information pertaining to the source genomic and marker nucleic acids of the sample. Massively parallel sequencing methods provide sequencing information as sequence reads, which are mapped to one or more reference genomes to generate sequence tags that can be analyzed. In step 550, all sequencing information is analyzed, and based on the sequencing information pertaining to the marker molecules, the integrity of the source sample is verified in step 560. Verification of source sample integrity is accomplished by determining a correspondence between the sequencing information obtained for the maker molecule at step 550 and the known sequence of the marker molecule that was added to the original source sample at step 520. The same process can be applied to multiple samples that are sequenced separately, with each sample comprising molecules having sequences unique to the sample i.e. one sample is marked with a unique marker molecule and it is sequenced separately from other samples in a flow cell or slide of a sequencer. If the integrity of the sample is verified, the sequencing information pertaining to the genomic nucleic acids of the sample can be analyzed to provide information e.g. about the status of the subject from which the source sample was obtained. For example, if the integrity of the sample is verified, the sequencing information pertaining to the genomic nucleic acids is analyzed to determine the presence or absence of a chromosomal abnormality. If the integrity of the sample is not verified, the sequencing information is disregarded.

The method depicted in FIG. 5 is also applicable to bioassays that comprise singleplex sequencing of single molecules e.g. tSMS by Helicos, SMRT by Pacific Biosciences, BASE by Oxford Nanopore, and other technologies such as that suggested by IBM, which do not require preparation of libraries.

Multiplex Sequencing

The large number of sequence reads that can be obtained per sequencing run permits the analysis of pooled samples i.e. multiplexing, which maximizes sequencing capacity and reduces workflow. For example, the massively parallel sequencing of eight libraries performed using the eight lane flow cell of the Illumina Genome Analyzer, and Illumina's HiSeq Systems, can be multiplexed to sequence two or more samples in each lane such that 16, 24, 32 etc. or more samples can be sequenced in a single run. Parallelizing sequencing for multiple samples i.e. multiplex sequencing, requires the incorporation of sample-specific index sequences, also known as barcodes, during the preparation of sequencing libraries. Sequencing indexes are distinct base sequences of about 5, about 10, about 15, about 20 about 25, or more bases that are added at the 3' end of the genomic and marker nucleic acid. The multiplexing system enables sequencing of hundreds of biological samples within a single sequencing run. The preparation of indexed sequencing libraries for sequencing of clonally amplified sequences can be performed by incorporating the index sequence into one of the PCR primers used for cluster amplification. Alternatively, the index sequence can be incorporated into the adaptor, which is ligated to the cfDNA prior to the PCR amplification. Indexed libraries for single molecule sequencing can be created by incorporating the index sequence at the 3' end of the marker and genomic molecule or 5' to the addition of a sequence needed for hybridization to the flow cell anchors e.g. addition of the polyA tail for single molecule sequencing using the tSMS. Sequencing of the uniquely marked indexed nucleic acids provides index sequence information that identifies samples in the pooled sample libraries, and sequence information of marker molecules correlates sequencing information of the genomic nucleic acids to the sample source. In embodiments wherein the multiple samples are sequenced individually i.e. singleplex sequencing, marker and genomic nucleic acid molecules of each sample need only be modified to contain the adaptor sequences as required by the sequencing platform and exclude the indexing sequences.

Figure 6:
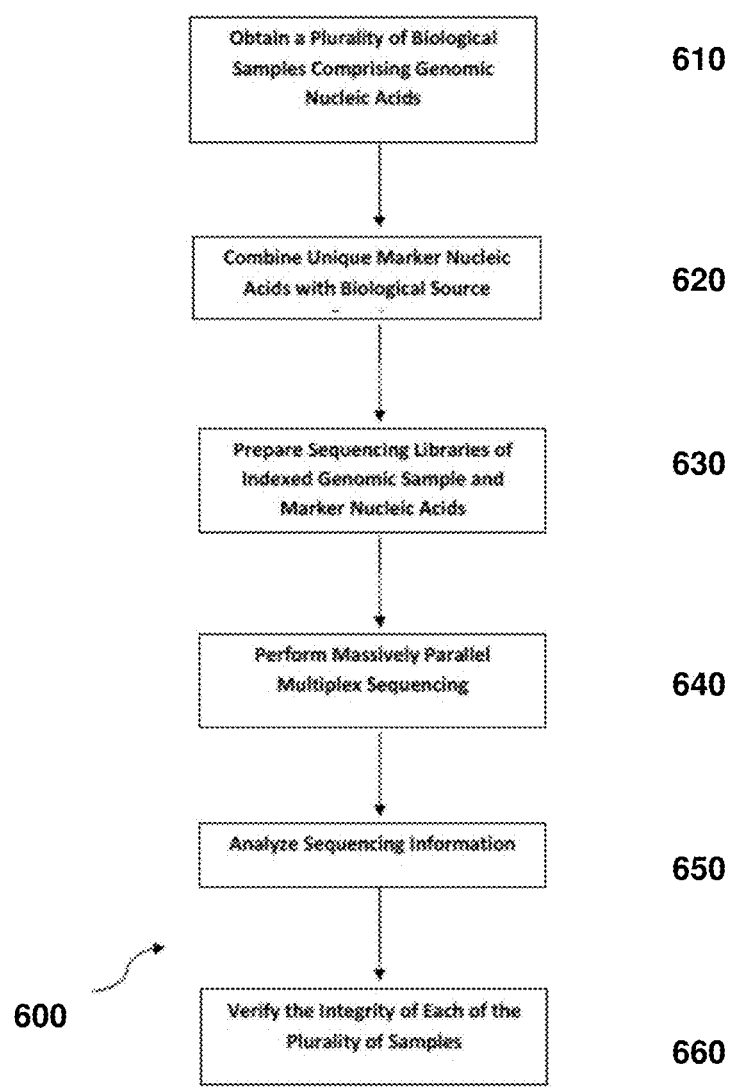
FIG. 6 shows a flowchart of an embodiment of the method for verifying the integrity of samples that are subjected to a multistep multiplex sequencing bioassay.

FIG. 6 provides a flowchart of an embodiment 600 of the method for verifying the integrity of samples that are subjected to a multistep multiplex sequencing bioassay i.e. nucleic acids from individual samples are combined and sequenced as a complex mixture. In step 610, a plurality of biological source samples each comprising genomic nucleic acids is obtained. In step 620, unique marker nucleic acids are combined with each of the biological source samples to provide a plurality of uniquely marked samples. A sequencing library of sample genomic and marker nucleic acids is prepared in step 630 for each of the uniquely marked samples. Library preparation of samples that are destined to undergo multiplexed sequencing comprises the incorporation of distinct indexing tags into the sample and marker nucleic acids of each of the uniquely marked samples to provide samples whose source nucleic acid sequences can be correlated with the corresponding marker nucleic acid sequences and identified in complex solutions. In embodiments of the method comprising marker molecules that can be enzymatically modified, e.g. DNA, indexing molecules can be incorporated at the 3' of the sample and marker molecules by ligating sequenceable adaptor sequences comprising the indexing sequences. In embodiments of the method comprising marker molecules that cannot be enzymatically modified, e.g. DNA analogs that do not have a phosphate backbone, indexing sequences are incorporated at the 3' of the analog marker molecules during synthesis. Sequencing libraries of two or more samples are pooled and loaded on the flow cell of the sequencer where they are sequenced in a massively parallel fashion in step 640. In step 650, all sequencing information is analyzed, and based on the sequencing information pertaining to the marker molecules; the integrity of the source sample is verified in step 660. Verification of the integrity of each of the plurality of source samples is accomplished by first grouping sequence tags associated with identical index sequences to associate the genomic and marker sequences and distinguish sequences belonging to each of the libraries made from genomic molecules of a plurality of samples. Analysis of the grouped marker and genomic sequences is then performed to verify that the sequence obtained for the marker molecules corresponds to the known unique sequence added to the corresponding source sample. If the integrity of the sample is verified, the sequencing information pertaining to the genomic nucleic acids of the sample can be analyzed to provide genetic information about the subject from which the source sample was obtained. For example, if the integrity of the sample is verified, the sequencing information pertaining to the genomic nucleic acids is analyzed to determine the presence or absence of a chromosomal abnormality. The absence of a correspondence between the sequencing information and known sequence of the marker molecule is indicative of a sample mix-up, and the accompanying sequencing information pertaining to the genomic cfDNA molecules is disregarded.

Copy Number Variation Analysis Applications

Sequence information generated as described herein can be used for any number of applications. One application is in determining copy number variations (CNVs) in the cfDNA. CNVs that can be determined according to the present method include trisomies and monosomies of any one or more of chromosomes 1-22, X and Y, other chromosomal polysomies, and deletions and/or duplications of segments of any one or more of the chromosomes, which can be detected by sequencing only once the nucleic acids of a test sample. Any aneuploidy can be determined from sequencing information that is obtained by sequencing only once the nucleic acids of a test sample.

The methods and apparatus described herein may employ next generation sequencing technology (NGS) as described above. In certain embodiments, clonally amplified DNA templates or single DNA molecules are sequenced in a massively parallel fashion within a flow cell (e.g. as described in Volkerding et al. Clin Chem 55:641-658 [2009]; Metzker M Nature Rev 11:31-46 [2010]). In addition to high-throughput sequence information, NGS provides quantitative information, in that each sequence read is a countable "sequence tag" representing an individual clonal DNA template or a single DNA molecule.

In some embodiments, the methods and apparatus disclosed herein may employ the following some or all of the operations from the following: obtain a nucleic acid test sample from a patient (typically by a non-invasive procedure); process the test sample in preparation for sequencing; sequence nucleic acids from the test sample to produce numerous reads (e.g., at least 10,000); align the reads to portions of a reference sequence/genome and determine the amount of DNA (e.g., the number of reads) that map to defined portions the reference sequence (e.g., to defined chromosomes or chromosome segments); calculate a dose of one or more of the defined portions by normalizing the amount of DNA mapping to the defined portions with an amount of DNA mapping to one or more normalizing chromosomes or chromosome segments selected for the defined portion; determining whether the dose indicates that the defined portion is "affected" (e.g., aneuploidy or mosaic); reporting the determination and optionally converting it to a diagnosis; using the diagnosis or determination to develop a plan of treatment, monitoring, or further testing for the patient.

In some embodiments, the biological sample is obtained from a subject and comprises a mixture of nucleic acids contributed by different genomes. The different genomes can be contributed to the sample by two individuals e.g. the different genomes are contributed by the fetus and the mother carrying the fetus. Alternatively, the genomes are contributed to the sample by aneuploid cancerous cells and normal euploid cells from the same subject e.g. a plasma sample from a cancer patient.

Apart from analyzing a patient's test sample, one or more normalizing chromosomes or one or more normalizing chromosome segments are selected for each possible chromosome of interest. The normalizing chromosomes or segments are identified asynchronously from the normal testing of patient samples, which may take place in a clinical setting. In other words, the normalizing chromosomes or segments are identified prior to testing patient samples. The associations between normalizing chromosomes or segments and chromosomes or segments of interest are stored for use during testing.

In some embodiments, a method is provided for determining the presence or absence of any one or more complete fetal chromosomal aneuploidies in a maternal test sample comprising fetal and maternal nucleic acids. The steps of the method comprise: (a) obtaining sequence information for the fetal and maternal nucleic acids in the sample; (b) using the sequence information to identify a number of sequence tags for each of any one or more chromosomes of interest selected from chromosomes 1-22, X and Y and to identify a number of sequence tags for a normalizing segment sequence for each of any one or more chromosomes of interest; (c) using the number of sequence tags identified for each of any one or more chromosomes of interest and the number of sequence tags identified for the normalizing segment sequence to calculate a single chromosome dose for each of any one or more chromosomes of interest; and (d) comparing each of the single chromosome doses for each of any one or more chromosomes of interest to a threshold value for each of the one or more chromosomes of interest, and thereby determining the presence or absence of one or more different complete fetal chromosomal aneuploidies in the sample. Step (a) can comprise sequencing at least a portion of the nucleic acid molecules of a test sample to obtain said sequence information for the fetal and maternal nucleic acid molecules of the test sample.

In some embodiments, step (c) comprises calculating a single chromosome dose for each of the chromosomes of interest as the ratio of the number of sequence tags identified for each of the chromosomes of interest and the number of sequence tags identified for the normalizing segment sequence for each of the chromosomes of interest. In some other embodiments, step (c) comprises (i) calculating a sequence tag density ratio for each of chromosomes of interest, by relating the number of sequence tags identified for each chromosomes of interest in step (b) to the length of each of the chromosomes of interest; (ii) calculating a sequence tag density ratio for each normalizing segment sequence by relating the number of sequence tags identified for the normalizing segment sequence in step (b) to the length of each the normalizing chromosomes; and (iii) using the sequence tag density ratios calculated in steps (i) and (ii) to calculate a single chromosome dose for each of said chromosomes of interest, wherein said chromosome dose is calculated as the ratio of the sequence tag density ratio for each of the chromosomes of interest and the sequence tag density ratio for the normalizing segment sequence for each of the chromosomes of interest.

Copy number variations in the human genome significantly influence human diversity and predisposition to disease (Redon et al., Nature 23:444-454 [2006], Shaikh et al. Genome Res 19:1682-1690 [2009]). CNVs have been known to contribute to genetic disease through different mechanisms, resulting in either imbalance of gene dosage or gene disruption in most cases. In addition to their direct correlation with genetic disorders, CNVs are known to mediate phenotypic changes that can be deleterious. Recently, several studies have reported an increased burden of rare or de novo CNVs in complex disorders such as cancers, Autism, ADHD, and schizophrenia as compared to normal controls, highlighting the potential pathogenicity of rare or unique CNVs (Sebat et al., 316:445-449 [2007]; Walsh et al., Science 320:539-543 [2008]). CNV arise from genomic rearrangements, primarily owing to deletion, duplication, insertion, and unbalanced translocation events.

Copy number variations determined by the methods and apparatus disclosed herein include gains or losses of entire chromosomes, alterations involving very large chromosomal segments that are microscopically visible, and an abundance of sub-microscopic copy number variation of DNA segments ranging from kilobases (kb) to megabases (Mb) in size. The method is applicable to determining CNV of any fetal aneuploidy, and CNVs known or suspected to be associated with a variety of medical conditions.

CNV for Prenatal Diagnoses

The present method is a polymorphism-independent method that for use in NIPD and that does not require that the fetal cfDNA be distinguished from the maternal cfDNA to enable the determination of a fetal aneuploidy. In some embodiments, the aneuploidy is a complete chromosomal trisomy or monosomy, or a partial trisomy or monosomy. Partial aneuploidies are caused by loss or gain of part of a chromosome, and encompass chromosomal imbalances resulting from unbalanced translocations, unbalanced inversions, deletions and insertions. By far, the most common known aneuploidy compatible with life is trisomy 21 i.e. Down Syndrome (DS), which is caused by the presence of part or all of chromosome 21. Rarely, DS can be caused by an inherited or sporadic defect whereby an extra copy of all or part of chromosome 21 becomes attached to another chromosome (usually chromosome 14) to form a single aberrant chromosome. DS is associated with intellectual impairment, severe learning difficulties and excess mortality caused by long-term health problems such as heart disease. Other aneuploidies with well-known clinical significance include Edward syndrome (trisomy 18) and Patau Syndrome (trisomy 13), which are frequently fatal within the first few months of life.

Abnormalities associated with the number of sex chromosomes are also known and include monosomy X e.g. Turner syndrome (XO), and triple X syndrome (XXX) in female births and Kleinefelter syndrome (XXY) and XYY syndrome in male births, which are all associated with various phenotypes including sterility and reduction in intellectual skills Monosomy X [45,X] is a common cause of early pregnancy loss accounting for about 7% of spontaneous abortions. Based on the liveborn frequency of 45,X (also called Turner syndrome) of 1-2/10,000, it is estimated that less than 1% of 45,X conceptuses will survive to term. About 30% of Turners syndrome patients are mosaic with both a 45,X cell line and either a 46,XX cell line or one containing a rearranged X chromosome (Hook and Warburton 1983). The phenotype in a liveborn infant is relatively mild considering the high embryonic lethality and it has been hypothesized that possibly all liveborn females with Turner syndrome carry a cell line containing two sex chromosomes. Monosomy X can occur in females as 45,X or as 45,X/46XX, and in males as 45,X/46XY. Autosomal monosomies in human are generally suggested to be incompatible with life; however, there is quite a number of cytogenetic reports describing full monosomy of one chromosome 21 in live born children (Vosranova I et al., Molecular Cytogen. 1:13 [2008]; Joosten et al., Prenatal Diagn. 17:271-5 [1997]. The method described herein can be used to diagnose these and other chromosomal abnormalities prenatally.

According to some embodiments the methods disclosed herein can determine the presence or absence of chromosomal trisomies of any one of chromosomes 1-22, X and Y. Examples of chromosomal trisomies that can be detected according to the present method include without limitation trisomy 21 (T21; Down Syndrome), trisomy 18 (T18; Edward's Syndrome), trisomy 16 (T16), trisomy 20 (T20), trisomy 22 (T22; Cat Eye Syndrome), trisomy 15 (T15; Prader Willi Syndrome), trisomy 13 (T13; Patau Syndrome), trisomy 8 (T8; Warkany Syndrome), trisomy 9, and the XXY (Kleinefelter Syndrome), XYY, or XXX trisomies. Complete trisomies of other autosomes existing in a non-mosaic state are lethal, but can be compatible with life when present in a mosaic state. It will be appreciated that various complete trisomies, whether existing in a mosaic or non-mosaic state, and partial trisomies can be determined in fetal cfDNA according to the teachings provided herein. Non-limiting examples of partial trisomies that can be determined by the present method include, but are not limited to, partial trisomy 1q32-44, trisomy 9 p, trisomy 4 mosaicism, trisomy 17p, partial trisomy 4q26-qter, partial 2p trisomy, partial trisomy 1q, and/or partial trisomy 6p/monosomy 6q.

The methods disclosed herein can also be used to determine chromosomal monosomy X, chromosomal monosomy 21, and partial monosomies such as, monosomy 13, monosomy 15, monosomy 16, monosomy 21, and monosomy 22, which are known to be involved in pregnancy miscarriage. Partial monosomy of chromosomes typically involved in complete aneuploidy can also be determined by the method described herein.

Non-limiting examples of deletion syndromes that can be determined according to the present method include syndromes caused by partial deletions of chromosomes. Examples of partial deletions that can be determined according to the methods described herein include without limitation partial deletions of chromosomes 1, 4, 5, 7, 11, 18, 15, 13, 17, 22 and 10, which are described in the following. Examples of deletion disorders include but are not limited to 1q21.1 deletion syndrome or 1q21.1 (recurrent) microdeletion, Wolf-Hirschhorn syndrome (WHS) (OMIN #194190), Williams-Beuren Syndrome also known as chromosome 7q11.23 deletion syndrome (OMIN 194050), Jacobsen Syndrome also known as 11q deletion disorder, partial monosomy of chromosome 18 also known as monosomy 18p, Angelman Syndrome and Prader-Willi Syndrome, partial monosomy 13q, Smith-Magenis syndrome (SMS—OMIM #182290), 22q11.2 deletion syndrome also known as DiGeorge syndrome, DiGeorge Syndrome, etc.

Several duplication syndromes caused by the duplication of part of chromosome arms have been identified (see OMIN [Online Mendelian Inheritance in Man viewed online at ncbi.nlm.nih.gov/omim]). In one embodiment, the present method can be used to determine the presence or absence of duplications and/or multiplications of segments of any one of chromosomes 1-22, X and Y. Non-limiting examples of duplications syndromes that can be determined according to the present method include duplications of part of chromosomes 8, 15, 12, and 17, which are described in the following.

Determination of CNV of Clinical Disorders

In addition to the early determination of birth defects, the methods described herein can be applied to the determination of any abnormality in the representation of genetic sequences within the genome. A number of abnormalities in the representation of genetic sequences within the genome have been associated with various pathologies. Such pathologies include, but are not limited to cancer, infectious and autoimmune diseases, diseases of the nervous system, metabolic and/or cardiovascular diseases, and the like.

Accordingly in various embodiments use of the methods described herein in the diagnosis, and/or monitoring, and or treating such pathologies is contemplated. For example, the methods can be applied to determining the presence or absence of a disease, to monitoring the progression of a disease and/or the efficacy of a treatment regimen, to determining the presence or absence of nucleic acids of a pathogen e.g. virus; to determining chromosomal abnormalities associated with graft versus host disease (GVHD), and to determining the contribution of individuals in forensic analyses.

CNVs in Cancer

It has been shown that blood plasma and serum DNA from cancer patients contains measurable quantities of tumor DNA, that can be recovered and used as surrogate source of tumor DNA, and tumors are characterized by aneuploidy, or inappropriate numbers of gene sequences or even entire chromosomes. The determination of a difference in the amount of a given sequence i.e. a sequence of interest, in a sample from an individual can thus be used in the prognosis or diagnosis of a medical condition. In some embodiments, the present method can be used to determine the presence or absence of a chromosomal aneuploidy in a patient suspected or known to be suffering from cancer.

In certain embodiments the aneuploidy is characteristic of the genome of the subject and results in a generally increased predisposition to a cancer. In certain embodiments the aneuploidy is characteristic of particular cells (e.g., tumor cells, proto-tumor neoplastic cells, etc.) that are or have an increased predisposition to neoplasia. Particular aneuploidies are associated with particular cancers or predispositions to particular cancers as described below.

Accordingly, various embodiments of the methods described herein provide a determination of copy number variation of sequence(s) of interest e.g. clinically-relevant sequence(s), in a test sample from a subject where certain variations in copy number provide an indicator of the presence and/or a predisposition to a cancer. In certain embodiments the sample comprises a mixture of nucleic acids is derived from two or more types of cells. In one embodiment, the mixture of nucleic acids is derived from normal and cancerous cells derived from a subject suffering from a medical condition e.g. cancer.

The development of cancer is often accompanied by an alteration in number of whole chromosomes i.e. complete chromosomal aneuploidy, and/or an alteration in the number of segments of chromosomes i.e. partial aneuploidy, caused by a process known as chromosome instability (CIN) (Thoma et al., Swiss Med Weekly 2011:141:w13170). It is believed that many solid tumors, such as breast cancer, progress from initiation to metastasis through the accumulation of several genetic aberrations. [Sato et al., Cancer Res. 50: 7184-7189 [1990]; Jongsma et al., J Clin Pathol: Mol Path 55:305-309 [2002]]. Such genetic aberrations, as they accumulate, may confer proliferative advantages, genetic instability and the attendant ability to evolve drug resistance rapidly, and enhanced angiogenesis, proteolysis and metastasis. The genetic aberrations may affect either recessive "tumor suppressor genes" or dominantly acting oncogenes. Deletions and recombination leading to loss of heterozygosity (LOH) are believed to play a major role in tumor progression by uncovering mutated tumor suppressor alleles.

cfDNA has been found in the circulation of patients diagnosed with malignancies including but not limited to lung cancer (Pathak et al. Clin Chem 52:1833-1842 [2006]), prostate cancer (Schwartzenbach et al. Clin Cancer Res 15:1032-8 [2009]), and breast cancer (Schwartzenbach et al. available online at breast-cancer-research.com/content/11/5/R71 [2009]). Identification of genomic instabilities associated with cancers that can be determined in the circulating cfDNA in cancer patients is a potential diagnostic and prognostic tool. In one embodiment, methods described herein are used to determine CNV of one or more sequence(s) of interest in a sample, e.g., a sample comprising a mixture of nucleic acids derived from a subject that is suspected or is known to have cancer, e.g., carcinoma, sarcoma, lymphoma, leukemia, germ cell tumors and blastoma.

In one embodiment, the sample is a plasma sample derived (processed) from peripheral blood that may comprise a mixture of cfDNA derived from normal and cancerous cells. In another embodiment, the biological sample that is needed to determine whether a CNV is present is derived from a cells that, if a cancer is present, comprise a mixture of cancerous and non-cancerous cells from other biological tissues including, but not limited to biological fluids or in tissue biopsies, swabs, or smears. In other embodiments, the biological sample is a stool (fecal) sample.

The methods described herein are not limited to the analysis of cfDNA. It will be recognized that similar analyses can be performed on cellular DNA samples.

In various embodiments the sequence(s) of interest comprise nucleic acid sequence(s) known or is suspected to play a role in the development and/or progression of the cancer. Examples of a sequence of interest include nucleic acid sequences e.g. complete chromosomes and/or segments of chromosomes, that are amplified or deleted in cancerous cells. Cancers have been shown to correlate with full chromosome aneuploidy, arm level CNV, and/or focal CNV. Examples of cancers associated with CNV are discussed in further detail in U.S. Patent Application No. US20130029852 A1, which is incorporated by reference for its description of CNV's role in cancers.

CNVs in Infectious and Autoimmune Disease

To date a number of studies have reported association between CNV in genes involved in inflammation and the immune response and HIV, asthma, Crohn's disease and other autoimmune disorders (Fanciulli et al., Clin Genet 77:201-213 [2010]). For example, CNV in CCL3L1, has been implicated in HIV/AIDS susceptibility (CCL3L1, 17q11.2 deletion), rheumatoid arthritis (CCL3L1, 17q11.2 deletion), and Kawasaki disease (CCL3L1, 17q11.2 duplication); CNV in HBD-2, has been reported to predispose to colonic Crohn's disease (HDB-2, 8p23.1 deletion) and psoriasis (HDB-2, 8p23.1 deletion); CNV in FCGR3B, was shown to predispose to glomerulonephritis in systemic lupus erthematosous (FCGR3B, 1q23 deletion, 1q23 duplication), anti-neutrophil cytoplasmic antibody (ANCA)-associated vasculatis (FCGR3B, 1q23 deletion), and increase the risk of developing rheumatoid arthritis. There are at least two inflammatory or autoimmune diseases that have been shown to be associated with CNV at different gene loci. For example, Crohn's disease is associated with low copy number at HDB-2, but also with a common deletion polymorphism upstream of the IGRM gene that encodes a member of the p47 immunity-related GTPase family. In addition to the association with FCGR3B copy number, SLE susceptibility has also been reported to be significantly increased among subjects with a lower number of copies of complement component C4.

Associations between genomic deletions at the GSTM1 (GSTM1, 1q23 deletion) and GSTT1 (GSTT1, 22q11.2 deletion) loci and increased risk of atopic asthma have been reported in a number of independent studies. In some embodiments, the methods described herein can be used to determine the presence or absence of a CNV associated with inflammation and/or autoimmune diseases. For example, the methods can be used to determine the presence of a CNV in a patient suspected to be suffering from HIV, asthma, or Crohn's disease. Examples of CNV associated with such diseases include without limitation deletions at 17q11.2, 8p23.1, 1q23, and 22q11.2, and duplications at 17q11.2, and 1q23. In some embodiments, the present method can be used to determine the presence of CNV in genes including but not limited to CCL3L1, HBD-2, FCGR3B, GSTM, GSTT1, C4, and IRGM.

CNV Diseases of the Nervous System

Associations between de novo and inherited CNV and several common neurological and psychiatric diseases have been reported in autism, schizophrenia and epilepsy, and some cases of neurodegenerative diseases such as Parkinson's disease, amyotrophic lateral sclerosis (ALS) and autosomal dominant Alzheimer's disease (Fanciulli et al., Clin Genet 77:201-213 [2010]). Cytogenetic abnormalities have been observed in patients with autism and autism spectrum disorders (ASDs) with duplications at 15q11-q13. According to the Autism Genome project Consortium, 154 CNV including several recurrent CNVs, either on chromosome 15q11-q13 or at new genomic locations including chromosome 2p16, 1q21 and at 17p12 in a region associated with Smith-Magenis syndrome that overlaps with ASD. Recurrent microdeletions or microduplications on chromosome 16p11.2 have highlighted the observation that de novo CNVs are detected at loci for genes such as SHANK3 (22q13.3 deletion), neurexin 1 (NRXN1, 2p16.3 deletion)

and the neuroglins (NLGN4, Xp22.33 deletion) that are known to regulate synaptic differentiation and regulate glutaminergic neurotransmitter release. Schizophrenia has also been associated with multiple de novo CNVs. Microdeletions and microduplications associated with schizophrenia contain an overrepresentation of genes belonging to neurodevelopmental and glutaminergic pathways, suggesting that multiple CNVs affecting these genes may contribute directly to the pathogenesis of schizophrenia e.g. ERBB4, 2q34 deletion, SLC1A3, 5p13.3 deletion; RAPEGF4, 2q31.1 deletion; CIT, 12.24 deletion; and multiple genes with de novo CNV. CNVs have also been associated with other neurological disorders including epilepsy (CHRNA7, 15q13.3 deletion), Parkinson's disease (SNCA 4q22 duplication) and ALS (SMN1, 5q12.2.-q13.3 deletion; and SMN2 deletion). In some embodiments, the methods described herein can be used to determine the presence or absence of a CNV associated with diseases of the nervous system. For example, the methods can be used to determine the presence of a CNV in a patient suspected to be suffering from autisim, schizophrenia, epilepsy, neurodegenerative diseases such as Parkinson's disease, amyotrophic lateral sclerosis (ALS) or autosomal dominant Alzheimer's disease. The methods can be used to determine CNV of genes associated with diseases of the nervous system including without limitation any of the Autism Spectrum Disorders (ASD), schizophrenia, and epilepsy, and CNV of genes associated with neurodegenerative disorders such as Parkinson's disease. Examples of CNV associated with such diseases include without limitation duplications at 15q11-q13, 2p16, 1q21, 17p12, 16p11.2, and 4q22, and deletions at 22q13.3, 2p16.3, Xp22.33, 2q34, 5p13.3, 2q31.1, 12.24, 15q13.3, and 5q12.2. In some embodiments, the methods can be used to determine the presence of CNV in genes including but not limited to SHANK3, NLGN4, NRXN1, ERBB4, SLC1A3, RAPGEF4, CIT, CHRNA7, SNCA, SMN1, and SMN2.

CNV and Metabolic or Cardiovascular Diseases

The association between metabolic and cardiovascular traits, such as familial hypercholesterolemia (FH), atherosclerosis and coronary artery disease, and CNVs has been reported in a number of studies (Fanciulli et al., Clin Genet 77:201-213 [2010]). For example, germline rearrangements, mainly deletions, have been observed at the LDLR gene (LDLR, 19p13.2 deletion/duplication) in some FH patients who carry no other LDLR mutations. Another example is the LPA gene that encodes apolipoprotein(a) (apo(a)) whose plasma concentration is associated with risk of coronary artery disease, myocardial infarction (MI) and stroke. Plasma concentrations of the apo(a) containing lipoprotein Lp(a) vary over 1000-fold between individuals and 90% of this variability is genetically determined at the LPA locus, with plasma concentration and Lp(a) isoform size being proportional to a highly variable number of 'kringle 4' repeat sequences (range 5-50). These data indicate that CNV in at least two genes can be associated with cardiovascular risk. The methods described herein can be used in large studies to search specifically for CNV associations with cardiovascular disorders. In some embodiments, the present method can be used to determine the presence or absence of a CNV associated with metabolic or cardiovascular disease. For example, the present method can be used to determine the presence of a CNV in a patient suspected to be suffering from familial hypercholesterolemia. The methods described herein can be used to determine CNV of genes associated with metabolic or cardiovascular disease e.g. hypercholesterolemia. Examples of CNV associated with such diseases include without limitation 19p13.2 deletion/duplication of the LDLR gene, and multiplications in the LPA gene.

Kits

In various embodiments, kits are provided for practice of the methods described herein. In certain embodiments the kits comprise one or more positive internal controls for a full aneuploidy and/or for a partial aneuploidy. Typically, although not necessarily, the controls comprise internal positive controls comprising nucleic acid sequences of the type that are to be screened for. For example, a control for a test to determine the presence or absence of a fetal trisomy e.g. trisomy 21, in a maternal sample can comprises DNA characterized by trisomy 21 (e.g., DNA obtained from an individual with trisomy 21). In some embodiments, the control comprises a mixture of DNA obtained from two or more individuals with different aneuploidies. For example, for a test to determine the presence or absence of trisomy 13, trisomy 18, trisomy 21, and monosomy X, the control can comprise a combination of DNA samples obtained from pregnant women each carrying a fetus with one of the trisomys being tested. In addition to complete chromosomal aneuploidies, IPCs can be created to provide positive controls for tests to determine the presence or absence of partial aneuploidies.

In certain embodiments the positive control(s) comprise one or more nucleic acids comprising a trisomy 21 (T21), and/or a trisomy 18 (T18), and/or a trisomy 13 (T13). In certain embodiments the nucleic acid(s) comprising each of the trisomys present are T21 are provided in separate containers. In certain embodiments the nucleic acids comprising two or more trisomys are provided in a single container. Thus, for example, in certain embodiments, a container may contain T21 and T18, T21 and T13, T18 and T13. In certain embodiments, a container may contain T18, T21 and T13. In these various embodiments, the trisomys may be provided in equal quantity/concentration. In other embodiments, the trisomy may be provided in particular predetermined ratios. In various embodiments the controls can be provided as "stock" solutions of known concentration.

In certain embodiments the control for detecting an aneuploidy comprises a mixture of cellular genomic DNA obtained from a two subjects, one being the contributor of the aneuploid genome. For example, as explained above, an internal positive control (IPC) that is created as a control for a test to determine a fetal trisomy e.g. trisomy 21, can comprise a combination of genomic DNA from a male or female subject carrying the trisomic chromosome with genomic DNA from a female subject known not to carry the trisomic chromosome. In certain embodiments the genomic DNA is sheared to provide fragments of between about 100-400 bp, between about 150-350 bp, or between about 200-300 bp to simulate the circulating cfDNA fragments in maternal samples.

In certain embodiments the proportion of fragmented DNA from the subject carrying the aneuploidy e.g. trisomy 21 in the control, is chosen to simulate the proportion of circulating fetal cfDNA found in maternal samples to provide an IPC comprising a mixture of fragmented DNA comprising about 5%, about 10%, about 15%, about 20%, about 25%, about 30%, of DNA from the subject carrying the aneuploidy. In certain embodiments the control comprise DNA from different subjects each carrying a different aneuploidy. For example, the IPC can comprise about 80% of the unaffected female DNA, and the remaining 20% can be DNA from three different subjects each carrying a trisomic chromosome 21, a trisomic chromosome 13, and a trisomic chromosome 18.

In certain embodiments the control(s) comprise cfDNA obtained from a mother known to carry a fetus with a known chromosomal aneuploidy. For example, the controls can comprise cfDNA obtained from a pregnant woman carrying a fetus with trisomy 21 and/or trisomy 18, and/or trisomy 13. The cfDNA can extracted from the maternal sample, and cloned into a bacterial vector and grown in bacteria to provide an ongoing source of the IPC. Alternatively, the cloned cfDNA can be amplified by e.g. PCR.

While the controls present in the kits are described above with respect to trisomies, they need not be so limited. It will be appreciated that the positive controls present in the kit can be created to reflect other partial aneuploidies including for example, various segment amplification and/or deletions. Thus, for example, where various cancers are known to be associated with particular amplifications or deletions of substantially complete chromosomal arms the positive control(s) can comprise a p arm or a q arm of any one or more of chromosomes 1-22, X and Y. In certain embodiments the control comprises an amplification of one or more arms selected from the group consisting of 1q, 3q, 4p, 4q, 5p, 5q, 6p, 6q, 7p, 7q, 8p, 8q, 9p, 9q, 10p, 10q, 12p, 12q, 13q, 14q, 16p, 17p, 17q, 18p, 18q, 19p, 19q, 20p, 20q, 21q, and/or 22q.

In certain embodiments, the controls comprise aneuploidies for any regions known to be associated with particular amplifications or deletions (e.g., breast cancer associated with an amplification at 20Q13). Illustrative regions include, but are not limited to 17q23 (associated with breast cancer), 19q12 (associate with ovarian cancer), 1q21-1q23 (associated with sarcomas and various solid tumors), 8p11-p12 (associated with breast cancer), the ErbB2 amplicon, and so forth. In certain embodiments the controls comprise an amplification or a deletion of a chromosomal region. In certain embodiments the controls comprise an amplification or a deletion of a chromosomal region comprising a gene. In certain embodiments the controls comprise nucleic acid sequences comprising an amplification of a nucleic acid comprising one or more oncogenes In certain embodiments the controls comprise nucleic acid sequences comprising an amplification of a nucleic acid comprising one or more genes selected from the group consisting of MYC, ERBB2 (EFGR), CCND1 (Cyclin D1), FGFR1, FGFR2, HRAS, KRAS, MYB, MDM2, CCNE, KRAS, MET, ERBB1, CDK4, MYCB, ERBB2, AKT2, MDM2 and CDK4.

The foregoing controls are intended to be illustrative and not limiting. Using the teachings provided herein numerous other controls suitable for incorporation into a kit will be recognized by one of skill in the art.

In certain embodiments, the kits include one or more albumin and Ig depletion columns to deplete background proteins.

In some embodiments, the kits comprise sample holders that are configured to undergo heating, which deactivates many proteases and nucleases. In some embodiments, the sample holders configured to be heated to at least about 65° for at least about 15 to 30 min.

In some embodiments, the kits include one or more fixatives for white blood cell nuclei. In some embodiments, the kits include one or more nuclease inhibitors. In other embodiments, the kits include a Cell Free DNA BCT™ tube available from Streck, Inc. of Omaha, Nebr. for blood collection, the BCT tube including at least one additive that deactivates nucleases.

In some embodiments, the kits include mild detergents and salts. In some embodiments, the detergents are nonionic detergents. In some embodiments, the detergents comprise TWEEN®-20. In some embodiments, the detergent is selected from one or more of TWEEN®-20, TRITON®-X100, BRIJ®-35, SDS, NP40 prior to attempting a library preparation. The concentrations of the detergents tested varied depending on the ionic/non-ionic character of the detergent. E.g., TWEEN®-20, BRIJ®-35 and NP40 were added at 0.1% and 5%; SDS and TRITON®-X100 were added at 0.01% and 0.05%.

In various embodiments in addition to the controls or instead of the controls, the kits comprise one or more nucleic acids and/or nucleic acid mimics that provide marker sequence(s) suitable for tracking and determining sample integrity. In certain embodiments the markers comprise an antigenomic sequence. In certain embodiments the marker sequences range in length from about 30 bp up to about 600 bp in length or about 100 bp to about 400 bp in length. In certain embodiments the marker sequence(s) are at least 30 bp (or nt) in length. In certain embodiments the marker is ligated to an adaptor and the length of the adaptor-ligated marker molecule is between about 200 bp (or nt) and about 600 bp (or nt), between about 250 bp (or nt) and 550 bp (or nt), between about 300 bp (or nt) and 500 bp (or nt), or between about 350 and 450. In certain embodiments, the length of the adaptor-ligated marker molecule is about 200 bp (or nt). In certain embodiments the length of a marker molecule can be about 150 bp (or nt), about 160 bp (or nt), 170 bp (or nt), about 180 bp (or nt), about 190 bp (or nt) or about 200 bp (or nt). In certain embodiments the length of marker ranges up to about 600 bp (or nt).

In certain embodiments the kit provides at least two, or at least three, or at least four, or at least five, or at least six, or at least seven, or at least eight, or at least nine, or at least ten, or at least 11, or at least 12, or at least 13, or at least 14, or at least 15, or at least 16, or at least 17 m, or at least 18, or at least 19, or at least 20, or at least 25, or at least 30, or at least 35, or at least 40, or at least 50 different sequences.

In various embodiments, the markers comprise one or more DNAs or the markers comprise one or more DNA mimetics. Suitable mimetics include, but are not limited to morpholino derivatives, peptide nucleic acids (PNA), and phosphorothioate DNA. In various embodiments the markers are incorporated into the controls. In certain embodiments the markers are incorporated into adaptor(s) and/or provided ligated to adaptors.

In certain embodiments the kit further includes one or more sequencing adaptors. Such adaptors include, but are not limited to indexed sequencing adaptors. In certain embodiments the adaptors comprise a single-stranded arm that include an index sequence and one or more PCR priming sites. For example, adaptor sequences of about 60 bp suitable for use with sequencers from Illumina may be employed.

In certain embodiments the kit further comprises a sample collection device for collection of a biological sample. In certain embodiments the sample collection device comprises a device for collecting blood and, optionally a receptacle for containing blood. In certain embodiments the kit comprises a receptacle for containing blood and the receptacle comprises an anticoagulant and/or cell fixative, and/or one or more antigenomic marker sequence(s).

In certain embodiments the kit further comprises DNA extraction reagents (e.g., a separation matrix and/or an elution solution). The kits can also include reagents for sequencing library preparation. Such reagents include, but are not limited to a solution for end-repairing DNA, and/or a solution for dA-tailing DNA, and/or a solution for adaptor ligating DNA.

In addition, the kits optionally include labeling and/or instructional materials providing directions (e.g., protocols) for the use of the reagents and/or devices provided in the kit. For example, the instructional materials can teach the use of the reagents to prepare samples and/or to determine copy number variation in a biological sample. In certain embodiments the instructional materials teach the use of the materials to detect a trisomy. In certain embodiments the instructional materials teach the use of the materials to detect a cancer or a predisposition to a cancer.

While the instructional materials in the various kits typically comprise written or printed materials they are not limited to such. Any medium capable of storing such instructions and communicating them to an end user is contemplated herein. Such media include, but are not limited to electronic storage media (e.g., magnetic discs, tapes, cartridges, chips), optical media (e.g., CD ROM), and the like. Such media may include addresses to internet sites that provide such instructional materials.

In addition, the kits optionally include labeling and/or instructional materials providing directions (e.g., protocols) for the use of the reagents and/or devices provided in the kit. For example, the instructional materials can teach the use of the reagents to prepare samples and/or to determine copy number variation in a biological sample. In certain embodiments the instructional materials teach the use of the materials to detect a trisomy. In certain embodiments the instructional materials teach the use of the materials to detect a cancer or a predisposition to a cancer.

While the instructional materials in the various kits typically comprise written or printed materials they are not limited to such. Any medium capable of storing such instructions and communicating them to an end user is contemplated herein. Such media include, but are not limited to electronic storage media (e.g., magnetic discs, tapes, cartridges, chips), optical media (e.g., CD ROM), and the like. Such media may include addresses to internet sites that provide such instructional materials.

Optionally, the kit comprises a sequencer for sequencing the fetal and maternal nucleic acids. In embodiments wherein the kit comprises the sequencer, the kit further comprises a consumable portion of a sequencer, wherein the consumable portion is configured to sequence fetal and maternal nucleic acids from one or more maternal test samples. The consumable portion of the sequencer is related to the sequencing platform being used, and in some instances the consumable portion is a flow cell, while in other instances, the consumable portion of the sequencer is a chip configured to detect ions. In certain embodiments, the kit comprises the consumable portion of the sequencer when the sequencer itself is not included in the kit.

In some embodiments, another component of the kit is a computer program product as described elsewhere herein. For example, the kit can comprise a computer program product for classifying a copy number variation in a fetal genome, wherein the computer program product comprises (a) code for analyzing the tag information for the first bin of interest to determine whether (i) the first bin of interest harbors a partial aneuploidy, or (ii) the fetus is a mosaic. The analysis of the tag information for the first bin of interest comprises: (i) code for dividing the sequence for the first bin of interest into a plurality of sub-bins; (ii) code for determining whether any of said sub-bins contains significantly more or significantly less nucleic acid than one or more other sub-bins as determined by a defined threshold difference; and (iii) code for determining that the first bin of interest harbors a partial aneuploidy when any of said sub-bins contain significantly more or significantly less nucleic acid than one or more other sub-bins. In some embodiments, the computer program product comprises additional code for determining that a sub-bin of the first bin of interest containing significantly more or significantly less nucleic acid than one or more other portions harbors the partial aneuploidy.

In some embodiments, the kit comprises a computer program product for classifying a copy number variation in a sub-chromosomal region of a chromosome of interest in a fetal genome, wherein the computer program product comprises a non-transitory computer readable medium on which is provided program instructions for classifying a copy number variation in a sub-chromosomal region of a chromosome of interest in a fetal genome, the instructions comprising: (a) code for receiving sequence reads from fetal and maternal nucleic acids of a maternal test sample, wherein the sequence reads are provided in an electronic format; (b) code for aligning, using a computing apparatus, the sequence reads to a reference chromosome sequence for the chromosome of interest in the fetal genome and thereby providing sequence tags corresponding to the sequence reads; (c) code for computationally identifying a number of the sequence tags that are from the chromosome of interest by using the computing apparatus and determining that the chromosome of interest in the fetus harbors a copy number variation; (d) code for calculating a first fetal fraction value using the number of the sequence tags that are from the chromosome of interest and using the fetal fraction value to determine that the chromosome of interest may contain a partial aneuploidy; (e) code for computationally identifying a number of the sequence tags that are from each of two or more bins within the reference chromosome sequence by using the computing apparatus; and (f) code for determining that a first bin of the two or more bins has a number sequence tags that is greater or lesser than an expected number tags, and thereby concluding that the sub-chromosomal region corresponding to the first bin harbors at least a portion of the partial aneuploidy, and wherein the difference between the number of sequence tags for first bin and the expected number of tags is greater than a defined threshold.

Alternatively, the kit comprises computer program products for classifying a copy number variation in a cancer genome and/or classifying a copy number variation in a sub-chromosomal region of a chromosome of interest in a cancer genome.

The kit may also comprise a sequencer for sequencing the fetal and maternal nucleic acids in maternal samples and/or the cancer and somatic nucleic acids in a cancer sample. The sequencer can be a high throughput sequencer that can process tens or hundreds of samples at the same time e.g. the Illumina HiSeq™ systems, or the sequencer can be a personal sequencer e.g. the Illumina MiSeq™ sequencer. In some embodiments, the kit includes a consumable portion of a sequencer such a chip configured to immobilize nucleic acid, detect changes in pH, conduct fluid manipulations, etc.

The various method, apparatus, systems and uses are described in further detail in the following Examples which are not in any way intended to limit the scope of the invention as claimed. The attached figures are meant to be considered as integral parts of the specification and description of the invention. The following examples are offered to illustrate, but not to limit the claimed invention.

EXAMPLES

The example discussed in method 2 below employs a freeze thaw (FT) technique and dispenses with the plasma isolation step of the conventional cfDNA isolation protocol. The example discussed in method 1 demonstrates a procedure for making a library directly from cfDNA that is in plasma or in a FT blood supernatant, without first isolating cfDNA from the plasma or supernatant.

Method 1—Generating Library Directly from Blood or Plasma without Purifying cfDNA Introduction As explained, in order to sequence a population of DNA fragments using the current massively parallel sequencing systems, adaptor sequences must be attached to either end of the fragments. The collection of DNA fragments with adapters is a sequencing library. The poor yield of conventional cfDNA isolation processes provided the inventors with some motivation for making a cfDNA sequencing library from biological fluids without first purifying the DNA from such fluids.

As explained, the DNA wound around nucleosomes normally wraps and unwraps around the nucleosomal proteins. This "breathing" of cfDNA can be utilized to generate a DNA library by attaching adaptors while the cfDNA remains associated with the nucleosomeal proteins.

Minimum Amount of Biological Fluid Required

In a process by which a sequencing library is generated directly from a biological fluid without an intervening DNA isolation step, there is a minimum amount of the fluid required to successfully generate the library and still generate useable downstream data.

In the experiment described in this method, cfDNA was isolated from decreasing volumes of plasma—200 ul, 100 ul, 50 ul and 25 ul using two different methods—The Qiagen MINELUTE® column method (referred to as ME method in figures) and the phenol-chloroform followed by EtOH precipitation method (referred to as PC method). The DNA was eluted in 35 ul of Elution buffer (0.1M Tris, pH 8) and 30 ul of the DNA was used to generate sequencing using the NEB library kit Number E6000B (New England BioLabs, Inc.). An end-repair step of library generation was not included in these preparations. End repair is typically used to produce blunt ends and phosphorylate the ends. Such end repair operations are believed to be unnecessary when working with most cfDNA.

Figure 7:
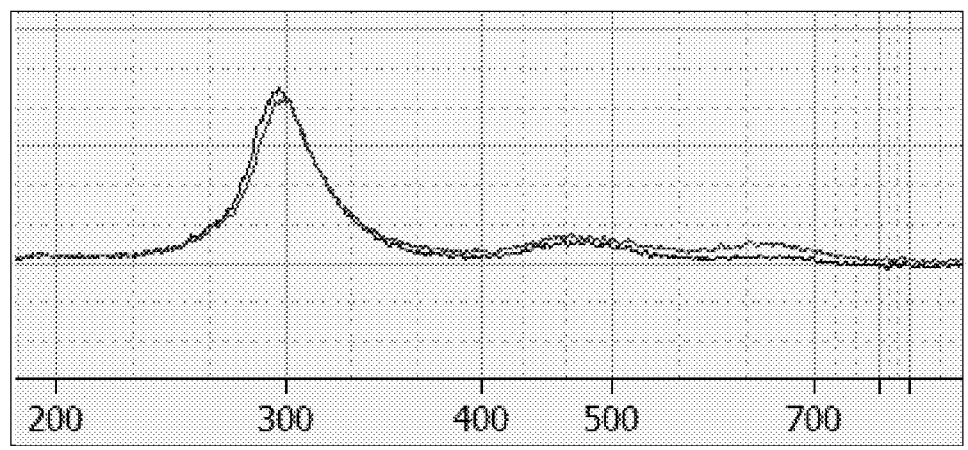
FIG. 7 shows an electropherogram showing identical library profiles on an Agilent BIOANALYZER® for sequencing libraries made starting with 50 ul plasma with the Qiagen MINELUTE® and the Phenol-Chloroform DNA isolation methods.

The table below shows the library yield in nM as a function of plasma volume input for the two cfDNA isolation techniques (ME and PC). FIG. 7 is an electropherogram showing identical library profiles on an Agilent BIOANA-LYZER® for sequencing libraries made starting with 50 ul plasma with the Qiagen MINELUTE® (trace with higher magnitude tail and with peak shifted down and toward right) and the Phenol-Chloroform (other trace) DNA isolation methods. The peak is associated with cfDNA having two adaptors appended thereto—each adaptor being about 60 bp in length.

TABLE 1

Library yield in nM as a function of plasma volume input
Library yield in nM

| Plasma ul | MINELUTE ® | Phe/CHCl$_3$ |
|---|---|---|
| 200 | 38.4 | 24.4 |
| 100 | 27.3 | 19.2 |
| 50 | 23.1 | 26.5 |
| 25 | 18.2 | 16.2 |

The sequencing libraries generated starting with 50 ul and 25 μl (microliters) plasma by both methods were sequenced on an Illumina GAII sequencer and various sequencing metrics were compared. The table below lists the certain metrics.

TABLE 2

Metrics of sequencing libraries generated by ME and PC methods

| Input | Reads | Tags | Tags/Reads | NonExcld Sites | NonExcld Sites/Tags |
|---|---|---|---|---|---|
| 50 ul plasma-ME | 31328834 | 13949959 | 0.4453 | 9547222 | 0.6844 |
| 25 ul plasma-ME | 30367943 | 10686615 | 0.3519 | 6188932 | 0.5791 |
| 50 ul plasma-PC | 30807636 | 11567337 | 0.3755 | 5886940 | 0.5089 |
| 25 ul plasma-PC | 25533994 | 10786944 | 0.4225 | 3381205 | 0.3135 |

Figure 8:
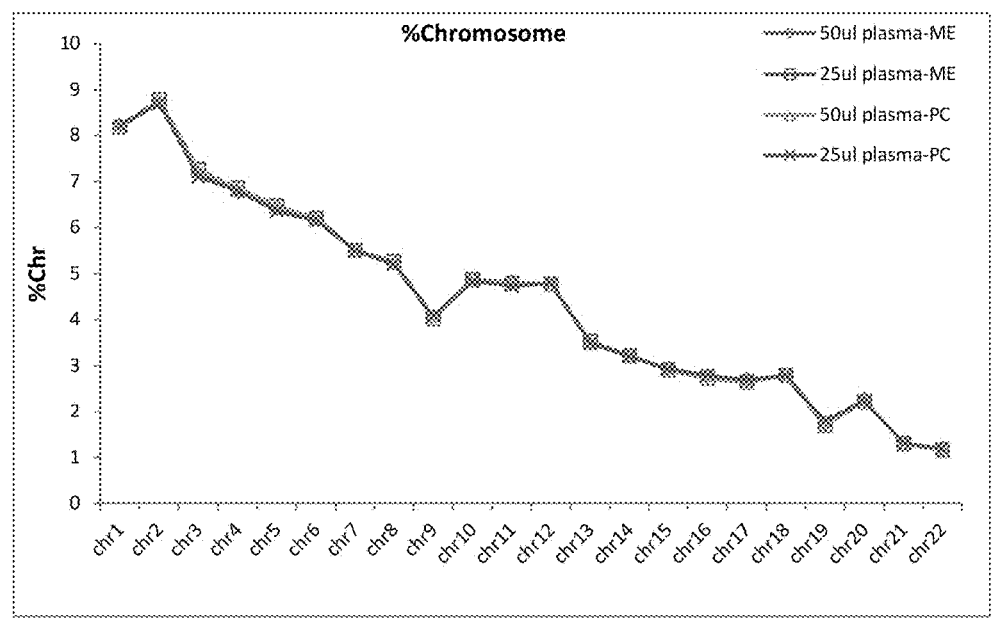
FIG. 8 shows that the % chromosome tags is invariant with lowering amounts of plasma input.

The reads are the short sequences output by the sequencer. The tags are reads that have been mapped to a non-excluded portion of the human genome. Non-excluded sites are sites on the genome that are not duplicated within the genome. As seen in the table above, cfDNA made from as little as 25 ul of plasma gave>$5 \times 10^6$ non-excluded sites on the GAII (see 25 ul plasma-ME condition). This shows that there is adequate cfDNA in as little as 25 ul of plasma to generate the minimum necessary unique, non-redundant sequencing tags for downstream analysis. Using the higher cfDNA recovery processes described herein, the 25 ul should be a sufficient sample size. FIG. 8 shows that the % chromosome tags is invariant with lowering amounts of plasma input, where the different symbols for different methods (ME and PC) and plasma amounts (25 and 50 ul) tend to overlap for each chromosome.

Generating Library Directly from Nucleosome-Attached cfDNA Using Adapter Ligation Method The data presented above shows that there is adequate DNA in 25 ul or more of plasma to generate workable sequencing library. The following description shows that a functioning library can be made directly from plasma.

As mentioned, untreated plasma contains a large amount of ambient protein, predominantly 35-50 mg/ml albumin and 10-15 mg/ml immunoglobulins. These proteins create steric hinderance for the library-making enzymes to act on nucleosomal cfDNA. Plasma also contains salts, proteases and nucleases that can interfere with the library biochemistry. Therefore, in working with plasma one may simplify its composition as follows: (1) deplete or reduce background albumins and Igs, (2) inhibit proteases and nucleases, and/or (3) make the cfDNA more accessible.

In certain embodiments, background protein can be depleted using a combination of albumin and Ig depletion columns. Many proteases and nucleases can be deactivated by heating the plasma to 65 deg for about 15-30 min OR using a blood collection tube such as a Streck tube (described above) to collect blood because Streck additive deactivates nucleases. Finally, the "ends" of cfDNA can be made more accessible to library preparations enzymes using mild detergents and salts (or a combination thereof). These will cause the cfDNA to unwrap from the histone complex, allowing access to the ends of the cfDNA for ligation of the sequencing adapters.

The data below describes implementation of such techniques to make library directly from plasma. As seen below, the yields of the library are acceptable and encouraging.

Figure 9:
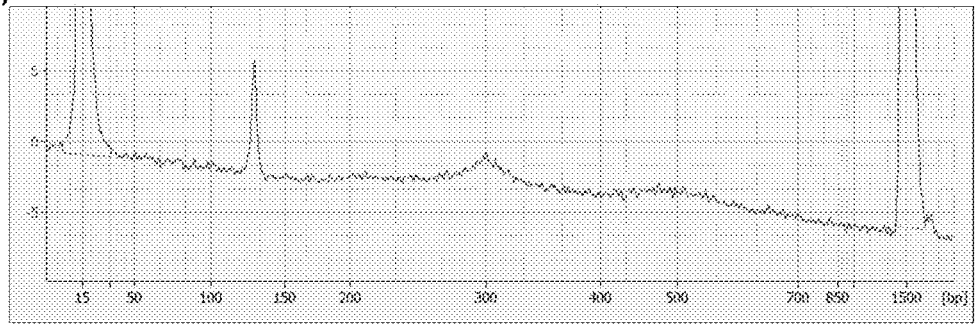
FIG. 9A shows a BIOANALYZER® profile of the library generated with a peak at the expected 300 bp size from the sample processed by protein depletion.
FIG. 9B shows a comparative BIOANALYZER® profiles of plasma samples treated with BRIJ®-35 (middle profile), NP40 (bottom profile) and TRITON®-X100 (top profile).
FIG. 9C shows a BIOANALYZER® profile of a plasma sample in the presence of 0.05% TWEEN®-20.
Figure 9:
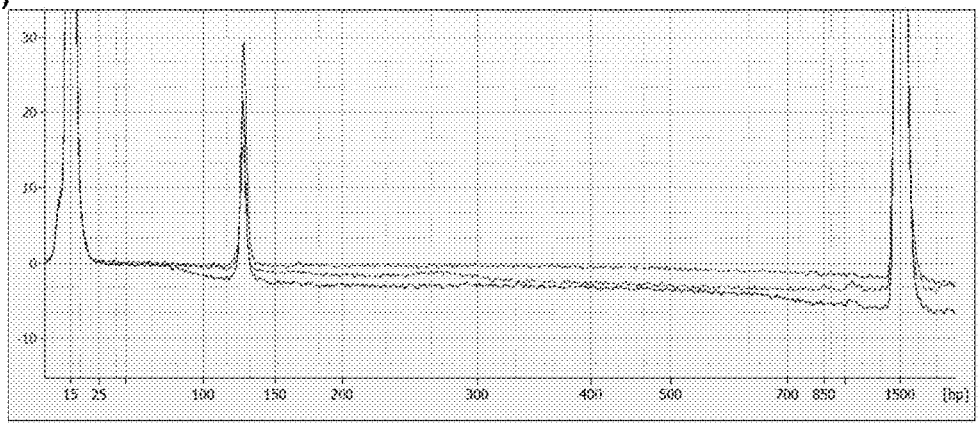
Figure 9:
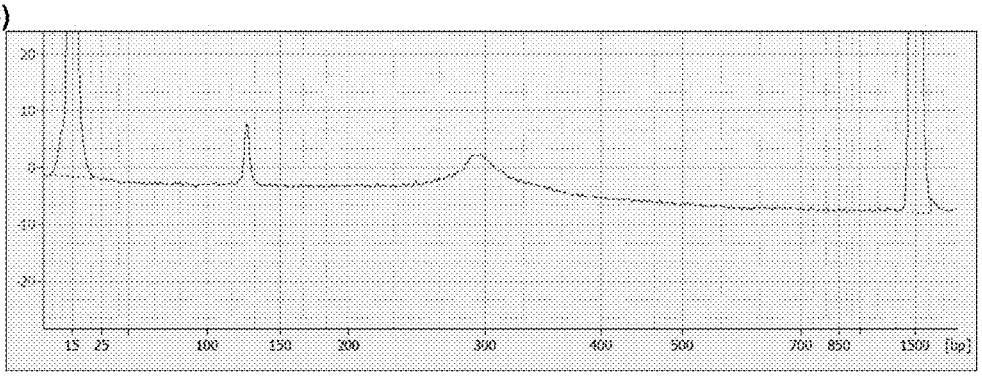

1) Plasma Protein Depletion:

50 ul plasma was heated to 65 deg C. for 20 min. The resulting cloudy plasma was centrifuged at 15,000 g for 5 minutes and the supernatant was taken into an end-repair-free NEB library preparation (identified above) with indexed Illumina adapter. FIG. 9A shows a BIOANALYZER® profile of the library generated with a peak at the expected 300 bp size from the sample processed by protein depletion. The concentration of DNA in this library was relatively small at 1 nM but the results demonstrate that cfDNA around nucleosomes can be adapter ligated. Moreover, the peak at ~120 bp, which represents the adapter dimer, confirmed that ligase is active in plasma.

2) Detergent Treatment of Plasma:

50 ul plasma was treated with one of various detergents (Tween-20, TRITON®-X100, BRIJ®-35, SDS, NP40 and combinations thereof) prior to attempting a library preparation. The concentrations of the detergents tested varied depending on the ionic/non-ionic character of the detergent. E.g., TWEEN®-20, BRIJ®-35 and NP40 were added at 0.1% and 0.5%; SDS and TRITON®-X100 were added at 0.01% and 0.05% (all percentages in wt/wt). The plasma used in these experiments was not depleted of excess protein. Untreated plasma and most detergents did not provide apparent library generation. FIG. 9B shows a comparative BIOANALYZER® profiles. In the profiles, there is no discernible library peak at 300 bp in plasma treated with BRIJ®-35 (middle profile), NP40 (bottom profile) and TRITON®-X100 (top profile). However, in all three conditions, there is a peak at 120 bp, showing that the ligase works (albeit inefficiently) in the plasma to generate the adapter dimer.

In contrast, as shown in FIG. 9C, plasma in the presence of 0.05% TWEEN®-20 generated a non-trivial library peak (concentration ~2.3 nM) at the expected 300 bp size.

This library was sequenced on the Illumina GAII, along with a control library where DNA was isolated form 50 ul of plasma using the Qiagen MINELUTE® column. Sequencing metrics and % Chr representation were compared.

The table below compared certain sequencing metrics. As is apparent from the data, the metrics of non-excluded sites and the ratio of such sites to tags (NES/Tags) are not great in the plasma library sample. This shows that the number of unique, non-redundant sequencing tags generated by the plasma library was not suitable in this experiment. This is to be expected because the concentration of the input library was only 2.3 nM.

TABLE 3

Library metrics for positive control and plasma library

| Condition | Reads | Tags | Tags/Reads | NonExcld Sites | NonExcld Sites/Tags |
|---|---|---|---|---|---|
| Positive control | 49701951 | 35281787 | 0.710 | 31056544 | 0.880 |
| Plasma lib (with Tw20) | 55174583 | 31690216 | 0.574 | 455059 | 0.014 |

Figure 10:
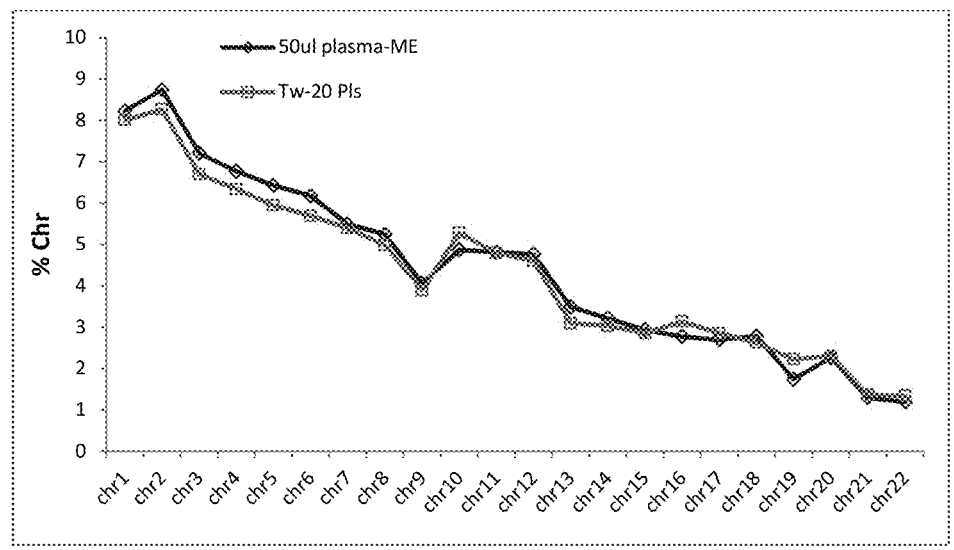
FIG. 10 shows the % Chr distribution from a control library made from purified DNA and that from a library generated directly from plasma.

FIG. 10 overlays the % Chr distribution from a control library made from purified DNA on the % Chr distribution from the library generated directly from plasma. The differences seen in the plasma library, especially in the number of tags on the smaller chromosomes, may be a result of an insufficient number of total tags from the plasma library as input. This data shows that it is feasible to make a sequencing library directly from plasma.

Method 2—Freezing and Thawing Whole Blood Samples

The example below describes a method for isolating cfDNA directly from blood without first isolating plasma. The example also details downstream experiments that demonstrate that cfDNA isolated from blood behaves similar to cfDNA isolated from plasma.

Materials and Methods

Freeze-Thaw Blood SN Isolation: Blood from 31 pregnant donors was collected in Streck BCTs, 4 tubes per donor. Upon arrival, three blood tubes were processed to plasma using conventional protocols. See Sehnert et al., *Optimal Detection of Fetal Chromosomal Abnormalities by Massively Parallel DNA Sequencing of Cell-Free Fetal DNA from Maternal Blood*, Clinical Chemistry 57: 7 (2011); and Bianchi et al., *Genome-Wide Fetal Aneuploidy Detection by Maternal Plasma DNA Sequencing*, Obstetrics and Gynecology, vol. 119, no. 5 (2012). The fourth tube of blood was placed inside a 50 ml conical tube and left lying on its side at −20° C., typically for approximately 16 hrs. Blood tubes lying on their sides did not break upon freezing and the 50 ml conical tube was used as a precautionary secondary container in case of the blood tube broke.

The following day, the frozen blood was thawed by leaving the blood tube in a room temperature water bath. 2.5 ml of each of the freeze-thawed blood was transferred to two Argos polypropylene tubes and centrifuged once at 16,000×g for 10 minutes. Two×1 ml of freeze-thawed blood supernatant were transferred from each Argos tube into Sarstedt cryotubes, resulting in four 1 ml tubes of freeze-thawed blood per donor.

cfDNA Isolation, Library Preparation and Sequencing

DNA isolation, library preparation, dilution and multiplexed sequencing were done following the conventional procedure mentioned above and described in Sehnert et al. and Bianchi et al., supra. 24 plasma and paired 24 freeze-thaw blood libraries were sequenced on a single flowcell (FC ID=C0UBVACXX).

Results

1) Comparison of cfDNA Yield:

DNA yield from freeze-thaw blood (FT) was substantially greater than the yield from plasma. However, encouragingly, only 6 of the 31 samples showed contamination from maternal cellular DNA.

Figure 11:
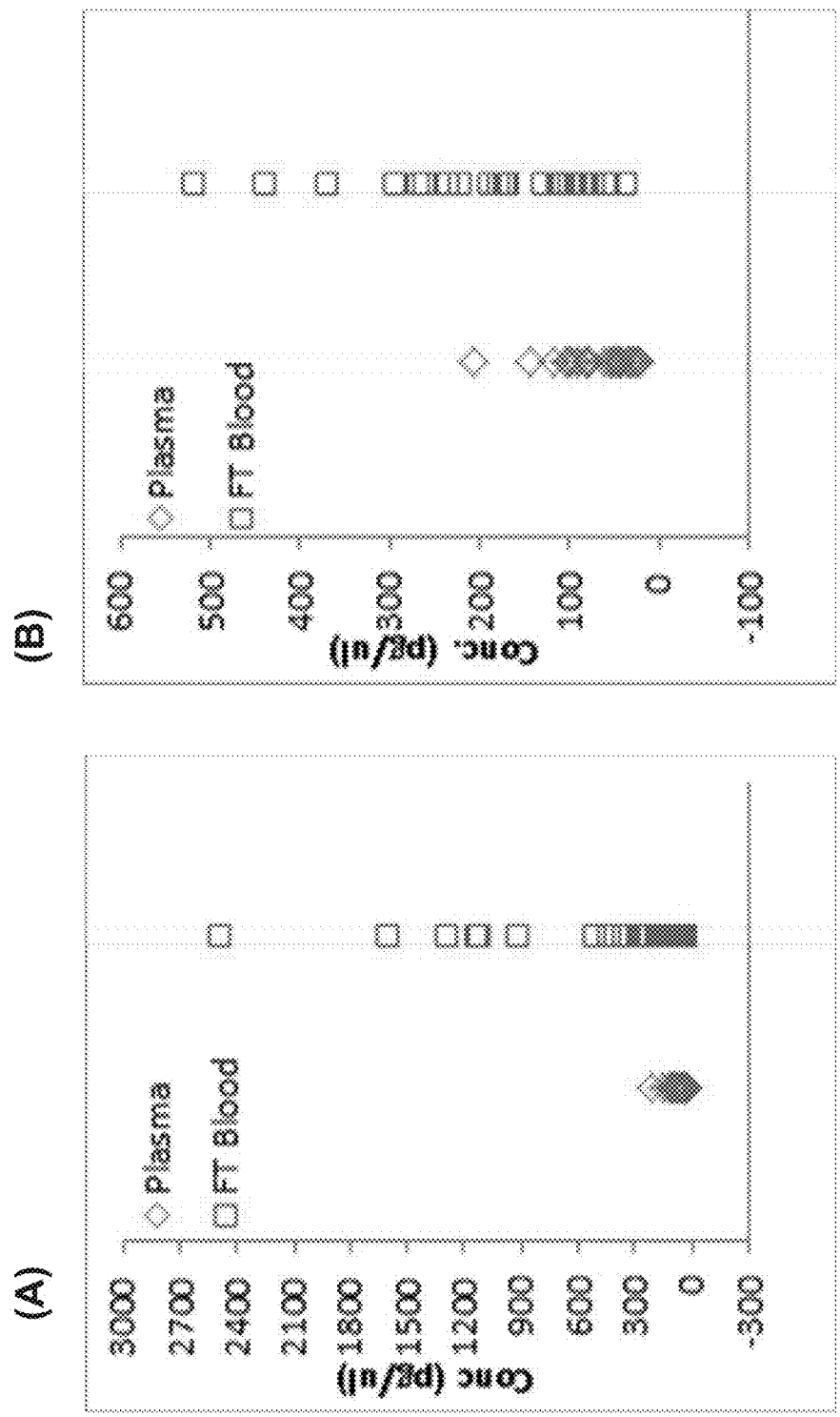
FIGS. 11A and 11B show the range of cfDNA concentrations measured for the 31 samples from FT Blood and plasma. The figures visualize comparison between DNA yield from plasma and yield from FT Blood.

FIGS. 11A and 11B show the range of cfDNA concentrations measured for the 31 samples from FT Blood and plasma. The figures visualizes comparison between DNA yield from plasma and yield from FT Blood. FIG. 11A shows all 31 samples, and FIG. 11B shows the same data without the 6 samples that had high DNA concentration to better visualize the pattern of data.

Figure 12:
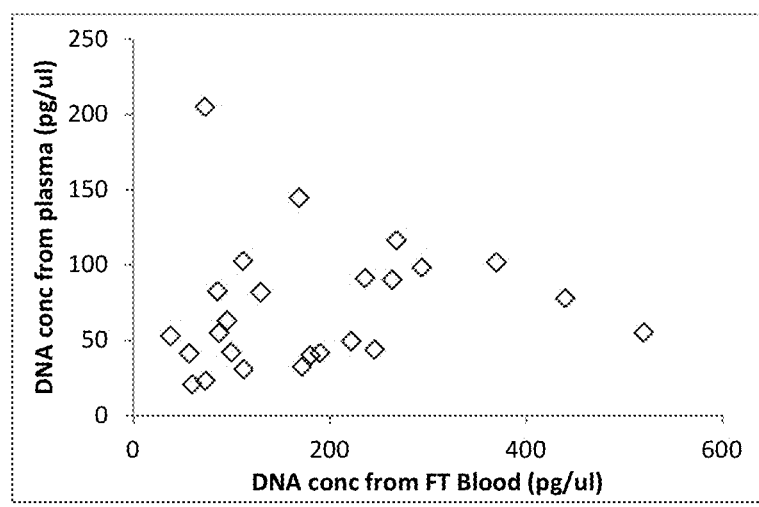
FIG. 12 shows the correlation between the two starting materials for DNA isolation, with the six outliers excluded (leaving 25 samples).

FIG. 12 shows the correlation between the two starting materials for DNA isolation, with the six outliers excluded (leaving 25 samples). As expected, there is no correlation between the two sources. This not surprising because previous data has shown that there is little correlation between DNA yields in the manual Qiagen Blood Mini kit process, even from the same target source.

In the approximately 20% of samples that show cellular DNA contamination, the contaminating DNA is typical of very high molecular weight DNA. Therefore, sample DNA can be treated to exclude high molecular weight DNA. There are various commercially available products such as SPRIselect Reagent Kit (Beckman Coulter), which can be fine-tuned to selectively retain DNA between predetermined sizes in any DNA preparation. Therefore, the problem of some samples of FT Blood DNA being contaminated with high MW DNA can be solved in a straight-forward manner.

2) Library Yield and Quality:

Indexed TruSeq (Illumina) libraries were generated from all 31 paired DNAs. However, when using cfDNA that had high cellular DNA contamination, the library profile looked different from the expected profile. High molecular weight cellular DNA shows up near and around the high marker (10,380 bp) in measurements made with High Sensitivity DNA chip (Agilent Technologies, Inc.). This is due to the interference of the high molecular weight DNA in the library process biochemistry.

Figure 13A:
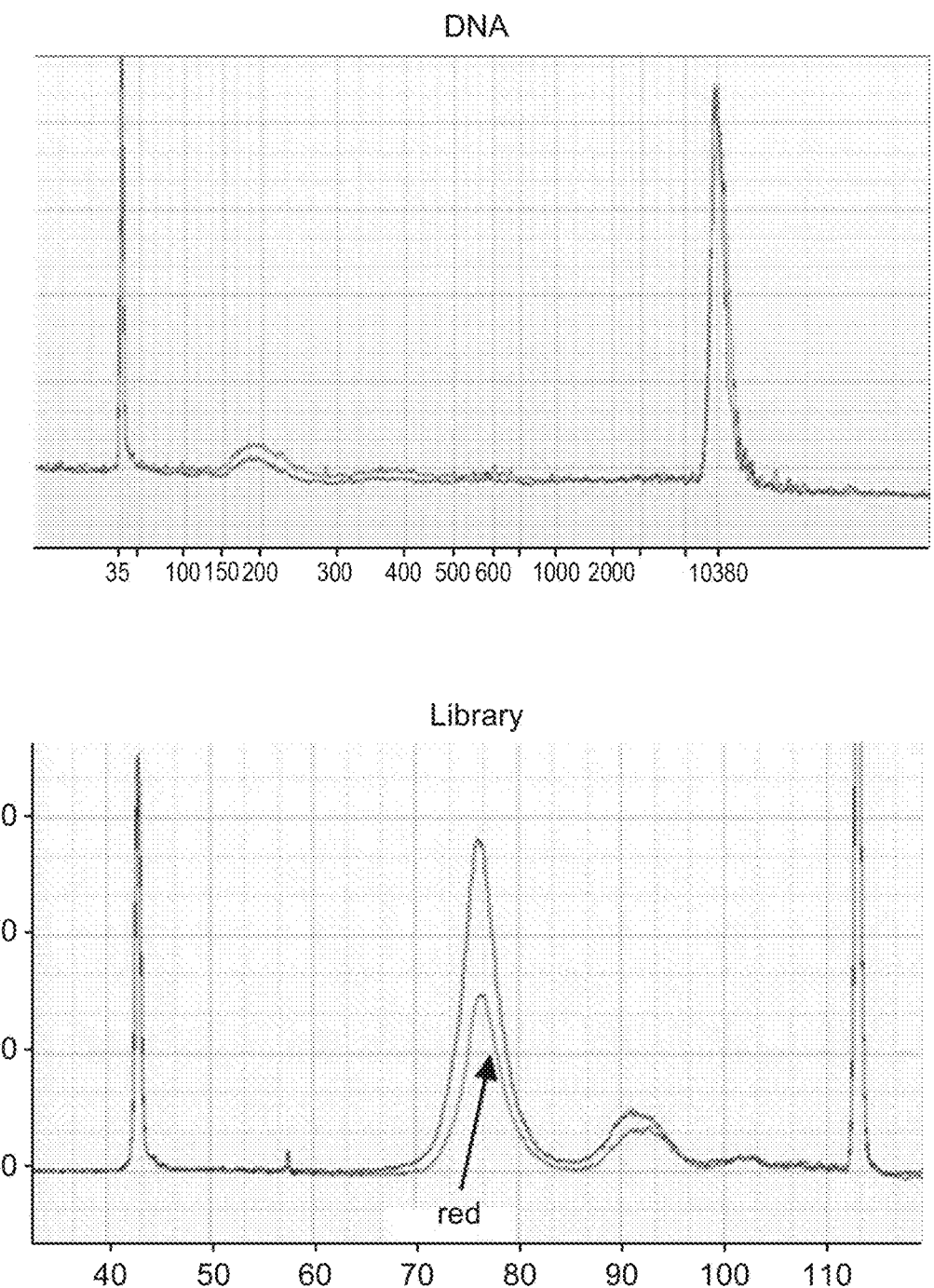
FIGS. 13A to 13C show DNA library profiles, demonstrating effect of HMW DNA contamination on library profile.
Figure 13B:
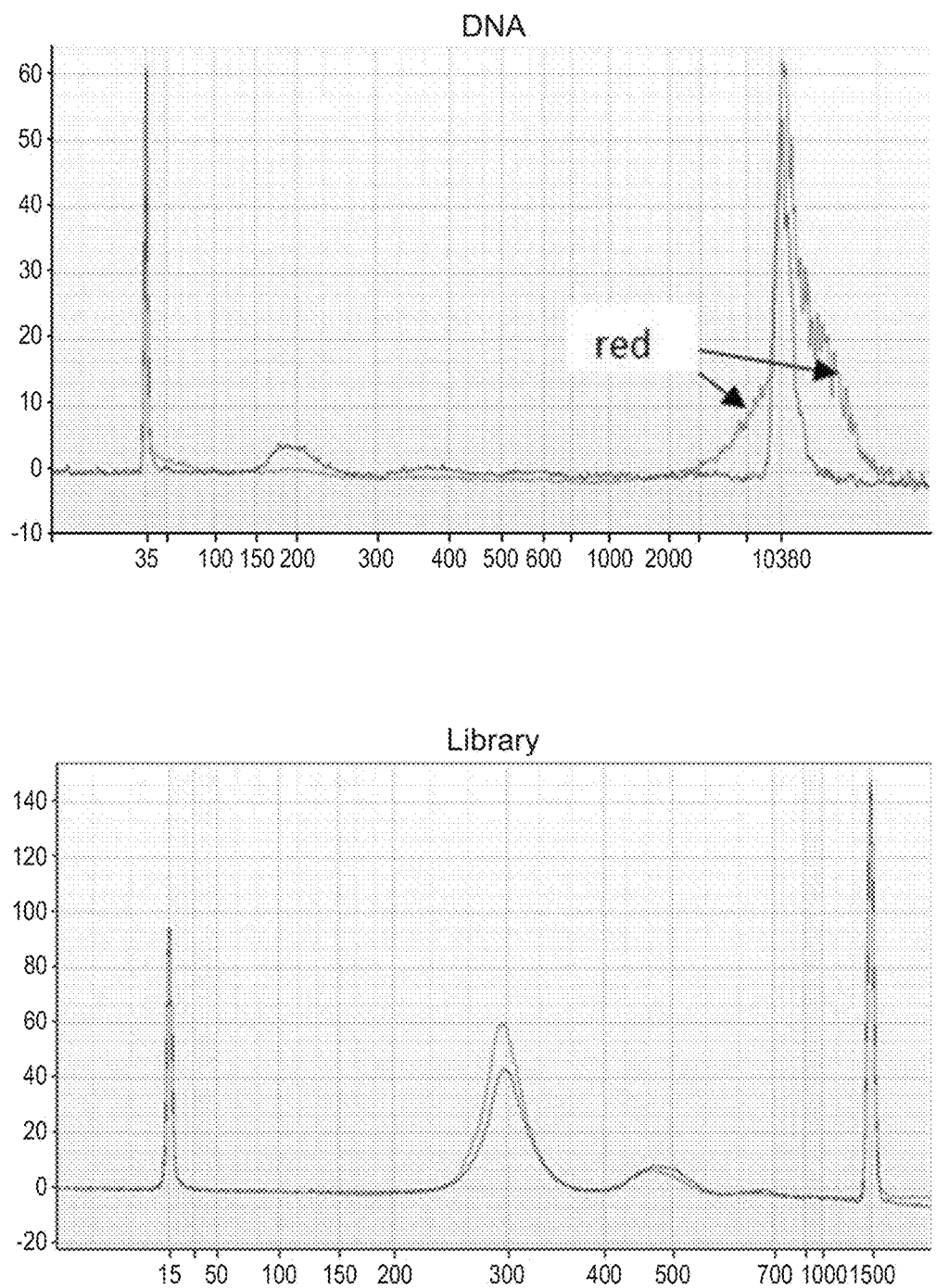
Figure 13C:
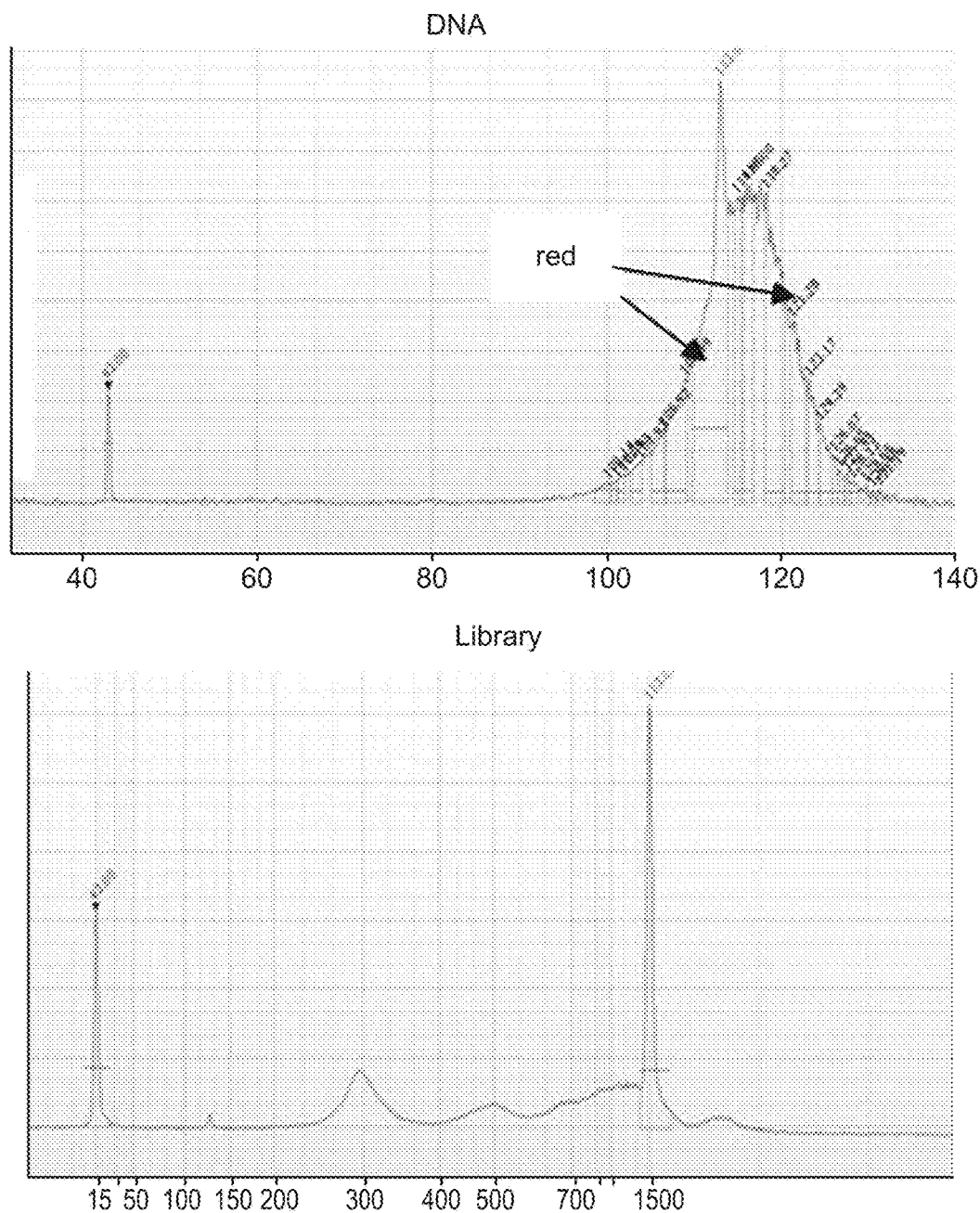

FIGS. 13A to 13C show DNA library profiles, demonstrating effect of HMW DNA contamination on library profile. FIGS. 13A and 13B compare three representative BIOANALYZER® profiles that detail the effect of the DNA quality on the library quality. Red traces represent DNA and libraries from FT blood and blue traces represent DNA and libraries from plasma. FIG. 13C shows one high DNA sample and the corresponding effect of the DNA concentration on the library yield and profile. DNA profiles on the BIOANALYZER® are from High Sensitivity chips; library profiles are from the DNA 1000 chips (Agilent Technologies, Inc.).

Figure 14:
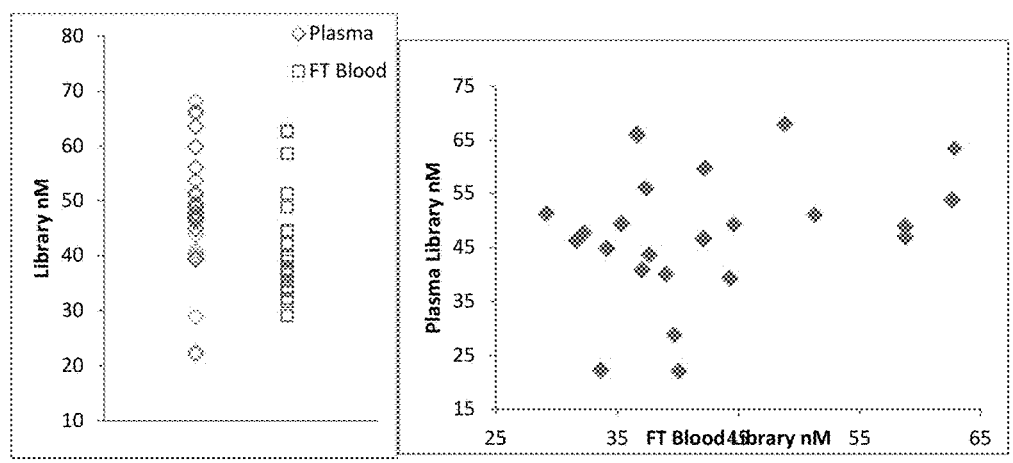
FIG. 14 shows comparative library yield range and correlation for 22 paired plasma and FT Blood cfDNAs.

FIG. 14 shows comparative library yield range and correlation for 22 paired plasma and FT Blood cfDNAs. The yield of the libraries was in an acceptable range of 20-75 nM. From the 31 paired samples, the six outliers with very high cellular DNA contamination in the FT Blood condition were not sent for sequencing; finally 22 of 25 were queued for sequencing.

The lack of correlation between the library yields for DNA form the two processes is not surprising. Each library process does not start with the same amount of input DNA.

Comparison of Sequencing Data Between FT Blood and Plasma Libraries:

Chromosome Plots:

The chromosome plots for FT Blood and plasma are slightly different as shown in FIG. 12. FT Blood libraries have slightly lower GC bias compared to plasma libraries as shown in FIG. 13. (chromosome 4 is the most AT rich chromosome, and chromosomes 19 and 22 are the most GC rich chromosomes). When % Chr hits are plotted versus Chr size, FT Blood has an $R^2$ of 0.977 vs. an $R^2$ of 0.973 for plasma.

Figure 15:
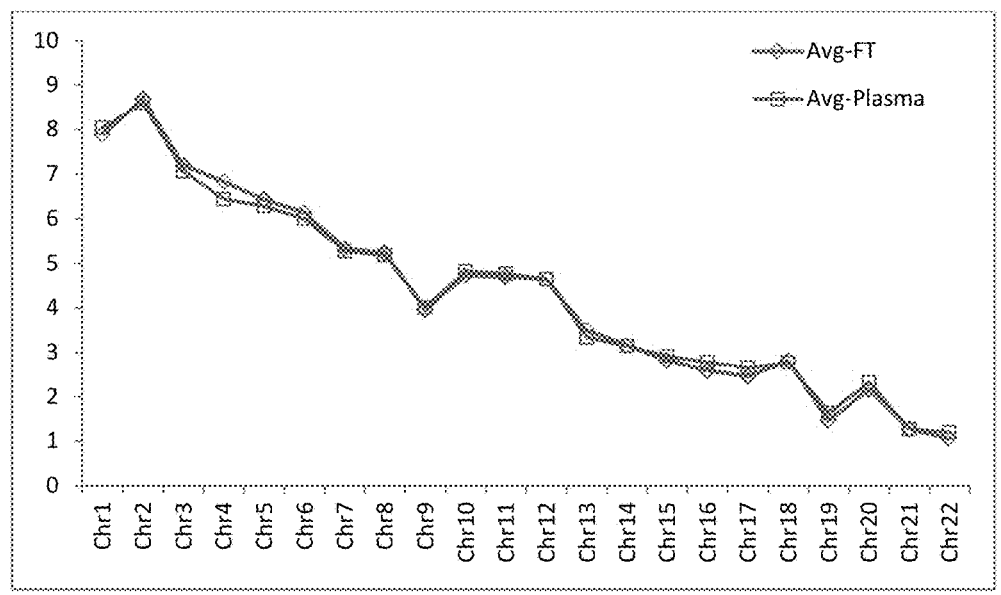
FIG. 15 shows % Chr for FT Blood vs. plasma libraries as a function of Chromosomes.
Figure 16:
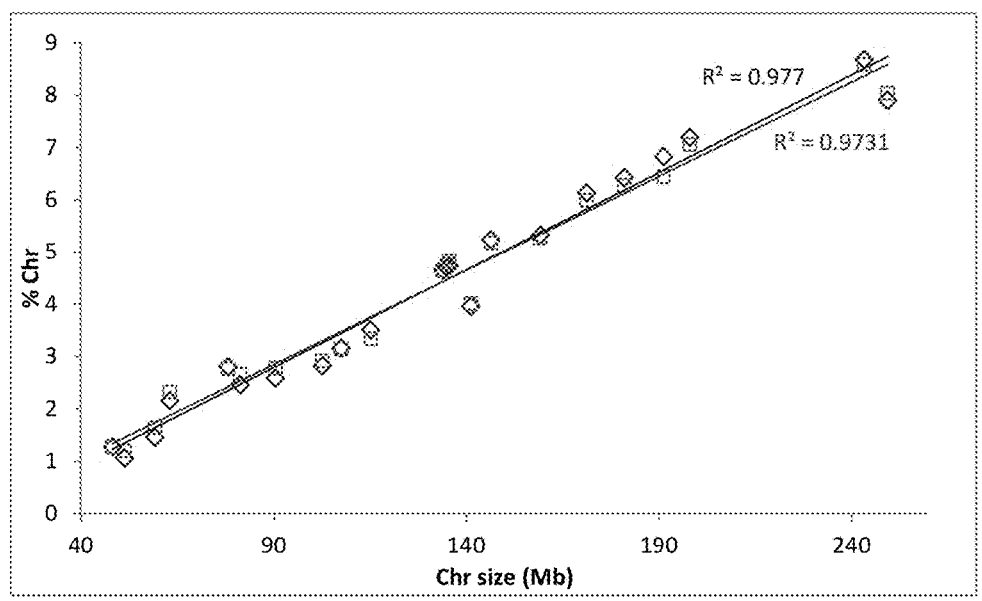
FIG. 16 shows % Chr plot as a function of Chr size (Mb) for the FT Blood and plasma conditions.

FIG. 15 shows % Chr for FT Blood vs. plasma libraries as a function of Chromosomes. FIG. 16 shows % Chr plot as a function of Chr size (Mb) for the FT Blood and plasma conditions.

Figure 17:
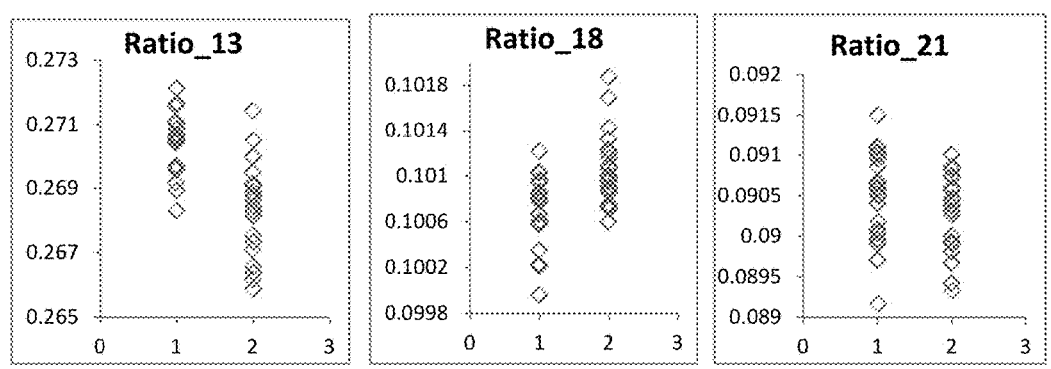
FIG. 17 shows the ratios reported for chromosomes 13, 18 and 21. Condition 1=FT Blood; condition 2=plasma.

Chromosome Ratios:

FIG. 17 shows the ratios reported for chromosomes 13, 18 and 21. Condition 1=FT Blood; condition 2=plasma. The ratios reported differ between the two conditions. The difference in the ratio values is due to the fact that the ratios for the FT Blood condition have not been calculated using the ideal chromosome densities (NCDs). However, the spread of the data is comparable.

Figure 18:
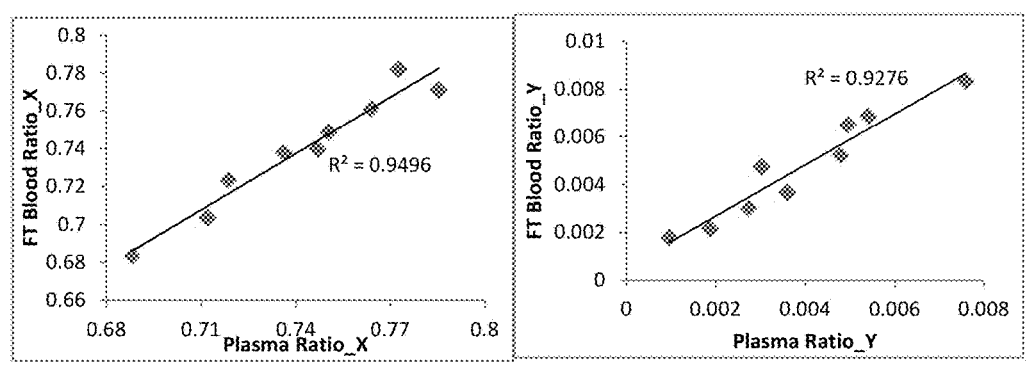
FIG. 18 shows correlation between FT Blood and Plasma for Ratio_X and Ratio_Y.

Fetal Fraction Representation:

Finally, the sequencing data showed that FT Blood did not compromise the calculation of fetal fraction in the DNA. FIG. 18 is a correlation plots between FT Blood and Plasma for Ratio_X and Ratio_Y. It shows that for the 9 pairs of putative male fetus samples among the 22 pairs sequenced, correlations for ChrX and for ChrY between the two conditions report high $R^2$ values of 0.9496 (ChrX) and 0.9296 (ChrY) respectively.

Freeze and then thawing blood is a viable technique for generating cfDNA libraries. Among the advantages it may offer are (1) decreased handling of the blood, (2) larger numbers of aliquots of the FT Blood will be available for downstream work, and (3) the concentrations of cfDNA isolated from FT Blood are typically higher. A potential disadvantage of using FT Blood is that in about 20% of the samples, there appears to be cellular DNA contamination. This can interfere with library biochemistry. However, the contaminating cellular DNA typically is very high molecular weight DNA. This can be removed by size selection, e.g. with a product such as SPRI Select. See Hawkins et al., supra. With the use of such products, the process can select for DNA within a prescribed size range.

Noninvasive Detection of Fetal Sub-Chromosome Abnormalities Using Deep Sequencing of Maternal Plasma The following example illustrates the kind of aneuploidy determinations that can be made from cfDNA. Although this work was not done using cfDNA unisolated from plasma, the process may be applied to cfDNA unisolated from plasma.

Artificial Mixtures

To determine the depth of sequencing needed to detect fetal sub-chromosome abnormalities i.e. partial aneuploidies, and to assess the effect of the relative fetal fraction of cfDNA present in a sample, artificial mixtures of 5% and 10% sheared genomic DNA were prepared using paired mother and child DNAs obtained from the Coriell Institute for Medical Research (Camden, N.J.). All children were males with karyotypes previously determined by metaphase cytogenetic analysis. The karyotypes of the four paired samples are shown in Table 4. The children's chromosome abnormalities were selected to represent different clinical scenarios, such as: a) whole chromosome aneuploidy (family 2139), b) sub-chromosomal deletion (family 1313), c) mosaic sub-chromosomal copy number change (family 2877, with an additional inherited deletion), and d) sub-chromosomal duplication (family 1925).

TABLE 4

| Coriell samples used to generate artificial mixtures | | | |
|---|---|---|---|
| FFamily ID | CCoriell ID | Member | Karyotype |
| 22139 | NNG09387 | Mother | 46, XX |
|  | NNG09394 | Affected Son | 47, XY, +21 |
| 11313 | NNA10924 | Mother | 46, XX |
|  | NNA10925 | Affected Son | 46, XY, del(7)(pter>p14::p12>qter) |
| 22877 | NNA22629 | Mother | 46, XX, del(11) |
|  | NNA22628 | Affected son | 47, XY, del(11)(pter–>p12::p11.2>qter), +15[12]/ |
|  |  |  | 46, XY, del(11)(pter–>p12::p11.2–>qter)[40] |

TABLE 4-continued

Coriell samples used to generate artificial mixtures

| FFamily ID | CCoriell ID | Member | Karyotype |
|---|---|---|---|
| 11925 | NNA16268 | Mother | 46, XX |
|  | NNA16363 | Unaffected twin son | 46, XY |
|  | NNA16362 | Affected twin son | 47, XY, +der(22) |

The genomic DNA samples were sheared to a size of ~200 bp using the Covaris S2 sonicator (Covaris, Woburn, Mass.) following the manufacturer's recommended protocols. DNA fragments smaller than 100 bp were removed using AmPure XP beads (Beckman Coulter Genomics, Danvers, Mass.). Sequencing libraries were generated with TruSeq v1 Sample Preparation kits (Illumina, San Diego, Calif.) from sheared DNA mixtures consisting of maternal DNA only and maternal+child DNA mixtures at 5% and 10% w/w. Samples were sequenced with single-ended 36 base pair (bp) reads on the Illumina HiSeq2000 instrument using TruSeq v3 chemistry. Each sample was sequenced on four lanes of a flow cell, resulting in $400 \times 10^6$ to $750 \times 10^6$ sequence tags per sample.

Maternal Plasma Samples

The MatErnal BLood IS Source to Accurately Diagnose Fetal Aneuploidy (MELISSA) trial was a registered clinical trial (NCT01122524) that recruited subjects and samples from 60 different centers in the United States and the corresponding metaphase karyotype results from an invasive prenatal diagnostic procedure. The study was designed to prospectively determine the accuracy of MPS (massively parallel sequencing) to detect whole chromosome fetal aneuploidy. During this trial, all samples with any abnormal karyotype were included to emulate the real clinical scenarios in which the fetal karyotype is not known at the time of sample acquisition. The results of this study have been previously published. Following completion of the MELISSA trial, the study database was assessed to identify ten samples that had complex karyotypes, including sub-chromosome abnormalities, material of unknown origin, or a marker chromosome (Table 5); also added was one MELISSA study sample with trisomy 20 as a control of performance in detection of whole chromosome aneuploidy. The karyotypes were performed for clinical indications and reflected local protocols. For example, some samples were analyzed with chromosome microarrays and some had metaphase analysis with or without FISH studies.

In the MELISSA study libraries were sequenced using single-end reads of 36 bp with 6 samples in a lane on an Illumina HiSeq2000 using TruSeq v2.5 chemistry. In the present example, the previously generated MELISSA libraries were re-sequenced using TruSeq v3 chemistry on an Illumina HiSeq 2000 with single-end reads of 25 bp. In this example, each of the 11 maternal samples was sequenced utilizing an entire flow cell, resulting in $600 \times 10^6$ to $1.3 \times 10^9$ sequence tags per sample. All sequencing was performed in the Verinata Health research laboratory (Redwood City, Calif.) by research laboratory personnel who were blinded to the fetal karyotype.

TABLE 5

Karyotypes of clinical samples analyzed by MPS. Samples in the last four rows are mosaic karyotypes

| PPatient ID | Specimen | Procedure | Karyotype |
|---|---|---|---|
| C60715 | Chorionic villi | Metaphase and 20q12 FISH | 47,XX,+20 |
| C65104 | Cultured villi | Metaphase, 6q12, 6q16.3 FISH and microarray | arr 6q12q16.3(64,075, 795-101,594,105)x3, 6q16.3(102,176,578-102,827,691)x3 |
| C61154 | Chorionic villi | Metaphase | 46, XY, del(7)(q36.1) |
| C61731 | Amniocytes | Metaphase and 22q FISH | 46,XX, del(8) (p23.1p23.2) |
| C62228 | Chorionic villi | Metaphase and Chr 15 FISH | 45, XX,-15, der(21) t (15;21) (q15;p11.2) |
| C60193 | Amniocytes | Metaphase | 46, XY, add(10)(q26) |
| C61233 | Amniocytes | Metaphase | 46, XX, add (X) (p22.1) |
| C61183 | Amniocytes | Metaphase and FISH | 46, XY or 46,XY, add(15)(p11.2) |
| C65664 | Amniocytes | Metaphase | mos 46,XY, +i(20) (q10)[8]/46,XY[17] |
| C66515 | Chorionic villi | Metaphase and FISH | 47,XY,+der(14 or 22)[10]/46,XY[10] |
| C60552 | Chorionic Villi | Metaphase | 47,XX+mar [12]/46, XX[8] |

Normalization and Analysis

Sequence reads were aligned to the human genome assembly hg19 obtained from the UCSC database (hgdownload.cse.ucsc.edu/goldenPath/hg19/bigZips/). Alignments were carried out utilizing the Bowtie short read aligner (version 0.12.5), allowing for up to two base mismatches during alignment. Only reads that unambiguously mapped to a single genomic location were included. Genomic sites at which reads mapped were counted as tags. Regions on the Y chromosome at which sequence tags from male and female samples mapped without any discrimination were excluded from the analysis (specifically, from base 0 to base $2 \times 10^6$; base $10 \times 10^6$ to base $13 \times 10^6$; and base $23 \times 10^6$ to the end of chromosome Y).

The genome was then further divided into 1 Mb and 100 kb bins and, for each sample, tags from both the positive and negative strand were assigned to individual bins for further analysis. The GC percentage of each bin was determined and bins were ranked by GC percentage across the entire genome. Each bin was individually normalized by calculating the ratio of tags within a bin to the sum of the number of tags in the 10 bins with the nearest GC percentages by equation (1):

$$BRV_{ij} = \frac{Tags_{ij}}{\Sigma Tags_{km}} \quad \text{Equation 1}$$

Where $BRV_{ij}$ is the "Bin Ratio Value" for the $j^{th}$ bin of chromosome i, and $Tags_{ij}$ is the number of tags in the $j^{th}$ bin of chromosome i. The sum runs over the 10 bins for the 1 Mb data and 40 bins for the 100 kb data for bins (km) with the nearest GC percentage to bin ij. In order to detect any sub-chromosomal differences, each of the BRVs were examined for deviations from the median values measured across multiple samples. The medians were determined from the four maternal only DNAs (Table 4) for the artificial samples and from the eleven maternal plasma samples (Table 5) for the clinical samples and were robust to individual sub-chromosome variants that might have been present in any one of the samples. Median absolute deviations (MADs) were calculated for each bin based on the medians and adjusted assuming a normal distribution for the number of tags in each bin. The adjusted MADs (aMADs) were utilized to calculate a z-score for each bin by equation (2):

$$z_{ij} = \frac{(BRV_{ij} - BRV_{Median_{ij}})}{aMAD_{ij}} \quad \text{Equation 2}$$

It was expected that $z_{ij}$ would be approximately ±3 for regions without any copy number variations (CNVs) and significantly greater than 3 when fetal CNVs were present. The $z_{ij}$ values can be utilized to determine the relative fetal fraction (ff) present in the cfDNA. The value can then be compared to an independent measurement of ff to validate copy number detection, or suggest the presence of mosaicism. For a bin ratio containing a copy number change from normal, the $BRV_{ij}$ will increase (in the case of a duplication) or decrease (in the case of a deletion) by equation (3):

$$BRV_{ij} = \left(1 \pm \frac{ff_n}{2}\right) BRV_{Median_{ij}} \quad \text{Equation 3}$$

In this equation, $ff_n$ is the fetal fraction for sample n. If the coefficient of variation for each bin, $CV_{ij}$ is defined as equation (4):

$$CV_{ij} = \frac{aMAD_{ij}}{BRV_{Median_{ij}}} \quad \text{Equation 4}$$

then equation (5)

$$ff_n = \text{abs}(2 z_{ij} CV_{ij}) \quad \text{Equation 5}$$

can be used to calculate $ff_n$ for sample n from $z_{ij}$ values when a CNV is present.

Detection of a sub-chromosomal abnormality was a multi-step process for classifying specific regions as having a copy number variant. The $z_{ij}$±4 thresholds are indicated in each figure by a dashed horizontal line. In step 1, $z_{ij}$ values from the 1 Mb bins that exceeded ±4 were identified. The calculated ff was then utilized and bins that had a ff of less than 4% were eliminated. For the samples with male fetuses, the ff was also calculated using all of the bins in chromosome X. This value was compared to the result obtained for putative copy number changes to validate a copy number change or suggest a mosaic result. Finally, in cases of a single 1 Mb bin that met the above criteria, the 100 kb bins data were examined and it was required that at least 2 bins (within a contiguous group of 4) indicated a $z_{ij}$ value that exceeded +4 or -4 before classifying a sample as having a copy number variant. All three criteria had to be fulfilled to classify the copy number variant. For example, individual data points that only had a z-score of greater than or less than 4 but did not meet the additional criteria were not classified as copy number variants.

Results

Artificial Mixtures

Whole Chromosome Aneuploidy of Chromosome 21

Figure 19:
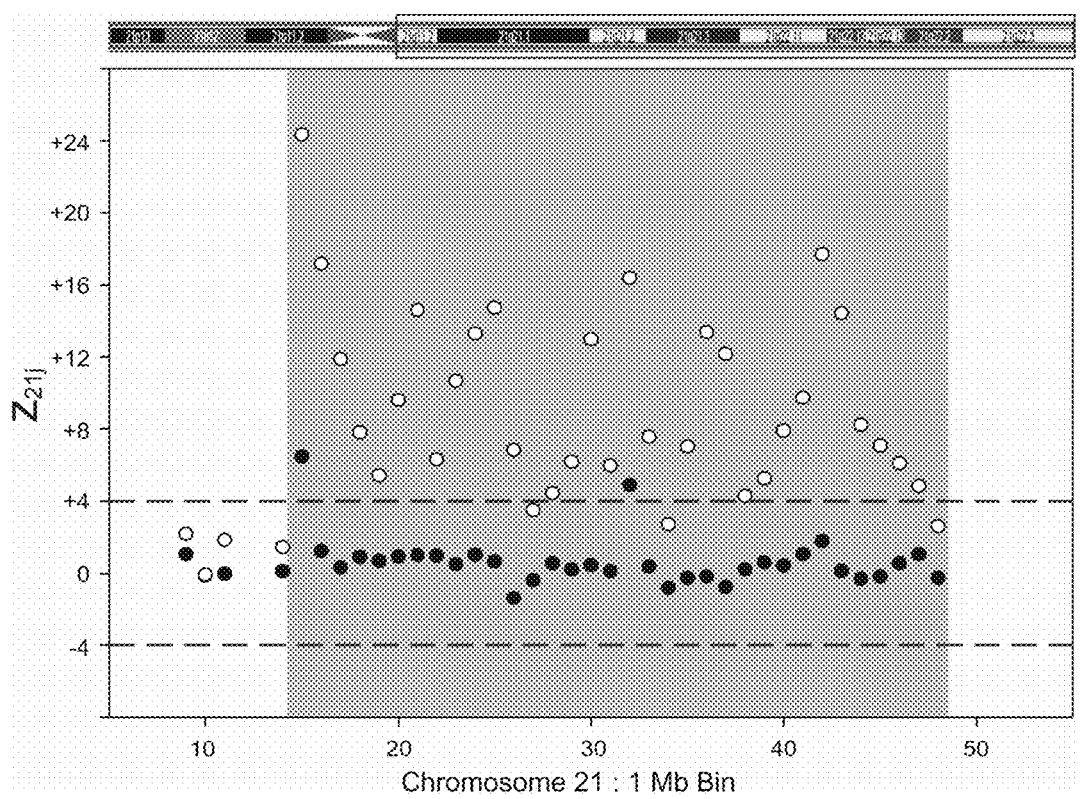
FIG. 19 shows the family 2139 $z_{21j}$ 1 Mb bin results for Chr 21 with 0% (solid circles) and 10% (empty circles) mixtures of the affected son's DNA mixed with the mother's DNA.

FIG. 19 shows the chromosome 21 $z_{21j}$ values (1 Mb bins) for an artificial mixture of family 2139 with 10% of the son's DNA (T21) mixed with the mother's DNA. In chromosome 21, there are approximately 38 Mb (35 Mb in the q arm) that contain unique reference genome sequence in hg19. All of the chromosome 21 tags mapped to this region. With the exception of the first 4 Mb, FIG. 19 shows an over-representation of most of chromosome 21 in the 10% mixture, as would be expected with a full chromosome aneuploidy. Using equation 5 to calculate the ff from the average $z_{21j}$ values of the amplified regions, ffs of 7.0% and 12.7%, for the 5% and 10% mixtures, respectively, were obtained. Calculating the ff average using $z_{Xj}$ values, ffs of 4.2% and 9.0%, for the 5% and 10% mixtures, respectively, were obtained.

Sub-Chromosomal Deletion of Chromosome 7

Figure 20:
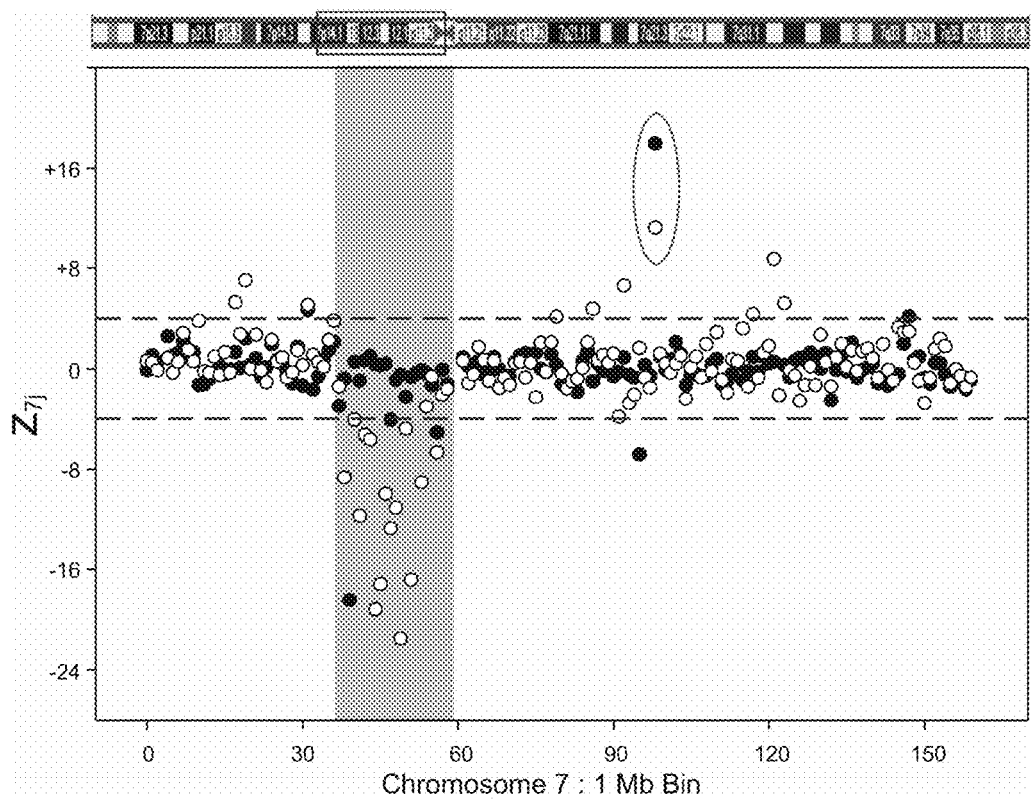
FIG. 20 shows the family 1313 $z_{7j}$ 1 Mb bin results for Chr 7 with 0% (solid circles) and 10% (empty circles) mixtures of the affected son's DNA mixed with the mother's DNA.

The method was next tested on Family 1313, in which the son has a sub-chromosomal deletion of chromosome 7. FIG. 20 shows the chromosome 7 $z_{7j}$ values (1 Mb bins) for the maternal sample mixed with 10% of her son's DNA. A deletion was observed beginning at bin 38 and continuing to bin 58. This reflects the approximately 20 Mb deletion documented in the metaphase karyotype. Fetal fraction values ffs of 6.1% and 10.5% were calculated for the 5% and 10% mixtures, respectively, for this sample. Calculating the ff average using $z_{Xj}$ values, ffs of 5.9% and 10.4% were obtained, respectively. Interestingly in this sample there appeared to be a duplication in the maternal sample at bin 98 of chromosome 7 (circle in FIG. 20), which did not appear in the son, i.e. was not inherited. Had this duplication been maternally inherited, the $z_{7j}$ value would be expected to decrease also in the mixture. As shown in FIG. 20, the value of $z_{7j}$ is lower for the 10% mixture compared to the pure maternal sample. Bin 2 which had very high $z_{72}$ values of 43.9 and 28.5 for the maternal sample and 10% mixture, respectively (data not shown) also appeared to reflect a maternal duplication.

Mosaic Duplication of Chromosome 15

Figure 21:
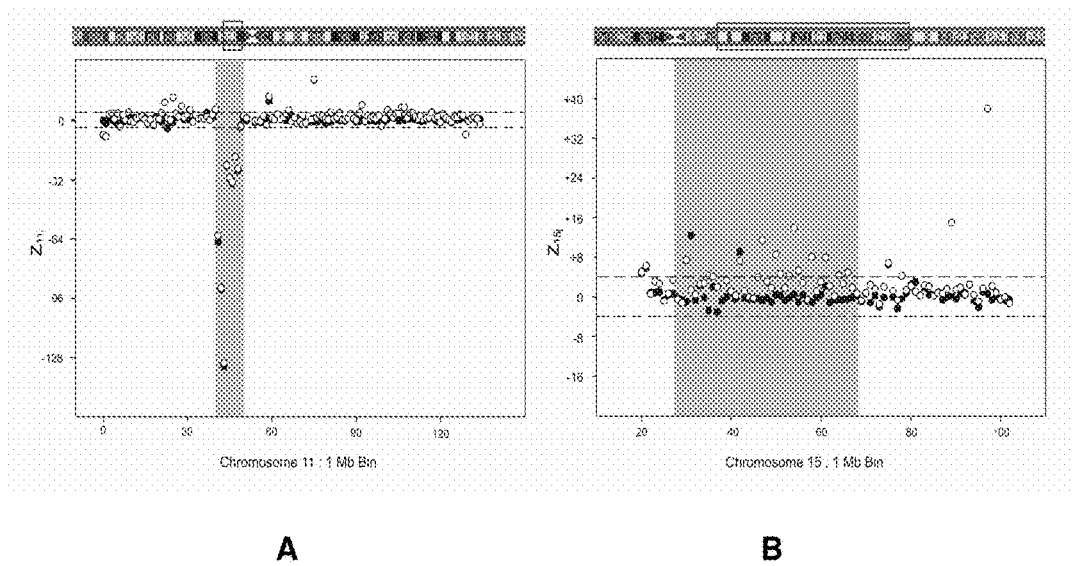
FIG. 21 (A-B) shows the family 2877 $z_{ij}$ 1 Mb bin results for Chr 11 and 15 with 0% (solid circles) and 10% (empty circles) mixtures of the affected son's DNA mixed with the mother's DNA.

In Family 2877, the maternal sample has a deletion in chromosome 11 that was inherited by the son. In addition, the son has a duplication in chromosome 15 that was not maternally inherited, and is part of a mosaic karyotype in which the majority of cells are normal (Table 4). FIG. 21 shows both the chromosome 11 and chromosome 15 $z_{ij}$ values for the 1 Mb bins in the mixture with 10% of the son's DNA. As expected, the inherited deletion in chromosome 11 from 41 Mb to 49 Mb had a consistent set of values that did not change with fetal fraction. However, the chromosome 15 duplication was clearly detected between bins 27 and 66, albeit with more noise than observed in the other artificial samples. The noise results from the reduced apparent ff for this duplication due to the mosaicism. The ffs calculated from the duplication using 15 $z_{ij}$ values were 1.6% and 3.0% for the 5% and 10% mixtures, respectively. In contrast, the ffs calculated from chromosome X were 5.3% and 10.7%. The method was able to detect both the sub-chromosomal duplication with the low mosaic ff and to distinguish that the duplication was due to mosaicism by comparison of the ff result to an independent measurement of chromosome X.

Duplications of Chromosome 22

Figure 22:
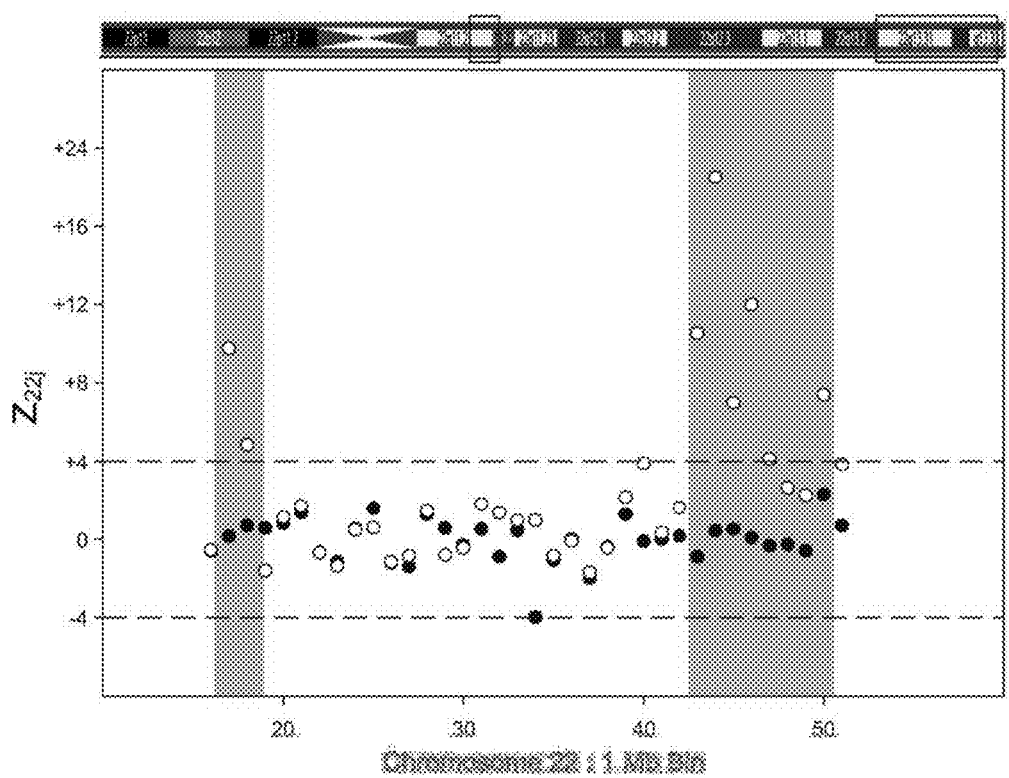
FIG. 22 shows the clinical sample C1925 $z_{22j}$ 1 Mb bin results for Chr 22 with 0% (solid circles) and 10% (empty circles) mixture of the affected son's DNA mixed with the mother's DNA. The 2 Mb and the 8 Mb duplications from the son in the DNA mixture are shown.

Family 1925 consisted of a mother and two male twins, one of which had two duplications of different sizes in chromosome 22. Ten percent mixtures of the affected twin's DNA and the mother were sequenced. The results indicated a 2 Mb and an 8 Mb duplication at bins 17 and 43, respectively. The ff for 10% mixture was calculated to be 11.2% from the 2 Mb duplication, 11.6% from the 8 Mb duplication, and 9.8% from chromosome X (FIG. 22).

Maternal Plasma Samples

Whole Chromosome Aneuploidy

Sample C60715 was previously reported in MELISSA study as detected for trisomy 20. The 1 Mb bin results for this sample contain ~960 million tags across the genome. The extra copy of chromosome 20 was clearly detected and the ff calculated from the 1 Mb bin data is 4.4%, in agreement with the whole chromosome results.

Duplications and Deletions

Figure 23A:
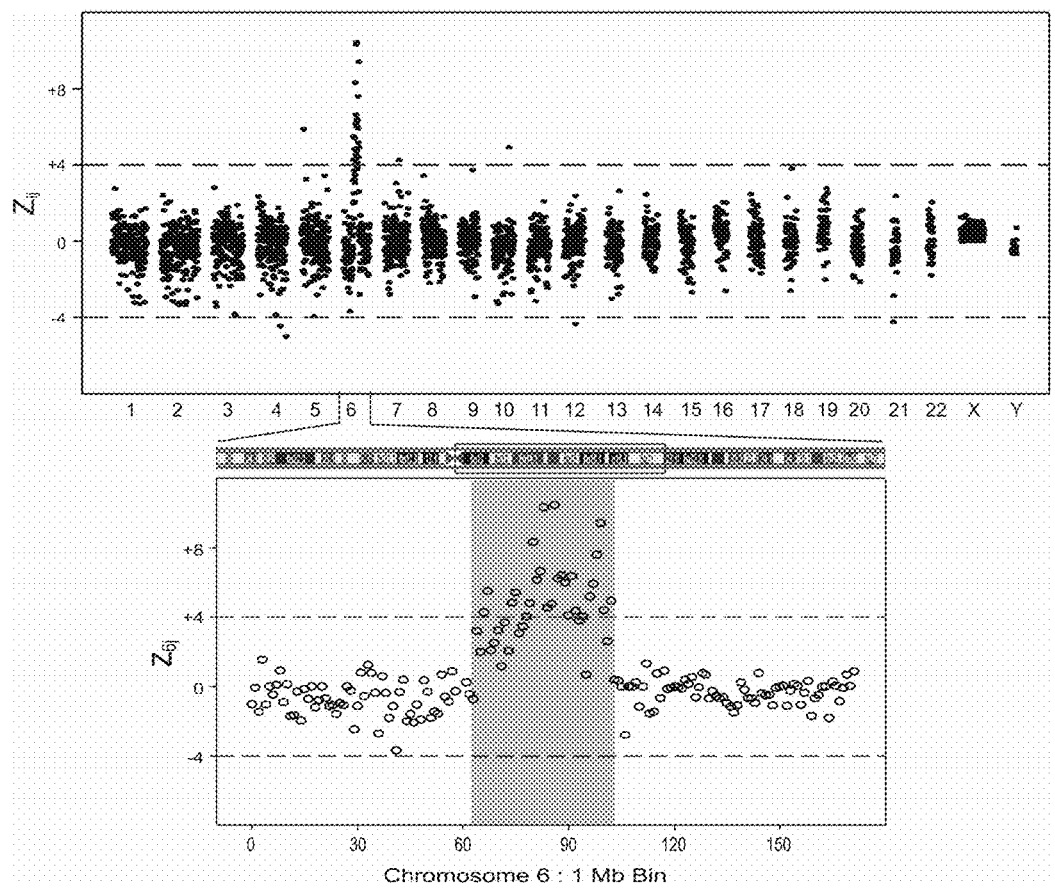
FIG. 23 (A-B) shows clinical sample C65104 $z_{ij}$ 1 Mb bin results with a karyotype with duplication in chromosome 6. Expanded regions show $z_{6j}$ 1 Mb bin and 100 kb bin results.
Figure 23B:
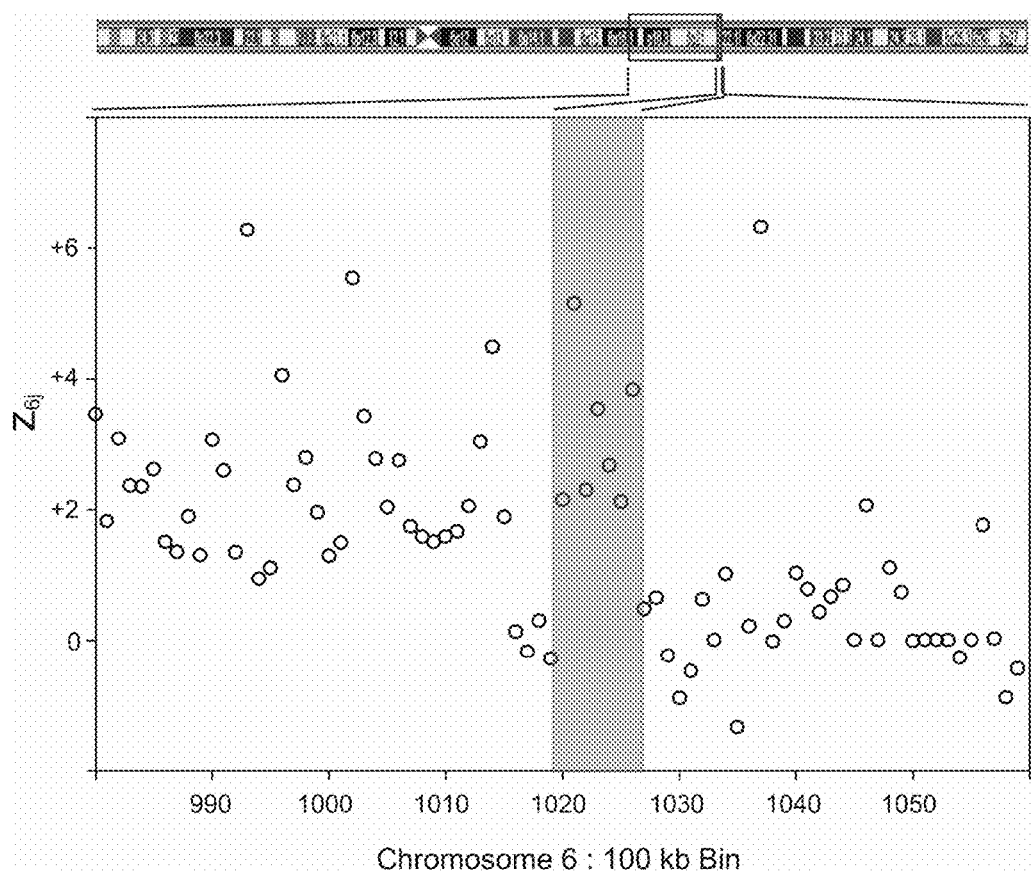

Sample C65104 (Table 6) had a complex fetal karyotype that involved the long arm of chromosome 6 (6q) and two duplications, one of which was 38 Mb in size. The second duplication was reported as approximately 650 kb from the chromosome microarray analysis of cultured villi. Using MPS it was previously reported that this sample showed an increased whole chromosome normalized chromosome value (NCV) in chromosome 6 (NCV=3.6) (Bianchi, D. W., Platt, L. D., Goldberg, J. D., Abuhamad, A., Sehnert, A. J., Rava, R. P. (2012). Genome-wide fetal aneuploidy detection by maternal plasma DNA sequencing. Obstet. Gynecol. 119, 890-901). This value was insufficient to classify this sample as having a full chromosome aneuploidy, but it was consistent with the presence of a large duplication. FIG. 23A shows the 1 Mb bin results for this sample showing the z values as NCV for the chromosomes. All the chromosomes other than chromosome 6 showed z values that clustered around 0. By focusing only on chromosome 6 (FIG. 23A), the exact region of the 38 Mb duplication was identified. This 38 Mb corresponded to the large duplication seen in the microarray karyotype, and the ff calculated from this duplication was 11.9%. The second duplication in the microarray karyotype was not detected a priori by our criteria; however, it can be clearly seen in the 100 kb bin expansion of the region (FIG. 23A). Improved analytic methodology and/or deeper sequencing would clearly allow this duplication to be detected. Finally, a 300 kb gain in chromosome 7 at 7q22.1 was also identified by MPS in agreement with the microarray results (Table 31).

TABLE 6

MPS results on clinical samples that are congruent with the clinically reported karyotype

| Pat ID | Affected Chr | Gain/ Loss | Start bin | End bin | Size (Mbp) | Chromosome region |
|---|---|---|---|---|---|---|
| C60715 | 22 | Gain | 87.3 | 87.9 | 0.6 | 2p11.2 |
| | 22 | Loss | 89.8 | 90.2 | 0.5 | 2p11.2 |
| C61154 | 88 | Loss | 46.9 | 47.7 | 0.9 | 8q11.1 |
| C60193 | 77 | Loss | 158.7 | 158.9 | 0.3 | 7q36.3 |
| C61233 | 33 | Loss | 114 | 114.5 | 0.6 | 3q13.31 |
| | 111 | Loss | 55.3 | 55.4 | 0.2 | 11q11 |
| | 117 | GGain | 81 | 81.1 | 0.2 | 17q25.3 |
| C61183 | 11 | Loss | 12.8 | 13 | 0.3 | 1p36.21 |
| C65664 | 77 | Loss | 39.3 | 40 | 0.8 | 7p14.1 |
| | 114 | Loss | 58 | 58.1 | 0.2 | 14q23.1 |
| C66515 | 99 | Gain | 40.7 | 41 | 0.4 | 9p31.1 |
| C60552 | 66 | Loss | 151.4 | 151.5 | 0.2 | 6q25.1 |
| | 222 | Gain | 25.6 | 25.9 | 0.4 | 22q11.23 |

Figure 24A:
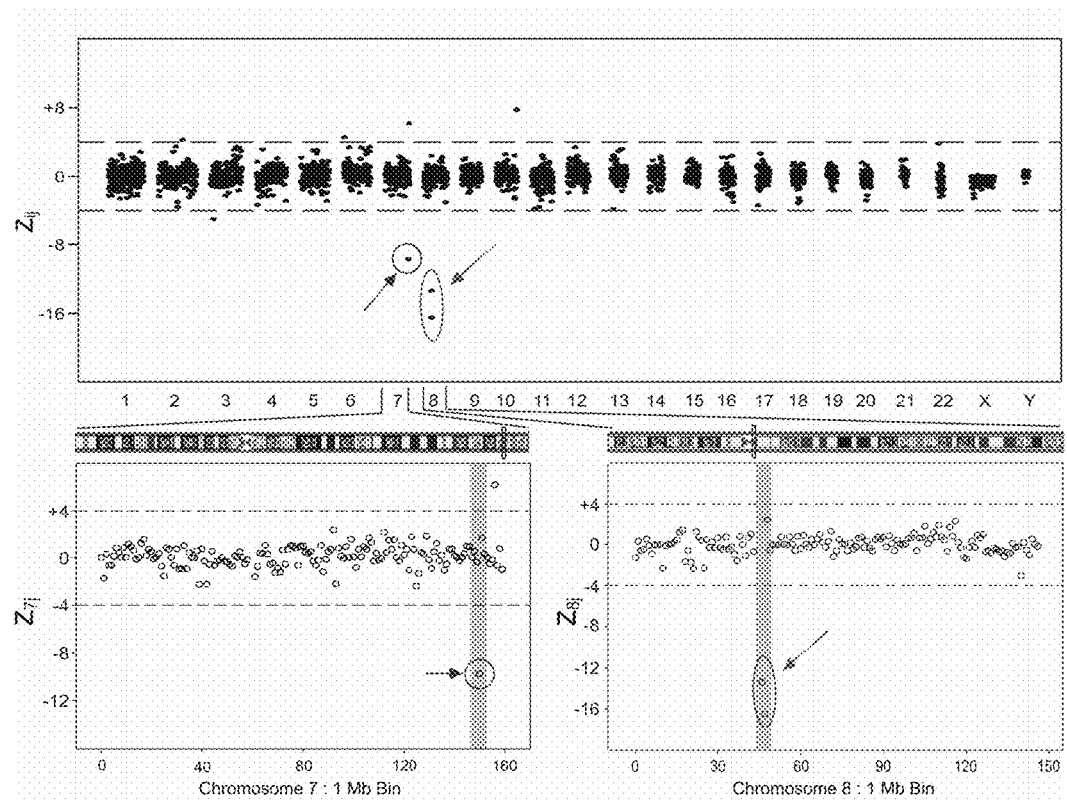
FIG. 24(A-B) shows the clinical sample C61154 $z_{ij}$ 1 Mb bin results across the genome for clinical sample with a karyotype with a small deletion in chromosome 7 (circled). Another small deletion is detected in chromosome 8 (circled). Expanded regions show $z_{7j}$ and $z_{8j}$ 100 kb bin data.
Figure 24B:
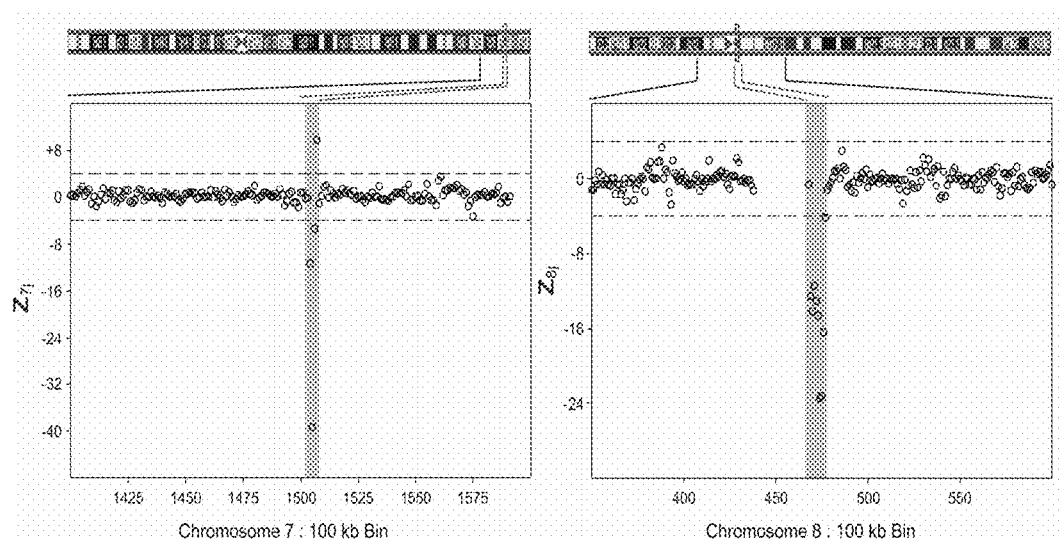

Sample C61154 came from a pregnant woman carrying a fetus with a7q36.1 deletion detected by metaphase karyotype analysis of chorionic villi. FIG. 24A shows the 1 Mb bin results for this sample. Only chromosomes 7 and 8 showed 1 Mb bins with z values that met the criteria for classification. Chromosome 7 showed a single 1 Mb bin with a significant decrease in the z value at 7q36.1 (denoted by circle in FIG. 24A). An examination of the data at higher resolution (100 kb bins) (FIG. 24B) showed a deletion of approximately 300 kb, which was consistent with the karyotype report (Table 6). In this sample it was also observed an approximately 1 Mb deletion in both the 1 Mb and 100 kb bin data close to the centromere of chromosome 8 (as shown by the oval in FIG. 24A). The chromosome 8 deletion was not reported in the karyotype obtained from chorionic villi (Table 7). The ffs calculated from the chromosome 7 and 8 deletions were 18.4% and 68.5%, respectively. The ff calculated from chromosome X was 2.8%. In this case, the high ff value for chromosome 8 indicated that this deletion, which was not reported in the fetal metaphase karyotype, was maternal in origin. In addition, the discordant value of the chromosome 7 compared to chromosome X ff values suggests that part of the signal could be due to the mother. The karyotype report indicated that the chromosome 7 "abnormality is most likely a derivative from a carrier parent," which is consistent with the MPS data.

Figure 25:
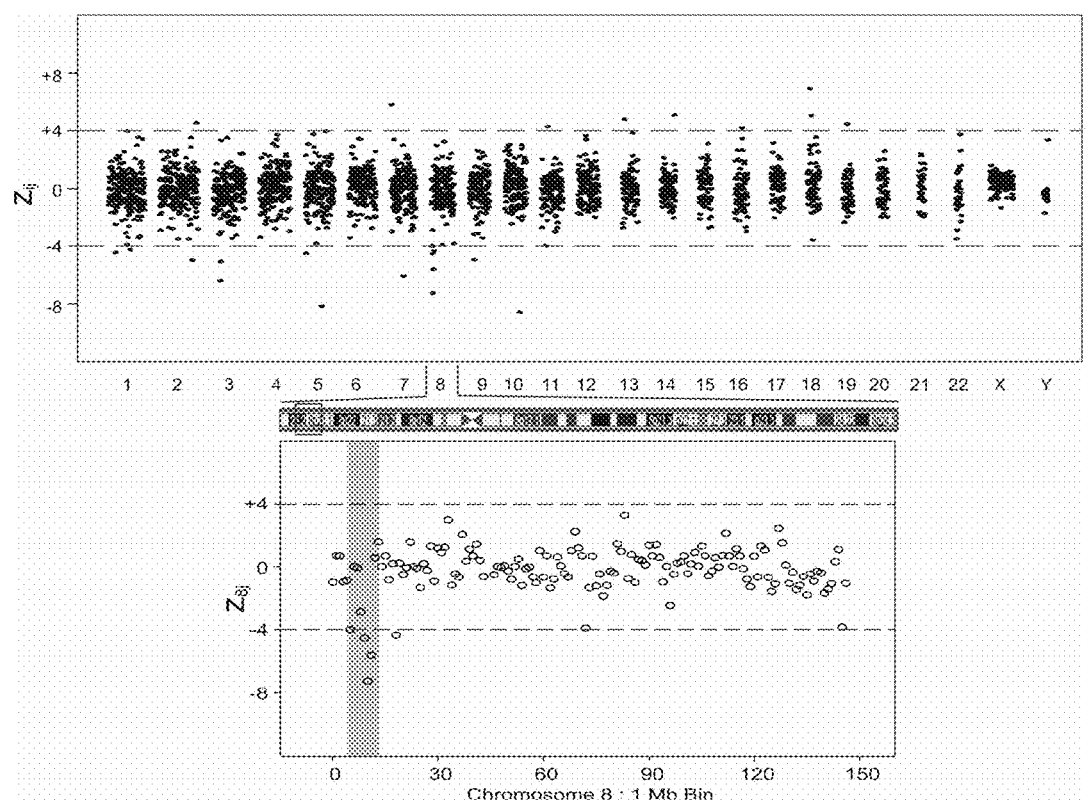
FIG. 25 shows the clinical sample C61731 $z_{ij}$ 1 Mb bin results across the genome for clinical sample with a karyotype with a small deletion in chromosome 8. Expanded region show $z_{8j}$ 1 Mb bin data.

Sample C61731 had a partial deletion of the short arm of chromosome 8. The 1 Mb bin results (FIG. 25) indicated an approximately 5 Mb deletion in the p-arm of chromosome 8 in agreement with the karyotype (Table 6). The fetal fraction calculated from this chromosome deletion was 8.4%.

Translocations

Figure 26:
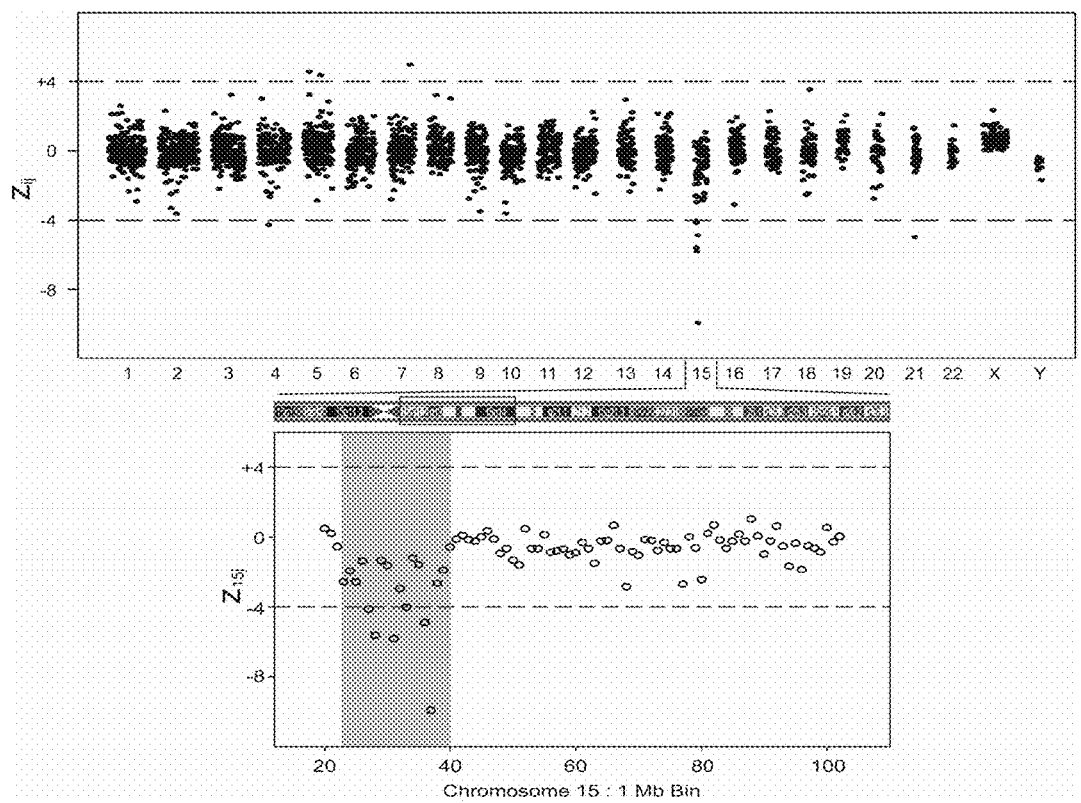
FIG. 26 shows the clinical sample C62228 $z_{ij}$ 1 Mb bin results across the genome for clinical sample with a karyotype with a deletion in chromosome 15. Expanded region show $z_{15j}$ 1 Mb bin data.

The fetal karyotype for sample C62228 showed an unbalanced translocation consisting of 45, XX,-15, der(21) t (15; 21) (q15; p11.2). The 1 Mb bin results for this sample are shown in FIG. 26. There was a clear 17 Mb deletion in chromosome 15 in agreement with the karyotype (Table 6). The ff calculated from the chromosome 15 deletion was 11.3%. No sub-chromosomal abnormalities were detected in the chromosome 21 data to indicate the translocation breakpoint.

Identification of Additional Material Not Identified by Karyotype

Figure 27:
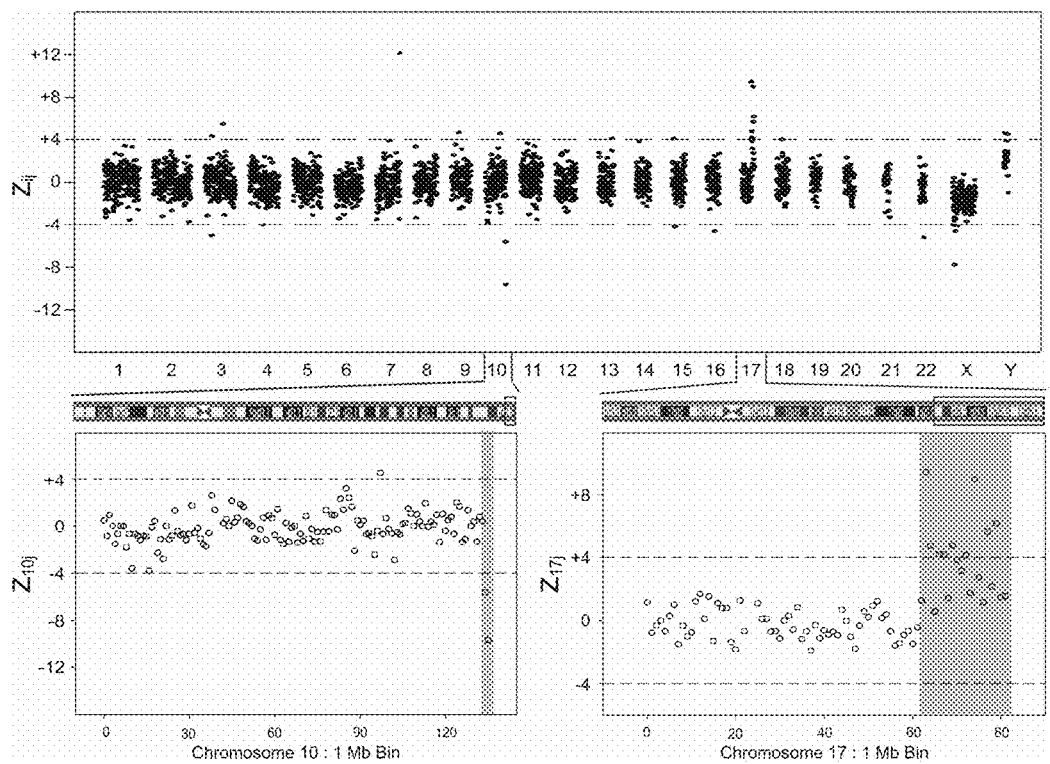
FIG. 27 shows the clinical sample C61093 $z_{ij}$ 1 Mb bin results across the genome with a karyotype 46, XY, add(10) (q26). Expanded regions show $z_{10j}$ and $z_{17j}$ 1 Mb bin data.

Two maternal samples had fetal karyotypes with added material of unknown origin at specific chromosomes. The 1 Mb bin results for sample C60193 are shown in FIG. 27. From the MPS data, the additional material of unknown origin on the long arm of chromosome 10 appeared to be derived from an approximately 19 Mb duplication at the q terminus of chromosome 17. There was also an approximately 2 Mb deletion at the q terminus of chromosome 10 that was confirmed by the 100 kb bin data. The ffs calculated from the chromosome 17 duplication and chromosome X (male fetus) were 12.5% and 9.4%, respectively. The 2 Mb deletion on chromosome 10 had a calculated ff of 19.4%. Finally, the MPS results for this sample indicated a small (300 kb) deletion in chromosome 7 that was not reported in the metaphase karyotype (Table 7).

Figure 28:
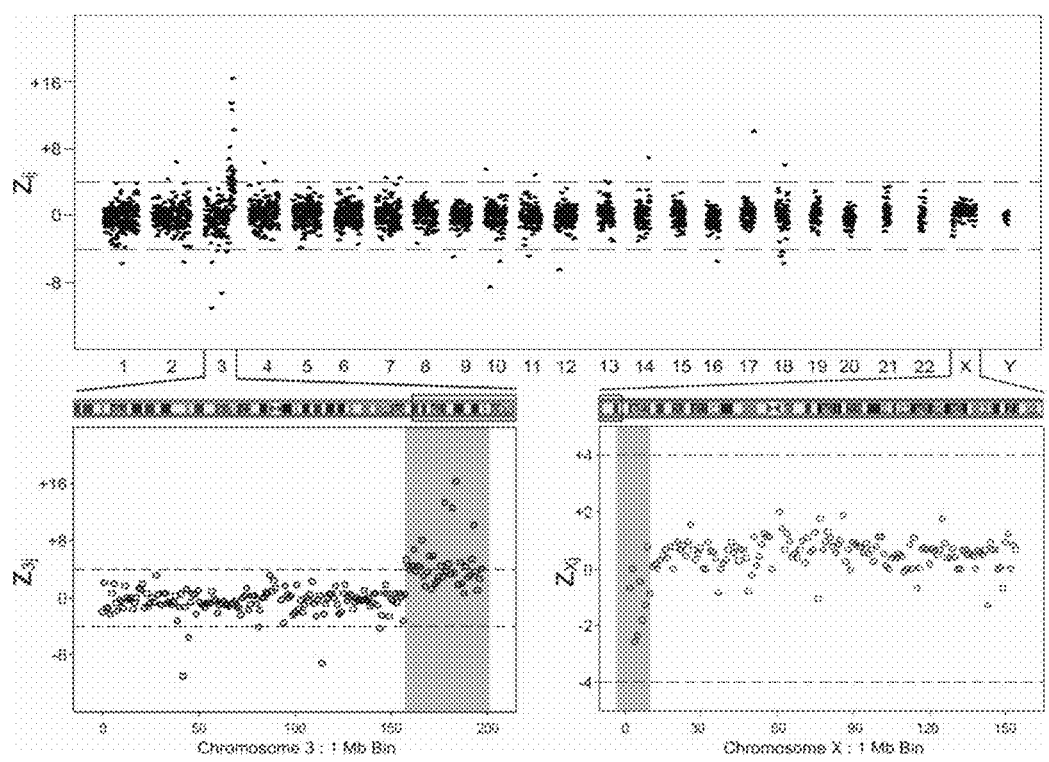
FIG. 28 shows the clinical sample C61233 $z_{ij}$ 1 Mb bin results across the genome with a karyotype 46,XX,add(X) (p22.1). Expanded regions show z3j and zXj 1 Mb bin data. The figures show a 40 Mb-long duplication of the region from 158 Mb to 198 Mb on Chr 3 and a 9 Mb-long deletion on Chr X from 1 Mb to 10 Mb (although the signal from this deletion did not meet our criteria for classifying it as a CNV).

The 1 Mb bin results for sample C61233 are shown in FIG. 28. The karyotype for this sample indicated additional chromosomal material on the short arm of one of the X chromosomes. The additional material of unknown origin appeared to originate from a 40 Mb duplication at the q terminus of chromosome 3. There was also an approximately 9 Mb deletion on the p arm of chromosome X (Table 6). The ffs calculated from the chromosome 3 duplication and chromosome X deletion were 9.5% and 6.7%, respectively. The MPS results for this sample also indicated three small sub-chromosomal changes that were not reported in the metaphase karyotype (Table 7).

TABLE 7

Copy number variants detected by MPS that were not reported in the clinical karyotypes

| Pat ID | Affected Chr | Gain/Loss | Start bin | End bin | Size (Mbp) | Chromosome region |
|---|---|---|---|---|---|---|
| C60715 | 22 | Gain | 87.3 | 87.9 | 0.6 | 2p11.2 |
|  | 22 | Loss | 89.8 | 90.2 | 0.5 | 2p11.2 |
| C61154 | 88 | Loss | 46.9 | 47.7 | 0.9 | 8q11.1 |
| C60193 | 77 | Loss | 158.7 | 158.9 | 0.3 | 7q36.3 |
| C61233 | 33 | Loss | 114 | 114.5 | 0.6 | 3q13.31 |
|  | 111 | Loss | 55.3 | 55.4 | 0.2 | 11q11 |
|  | 117 | GGain | 81 | 81.1 | 0.2 | 17q25.3 |
| C61183 | 11 | Loss | 12.8 | 13 | 0.3 | 1p36.21 |
| C65664 | 77 | Loss | 39.3 | 40 | 0.8 | 7p14.1 |
|  | 114 | Loss | 58 | 58.1 | 0.2 | 14q23.1 |
| C66515 | 99 | Gain | 40.7 | 41 | 0.4 | 9p31.1 |
| C60552 | 66 | Loss | 151.4 | 151.5 | 0.2 | 6q25.1 |
|  | 222 | Gain | 25.6 | 25.9 | 0.4 | 22q11.23 |

Mosaic Karyotypes

Four of the samples listed in Table 5 (C61183, C65664, C66515, C60552) had mosaic karyotypes with sub-chromosomal abnormalities. Unfortunately for three of the samples (C61183, C66515, C60552) the putative sub-chromosomal abnormality originates in regions of the genome for which information is either unavailable in the genome build or highly repetitive and not be accessible for analysis. Thus, in this case, the process was unable to determine the sub-chromosomal abnormalities reported in these three samples. The $z_{ij}$ values were all close to and centered around zero. Sample C65664 had a mosaic karyotype with isochromosome 20q, an abnormality that is associated with an event secondary to post zygotic error (Chen, C.-P. (2003) Detection of mosaic isochromosome 20q in amniotic fluid in a pregnancy with fetal arthrogryposis multiplex congenita and normal karyotype in fetal blood and postnatal samples of placenta, skin, and liver. Prenat. Diagn. 23, 85-87). Since cfDNA primarily originates from placental cytotrophoblasts, it is not expected that this abnormality would be detected using MPS. There were 1-2 small sub-chromosomal changes detected in these samples by MPS that were not reported in the karyotypes (Table 7).

Further Discussion

This example demonstrates that in non-mosaic cases, it is possible to obtain a full fetal molecular karyotype using MPS of maternal plasma cfDNA that is equivalent to CMA (chromosomal microarray), and in some cases is better than a metaphase karyotype obtained from chorionic villi or amniocytes. Such a non-invasive test could have immediate clinical utility, particularly in rural areas where invasive procedures are not readily available.

Using 25-mer tags at ~$10^9$ tags/sample, the results indicate that sufficient precision can be obtained between sequencing runs to reliably achieve 100 kb resolution across the genome. Even greater resolution can be achieved with deeper sequencing. The improvements in the v3 sequencing chemistry allowed for the use of 25-mer tags, compared to the 36-mers used in previous work (Bianchi, D. W., Platt, L. D., Goldberg, J. D., Abuhamad, A., Sehnert, A. J., Rava, R. P. (2012). Genome-wide fetal aneuploidy detection by maternal plasma DNA sequencing. Obstet. Gynecol. 119, 890-901). These short tags mapped with high efficiency across the genome, and the quantitative behavior demonstrated with the artificial mixture analyses validates the methodology. At today's costs, this depth of sequencing is approximately $1,000 per sample. This is comparable to the cost of a chromosome microarray result, but employs a risk-free blood draw rather than an invasive procedure. Deeper sequencing would allow for even finer resolution at an additional cost. Thus, this type of analysis could be implemented today as a reflex test when other clinical factors are present (such as sonographically-detected anomalies that are not typical of whole chromosome aneuploidy) when the patient declines an invasive procedure or prefers a blood test.

The lack of results on the mosaic samples (except for the artificial mixture) highlights the current limitations of both the microarray and MPS approaches. Sub-chromosomal abnormalities that originate in regions of the genome for which information is either unavailable in the genome build or highly repetitive will not be accessible for analysis. Such inaccessible genome regions are typically focused in the telomeres and centromeres of different chromosomes and in the short arms of acrocentric chromosomes. Also, the lower fetal fraction for the mosaic portion will be more challenging for detection and may require even deeper sequencing for effective classification.

Metaphase cytogenetic analysis from cell cultures, while considered "standard," has some limitations that need to be considered. For example, the ability to detect sub-chromosomal abnormalities is typically limited to sizes of 5 Mb or greater. This constraint is what led to the recent recommendation of using CMAs as a first tier test in clinical practice. Cell culture is biased towards the detection of more stable chromosomal configurations over significant structural alterations. In the case of fluorescence in situ hybridization (FISH), only the regions of the genome that are addressed by design of the FISH probes can be analyzed. Finally, as shown here, in actual clinical practice metaphase karyotypes can be reported to contain "chromosomal material of unknown origin." The MPS methodology of measuring copy number variation introduced in this work overcomes these limitations of karyotyping Importantly, our results showed that MPS was able to identify the potential source of the material of unknown origin for clinical samples C60193 and C61233. In addition, the MPS data showed small deletions in the termini of the chromosomes that the metaphase karyotype indicated were the breakpoints for the unknown chromosomal material in each of these samples. Such deletions at the breakpoints of translocations have been reported repeatedly in the literature (Howarth, K. D., Pole, J. C. M, Beavis, J. C., Batty, E. M., Newman, S., Bignell, G. R., and Edwards, P. A. W. (2011) Large duplications at reciprocal translocation breakpoints that might be the counterpart of large deletions and could arise from stalled replication bubbles. Genome Res. 21, 525-534). Based on these results, MPS may have the capabilities to identify both the presence of a sub-chromosomal duplication and suggest a translocation position based on small deletions (or duplications) elsewhere in the genome.

The methodologies described in this example also have applications beyond the determination of fetal sub-chromosomal abnormalities from cfDNA in maternal plasma. Ultimately, MPS can be applied to any mixed biological sample in which one wishes to determine the sub-chromosomal abnormalities in the minor component, even when the minor component represents only a few percent of the total DNA in the specimen. In prenatal diagnostics, samples obtained from chorionic villi could be analyzed for mosaic karyotypes or maternal contamination. Outside of prenatal diagnosis, many different cancers have been associated with copy number changes that could potentially be detected from cfDNA in the blood of the patient or a solid tumor sample that contains both normal and cancer cells. As the cost of MPS continues to drop, it is expected that its application for detecting sub-chromosomal abnormalities in mixed samples will find broad clinical utility.

Determination of fetal sub-chromosome abnormalities using deep sequencing of maternal plasma allows for a full molecular karyotype of the fetus to be determined noninvasively.

In addition to the example above, which shows that partial aneuploidies can be determined using cfDNA, a similar procedure can be used to determine whole chromosome numbers (whole chromosome aneuploidies) from cfDNA. See for example, example 16 in PCT application US2013/023887 (Publication No. WO2014/014497), filed Jan. 30, 2013 and incorporated herein by reference. Further, a similar procedure can use cfDNA to detect anueploidies associated with cancer. See for example, example 29 of PCT application US2013/023887, which application is incorporated in its entirety by reference.

What is claimed is:

1. A method for obtaining sequence information from a whole blood sample comprising cell-free DNA, said method comprising:
    (a) obtaining a plasma fraction of the whole blood sample, wherein the plasma fraction comprises the cell-free DNA;
    (b) exposing the plasma fraction to conditions that reduce the binding of the cell-free DNA to nucleosomal proteins, wherein the conditions comprise exposing the plasma fraction to polysorbate-20, and/or heating the plasma fraction to a temperature from about 55° C. to about 75° C.;
    (c) ligating sequencing adapters to ends of unpurified cell-free DNA fragments in the plasma fraction without first purifying the cell-free DNA from the plasma fraction, thereby preparing a sequencing library comprising library fragments having the sequencing adapters attached to either end of the unpurified cell-free DNA fragments; and
    (d) sequencing said sequencing library to obtain sequence information.

2. The method of claim 1, further comprising obtaining the whole blood sample comprising cell-free DNA from a subject.

3. The method of claim 1, wherein said whole blood sample is a peripheral blood sample.

4. The method of claim 1, wherein obtaining the plasma fraction comprises centrifuging the whole blood sample and removing a resulting buffy coat and hematocrit fractions.

5. The method of claim 4, wherein obtaining the plasma fraction further comprises centrifuging the plasma fraction to remove solids from the plasma fraction.

6. The method of claim 4, further comprising stabilizing white blood cells prior to centrifugation.

7. The method of claim 6, wherein only a single centrifugation step is performed on the whole blood sample prior to preparing the sequencing library, and wherein the single centrifugation step is performed at an acceleration of at least about 10,000 g.

8. The method of claim 1, wherein (c) comprises contacting the plasma fraction with the sequencing adapters and a ligase.

9. The method of claim 1, wherein (b) comprises exposing the plasma fraction to polysorbate-20 while the plasma fraction is in contact with the sequencing adapters and a ligase.

10. The method of claim 1, wherein prior to and during preparing the sequencing library from the cell-free DNA, no protease is added to the plasma fraction.

11. The method of claim 1, further comprising removing serum proteins from the plasma fraction prior to preparing the sequencing library from the cell-free DNA.

12. The method of claim 1, wherein the sequence information comprises sequence reads, and the method further comprises mapping the sequence reads to a reference sequence.

13. The method of claim 2, wherein said subject is a pregnant mother, and the cell-free DNA comprises fetal cell-free DNA of a fetus carried by the pregnant mother.

14. The method of claim 13, further comprising using the cell-free DNA to determine copy number variation (CNV) in the fetus.

15. The method of claim 2, wherein said subject is a cancer patient.

16. The method of claim 15, wherein the cell-free DNA comprises cell-free DNA of a cancer genome.

17. The method of claim 16, further comprising using the cell-free DNA to determine copy number variation (CNV) in the cancer genome.

18. The method of claim 1, wherein the conditions do not include the presence of a protease, sodium dodecyl sulfate, or heating to a temperature higher than 75° C.

19. The method of claim 1, wherein the obtained sequence information is usable for determining whole chromosome aneuploidy.

20. The method of claim 1, wherein the method further comprises preparing the unpurified cell-free DNA fragments from the cell-free DNA, wherein preparing the unpurified cell-free DNA fragments from the cell-free DNA comprises end repairing and d-A tailing the cell-free DNA.

21. The method of claim 1, further comprising, before (c), centrifuging the heated plasma fraction to produce a supernatant, wherein (c) comprises ligating sequencing adapters to ends of unpurified cell-free DNA fragments in the supernatant.

22. The method of claim 1, wherein the conditions of (b) comprise heating the plasma fraction to a temperature from 55° C. to 75° C.

23. The method of claim 1, wherein the conditions of (b) comprise heating the plasma fraction to a temperature from about 65° C. to about 75° C.

24. The method of claim 1, wherein the conditions of (b) comprise heating the plasma fraction to a temperature from 65° C. to 75° C.

25. A method for obtaining sequence information from a whole blood sample comprising cell-free DNA, said method comprising:
    (a) freezing the whole blood sample;
    (b) thawing the frozen whole blood sample;
    (c) separating solids from the thawed whole blood sample to obtain a liquid fraction, wherein the liquid fraction comprises the cell-free DNA;
    (d) reducing concentration of plasma proteins in the liquid fraction;
    (e) ligating sequencing adapters to ends of unpurified cell-free DNA fragments in the liquid fraction, thereby preparing a sequencing library comprising library fragments having the sequencing adapters attached to either end of the unpurified cell-free DNA fragments; and (f) sequencing said sequencing library to obtain sequence information.

26. The method of claim 25, further comprising obtaining the whole blood sample comprising cell-free DNA from a subject.

27. The method of claim 25, further comprising exposing the liquid fraction to polysorbate-20, and/or heating the liquid fraction to a temperature from about 55° C. to about 75° C.

28. The method of claim 26, wherein said subject is a pregnant mother, and wherein the cell-free DNA comprises fetal cell-free DNA of a fetus carried by the pregnant mother.

29. The method of claim 28, further comprising using the cell-free DNA to determine copy number variation (CNV) in the fetus.

30. The method of claim 26, wherein said subject is a cancer patient, and wherein the cell-free DNA comprises cell-free DNA of a cancer genome.

31. The method of claim 25, wherein said whole blood sample is a peripheral blood sample.

32. The method of claim 25, further comprising, prior to (a), fixing blood cells in the whole blood sample.

33. The method of claim 25, wherein separating solids from the thawed whole blood sample comprises centrifuging the thawed whole blood sample.

34. The method of claim 33, wherein only a single centrifugation step is performed on the thawed whole blood sample prior to preparing the sequencing library, and wherein the single centrifugation step is performed at an acceleration of at least about 10,000 g.

35. The method of claim 25, wherein prior to and during preparing a sequencing library from the cell-free DNA, no protease is added to the liquid fraction.

\* \* \* \* \*